(12) United States Patent
Li et al.

(10) Patent No.: US 10,211,414 B2
(45) Date of Patent: Feb. 19, 2019

(54) PHOSPHORESCENT TETRADENTATE METAL COMPLEXES HAVING MODIFIED EMISSION SPECTRA

(71) Applicants: Arizona Board of Regents on behalf of Arizona State University, Scottsdale, AZ (US); Universal Display Corporation, Ewing, NJ (US)

(72) Inventors: Jian Li, Tempe, AZ (US); Guijie Li, Tempe, AZ (US); Jason Brooks, Philadelphia, PA (US)

(73) Assignees: Arizona Board of Regents on behalf of Arizona State University, Scottsdale, AZ (US); Universal Display Corporation, Ewing, NJ (US)

( * ) Notice: Subject to any disclaimer, the term of this patent is extended or adjusted under 35 U.S.C. 154(b) by 0 days.

(21) Appl. No.: 15/615,566

(22) Filed: Jun. 6, 2017

(65) Prior Publication Data

US 2017/0331056 A1 Nov. 16, 2017

Related U.S. Application Data

(63) Continuation of application No. 14/300,832, filed on Jun. 10, 2014, now Pat. No. 9,673,409.

(60) Provisional application No. 61/833,091, filed on Jun. 10, 2013.

(51) Int. Cl.
*A61K 31/4427* (2006.01)
*H01L 51/00* (2006.01)
*C09K 11/06* (2006.01)
*C07F 15/00* (2006.01)
*H01L 51/50* (2006.01)

(52) U.S. Cl.
CPC ...... *H01L 51/0087* (2013.01); *A61K 31/4427* (2013.01); *C07F 15/0086* (2013.01); *C09K 11/06* (2013.01); *C09K 2211/1007* (2013.01); *C09K 2211/1029* (2013.01); *C09K 2211/1044* (2013.01); *C09K 2211/185* (2013.01); *H01L 51/5016* (2013.01); *Y02E 10/549* (2013.01)

(58) Field of Classification Search
CPC .................................................. H01L 51/0087
See application file for complete search history.

(56) References Cited

U.S. PATENT DOCUMENTS

| 4,769,292 | A | 9/1988 | Tang et al. |
| 5,707,745 | A | 1/1998 | Forrest et al. |
| 5,844,363 | A | 12/1998 | Gu et al. |
| 6,200,695 | B1 | 3/2001 | Arai |
| 6,303,238 | B1 | 10/2001 | Thompson et al. |
| 6,780,528 | B2 | 8/2004 | Tsuboyama et al. |
| 7,002,013 | B1 | 2/2006 | Chi et al. |

(Continued)

FOREIGN PATENT DOCUMENTS

| CN | 1777663 | 5/2006 |
| CN | 1894267 | 1/2007 |

(Continued)

OTHER PUBLICATIONS

First Office Action (English translation only) issued by the Chinese Patent Office dated Mar. 30, 2017 for Pat. App. No. 201410256105.3, 9 pages.

(Continued)

*Primary Examiner* — Brian E McDowell
(74) *Attorney, Agent, or Firm* — Fish & Richardson P.C.

(57) ABSTRACT

Multidentate metal complexes useful as phosphorescent emitters in display and lighting applications having the following structures:

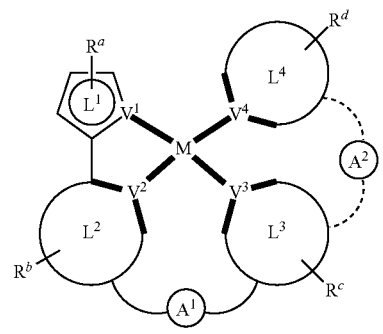

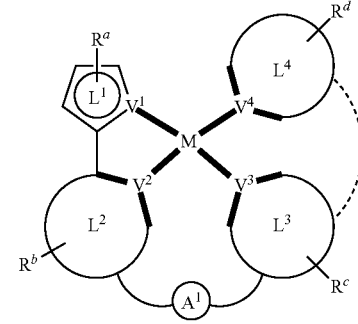

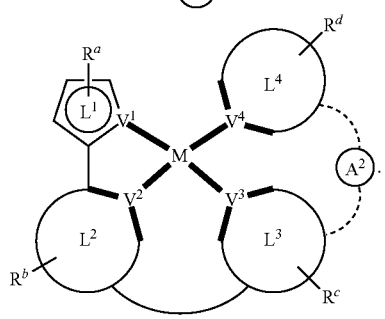

20 Claims, 10 Drawing Sheets

(56) References Cited

U.S. PATENT DOCUMENTS

| | | |
|---|---|---|
| 7,037,599 B2 | 5/2006 | Culligan et al. |
| 7,279,704 B2 | 10/2007 | Walters et al. |
| 7,332,232 B2 | 2/2008 | Ma et al. |
| 7,442,797 B2 | 10/2008 | Itoh et al. |
| 7,501,190 B2 | 3/2009 | Ise |
| 7,655,322 B2 | 2/2010 | Forrest et al. |
| 7,947,383 B2 | 5/2011 | Ise et al. |
| 8,389,725 B2 | 3/2013 | Li et al. |
| 8,617,723 B2 | 12/2013 | Stoessel |
| 8,816,080 B2 | 8/2014 | Li et al. |
| 8,871,361 B2 | 10/2014 | Xia et al. |
| 8,927,713 B2 | 1/2015 | Li et al. |
| 8,946,417 B2 | 2/2015 | Li et al. |
| 9,059,412 B2 | 6/2015 | Zeng et al. |
| 9,224,963 B2 | 12/2015 | Li et al. |
| 9,238,668 B2 | 1/2016 | Li et al. |
| 9,312,505 B2 | 4/2016 | Brooks et al. |
| 9,318,725 B2 | 4/2016 | Li |
| 9,324,957 B2 | 4/2016 | Li et al. |
| 9,382,273 B2 | 7/2016 | Li |
| 9,385,329 B2 | 7/2016 | Li et al. |
| 9,425,415 B2 | 8/2016 | Li et al. |
| 9,461,254 B2 | 10/2016 | Tsai |
| 9,550,801 B2 | 1/2017 | Li et al. |
| 9,617,291 B2 | 4/2017 | Li et al. |
| 9,673,409 B2 | 6/2017 | Li et al. |
| 9,698,359 B2 | 7/2017 | Li et al. |
| 9,711,739 B2 | 7/2017 | Li |
| 9,711,742 B2 | 7/2017 | Li et al. |
| 9,755,163 B2 | 9/2017 | Li et al. |
| 9,879,039 B2 | 1/2018 | Li |
| 9,882,150 B2 | 1/2018 | Li |
| 9,899,614 B2 | 2/2018 | Li |
| 9,920,242 B2 | 3/2018 | Li |
| 9,923,155 B2 | 3/2018 | Li |
| 9,941,479 B2 | 4/2018 | Li |
| 9,947,881 B2 | 4/2018 | Li |
| 10,020,455 B2 | 7/2018 | Li |
| 10,033,003 B2 | 7/2018 | Li |
| 10,056,564 B2 | 8/2018 | Li |
| 10,056,567 B2 | 8/2018 | Li |
| 2002/0068190 A1 | 6/2002 | Tsuboyama et al. |
| 2003/0062519 A1 | 4/2003 | Yamazaki et al. |
| 2003/0186077 A1 | 10/2003 | Chen |
| 2005/0170207 A1 | 8/2005 | Ma et al. |
| 2005/0260446 A1 | 11/2005 | Mackenzie et al. |
| 2006/0073359 A1 | 4/2006 | Ise et al. |
| 2006/0094875 A1 | 5/2006 | Itoh et al. |
| 2006/0182992 A1 | 8/2006 | Nii et al. |
| 2006/0202197 A1 | 9/2006 | Nakayama et al. |
| 2006/0210831 A1 | 9/2006 | Sano et al. |
| 2006/0255721 A1 | 11/2006 | Igarashi |
| 2006/0263635 A1 | 11/2006 | Ise |
| 2006/0286406 A1 | 12/2006 | Igarashi et al. |
| 2007/0057630 A1 | 3/2007 | Nishita et al. |
| 2007/0059551 A1 | 3/2007 | Yamazaki |
| 2007/0082284 A1 | 4/2007 | Stoessel et al. |
| 2007/0103060 A1 | 5/2007 | Itoh et al. |
| 2008/0001530 A1 | 1/2008 | Ise et al. |
| 2008/0036373 A1 | 2/2008 | Itoh et al. |
| 2008/0054799 A1 | 3/2008 | Satou |
| 2008/0079358 A1 | 4/2008 | Satou |
| 2008/0111476 A1 | 5/2008 | Choi et al. |
| 2008/0241518 A1 | 10/2008 | Satou et al. |
| 2008/0241589 A1 | 10/2008 | Fukunaga et al. |
| 2009/0026936 A1 | 1/2009 | Satou et al. |
| 2009/0026939 A1 | 1/2009 | Kinoshita et al. |
| 2009/0032989 A1 | 2/2009 | Karim et al. |
| 2009/0039768 A1 | 2/2009 | Igarashi et al. |
| 2009/0079340 A1 | 3/2009 | Kinoshita et al. |
| 2009/0128008 A1 | 5/2009 | Ise et al. |
| 2009/0153045 A1 | 6/2009 | Kinoshita et al. |
| 2009/0218561 A1 | 9/2009 | Kitamura et al. |
| 2009/0261721 A1 | 10/2009 | Murakami et al. |
| 2009/0267500 A1 | 10/2009 | Kinoshita et al. |
| 2010/0000606 A1 | 1/2010 | Thompson et al. |
| 2010/0013386 A1 | 1/2010 | Thompson et al. |
| 2010/0171111 A1 | 7/2010 | Takada et al. |
| 2010/0171418 A1 | 7/2010 | Kinoshita et al. |
| 2011/0049496 A1 | 3/2011 | Fukuzaki |
| 2011/0227058 A1 | 9/2011 | Masui et al. |
| 2012/0095232 A1 | 4/2012 | Li et al. |
| 2012/0181528 A1 | 7/2012 | Takada et al. |
| 2012/0215001 A1 | 8/2012 | Li et al. |
| 2012/0223634 A1 | 9/2012 | Xia et al. |
| 2012/0273736 A1 | 11/2012 | James et al. |
| 2012/0302753 A1 | 11/2012 | Li |
| 2013/0048963 A1 | 2/2013 | Beers et al. |
| 2013/0082245 A1 | 4/2013 | Kottas et al. |
| 2013/0168656 A1 | 7/2013 | Tsai et al. |
| 2013/0172561 A1 | 7/2013 | Tsai et al. |
| 2013/0203996 A1 | 8/2013 | Li et al. |
| 2013/0237706 A1 | 9/2013 | Li |
| 2013/0341600 A1 | 12/2013 | Lin et al. |
| 2014/0014922 A1 | 1/2014 | Lin et al. |
| 2014/0027733 A1 | 1/2014 | Zeng et al. |
| 2014/0084261 A1 | 3/2014 | Brooks et al. |
| 2014/0114072 A1 | 4/2014 | Li et al. |
| 2014/0191206 A1 | 7/2014 | Cho |
| 2014/0203248 A1 | 7/2014 | Zhou et al. |
| 2014/0326960 A1 | 11/2014 | Kim et al. |
| 2014/0330019 A1 | 11/2014 | Li et al. |
| 2014/0364605 A1 | 12/2014 | Li et al. |
| 2015/0008419 A1 | 1/2015 | Li |
| 2015/0028323 A1 | 1/2015 | Xia et al. |
| 2015/0069334 A1 | 3/2015 | Xia et al. |
| 2015/0105556 A1 | 4/2015 | Li et al. |
| 2015/0162552 A1 | 6/2015 | Li et al. |
| 2015/0194616 A1 | 7/2015 | Li et al. |
| 2015/0207086 A1 | 7/2015 | Li et al. |
| 2015/0228914 A1 | 8/2015 | Li et al. |
| 2015/0274762 A1 | 10/2015 | Li et al. |
| 2015/0287938 A1 | 10/2015 | Li et al. |
| 2015/0318500 A1 | 11/2015 | Li |
| 2015/0349279 A1 | 12/2015 | Li et al. |
| 2016/0028028 A1 | 1/2016 | Li et al. |
| 2016/0043331 A1 | 2/2016 | Li et al. |
| 2016/0072082 A1 | 3/2016 | Brooks et al. |
| 2016/0133862 A1 | 5/2016 | Li et al. |
| 2016/0197291 A1 | 7/2016 | Xia et al. |
| 2016/0285015 A1 | 9/2016 | Li et al. |
| 2016/0359120 A1 | 12/2016 | Li |
| 2016/0359125 A1 | 12/2016 | Li |
| 2017/0005278 A1 | 1/2017 | Li et al. |
| 2017/0012224 A1 | 1/2017 | Li et al. |
| 2017/0040555 A1 | 2/2017 | Li et al. |
| 2017/0047533 A1 | 2/2017 | Li et al. |
| 2017/0066792 A1 | 3/2017 | Li et al. |
| 2017/0069855 A1 | 3/2017 | Li et al. |
| 2017/0267923 A1 | 9/2017 | Li |
| 2017/0271611 A1 | 9/2017 | Li et al. |
| 2017/0301871 A1 | 10/2017 | Li |
| 2017/0305881 A1 | 10/2017 | Li et al. |
| 2017/0331056 A1 | 11/2017 | Li et al. |
| 2017/0373260 A1 | 12/2017 | Li |
| 2018/0006246 A1 | 1/2018 | Li |
| 2018/0053904 A1 | 2/2018 | Li |
| 2018/0130960 A1 | 5/2018 | Li |
| 2018/0148464 A1 | 5/2018 | Li |
| 2018/0166655 A1 | 6/2018 | Li et al. |
| 2018/0175329 A1 | 6/2018 | Li |
| 2018/0194790 A1 | 7/2018 | Li |
| 2018/0219161 A1 | 8/2018 | Li |
| 2018/0226593 A1 | 8/2018 | Li |

FOREIGN PATENT DOCUMENTS

| | | |
|---|---|---|
| CN | 101142223 | 3/2008 |
| CN | 101667626 | 3/2010 |
| CN | 102449108 A | 5/2012 |
| CN | 102892860 | 1/2013 |
| CN | 102971396 | 3/2013 |
| CN | 103102372 A1 | 5/2013 |
| CN | 104232076 | 12/2014 |

(56) References Cited

FOREIGN PATENT DOCUMENTS

| | | |
|---|---|---|
| CN | 104693243 | 6/2015 |
| CN | 105367605 | 3/2016 |
| CN | 105418591 | 3/2016 |
| EP | 1808052 | 7/2007 |
| EP | 1874893 | 1/2008 |
| EP | 1874894 | 1/2008 |
| EP | 1919928 | 5/2008 |
| EP | 2036907 | 3/2009 |
| EP | 2096690 A2 | 9/2009 |
| EP | 2417217 | 2/2012 |
| EP | 2112213 | 7/2012 |
| JP | 2005267557 | 9/2005 |
| JP | 2005310733 | 11/2005 |
| JP | 2006047240 | 2/2006 |
| JP | 2006232784 | 9/2006 |
| JP | 2006242080 | 9/2006 |
| JP | 2006242081 | 9/2006 |
| JP | 2006256999 | 9/2006 |
| JP | 2006257238 | 9/2006 |
| JP | 2006261623 | 9/2006 |
| JP | 2006290988 | 10/2006 |
| JP | 2006313796 | 11/2006 |
| JP | 2006332622 | 12/2006 |
| JP | 2006351638 | 12/2006 |
| JP | 2007019462 | 1/2007 |
| JP | 2007042875 | 2/2007 |
| JP | 2007051243 | 3/2007 |
| JP | 2007053132 | 3/2007 |
| JP | 2007066581 | 3/2007 |
| JP | 2007073620 | 3/2007 |
| JP | 2007073845 | 3/2007 |
| JP | 2007073900 | 3/2007 |
| JP | 2007080593 | 3/2007 |
| JP | 2007080677 | 3/2007 |
| JP | 2007088105 | 4/2007 |
| JP | 2007088164 | 4/2007 |
| JP | 2007096259 | 4/2007 |
| JP | 2007110067 | 4/2007 |
| JP | 2007110102 | 4/2007 |
| JP | 2007519614 | 7/2007 |
| JP | 2007258550 | 10/2007 |
| JP | 2007324309 | 12/2007 |
| JP | 2008010353 | 1/2008 |
| JP | 2008091860 | 4/2008 |
| JP | 2008103535 | 5/2008 |
| JP | 2008108617 | 5/2008 |
| JP | 2008109085 | 5/2008 |
| JP | 2008109103 | 5/2008 |
| JP | 2008160087 | 7/2008 |
| JP | 2008198801 | 8/2008 |
| JP | 2008270729 | 11/2008 |
| JP | 2008270736 | 11/2008 |
| JP | 2009016184 | 1/2009 |
| JP | 2009016579 | 1/2009 |
| JP | 2009032977 | 2/2009 |
| JP | 2009032988 | 2/2009 |
| JP | 2009076509 A | 4/2009 |
| JP | 2009161524 | 7/2009 |
| JP | 2009247171 | 11/2009 |
| JP | 2009266943 | 11/2009 |
| JP | 2009267244 | 11/2009 |
| JP | 2009272339 | 11/2009 |
| JP | 2009283891 | 12/2009 |
| JP | 2010135689 | 6/2010 |
| JP | 2010171205 | 8/2010 |
| JP | 2011071452 | 4/2011 |
| JP | 2012079895 | 4/2012 |
| JP | 2012079898 | 4/2012 |
| JP | 2012522843 A1 | 9/2012 |
| JP | 2012207231 A1 | 10/2012 |
| JP | 2012222255 | 11/2012 |
| JP | 2012231135 | 11/2012 |
| JP | 2013023500 | 2/2013 |
| JP | 2013048256 | 3/2013 |
| JP | 2013053149 A1 | 3/2013 |
| JP | 2013525436 | 6/2013 |
| JP | 2014019701 | 2/2014 |
| JP | 2014058504 | 4/2014 |
| JP | 56045505 | 10/2014 |
| JP | 2014221807 | 11/2014 |
| JP | 2014239225 | 12/2014 |
| JP | 2015081257 | 4/2015 |
| KR | 1020060115371 | 11/2006 |
| KR | 2007061830 | 6/2007 |
| KR | 2007112465 | 11/2007 |
| KR | 1020130043460 | 4/2013 |
| TW | 200701835 | 1/2007 |
| TW | 201307365 | 2/2013 |
| TW | 201710277 | 3/2017 |
| WO | WO2000070655 | 11/2000 |
| WO | WO2004003108 | 1/2004 |
| WO | WO2004108857 | 12/2004 |
| WO | WO2005042444 | 5/2005 |
| WO | WO2005042550 | 5/2005 |
| WO | WO2006033440 | 3/2006 |
| WO | WO2006098505 | 9/2006 |
| WO | WO2006115299 | 11/2006 |
| WO | WO2006115301 | 11/2006 |
| WO | WO2007034985 | 3/2007 |
| WO | WO2007069498 | 6/2007 |
| WO | WO2008066192 | 6/2008 |
| WO | WO2008066195 | 6/2008 |
| WO | WO2008066196 | 6/2008 |
| WO | WO2008117889 | 10/2008 |
| WO | WO2008123540 | 10/2008 |
| WO | WO2009017211 | 2/2009 |
| WO | WO2010118026 | 10/2010 |
| WO | WO2011137429 | 11/2011 |
| WO | WO2011137431 | 11/2011 |
| WO | WO2012112853 | 8/2012 |
| WO | WO2012116231 A1 | 8/2012 |
| WO | WO2012142387 | 10/2012 |
| WO | WO2012162488 | 11/2012 |
| WO | WO2012163471 | 12/2012 |
| WO | WO2013130483 | 9/2013 |
| WO | WO2014016611 | 1/2014 |
| WO | WO2014031977 | 2/2014 |
| WO | 2711999 | 3/2014 |
| WO | WO2014047616 | 3/2014 |
| WO | WO2014109814 | 7/2014 |
| WO | WO2014208271 | 12/2014 |
| WO | WO2015027060 | 2/2015 |
| WO | WO2015131158 | 9/2015 |
| WO | WO2016025921 | 2/2016 |
| WO | WO2016029137 | 2/2016 |
| WO | WO2016029186 | 2/2016 |
| WO | WO2016197019 | 12/2016 |
| WO | WO2018071697 | 4/2018 |
| WO | WO2018140765 | 8/2018 |

OTHER PUBLICATIONS

International Search Report and Written Opinion mailed by the International Searching Authority dated Nov. 25, 2014 for PCT/US2014/052084 filed Aug. 21, 2014 (pp. 1-9).
International Preliminary Report on Patentability mailed by the International Bureau dated Mar. 3, 2016 for PCT/US2014/052084 filed Aug. 21, 2014 (pp. 1-7).
Wong; Challenges in organometallic research—Great opportunity for solar cells and OLEDs, Journal of Organometallic Chemistry, 2009, 694, 2644-2647.
JP2009267244, English Translation from EPO, Nov. 2009, 80 pages.
JP2010135689, English translation from EPO, Jun. 2010, 95 pages.
Chi et al.; Transition-metal phosphors with cyclometalating ligands: fundamentals and applications, Chemical Society Reviews, vol. 39, No. 2, Feb. 2010, pp. 638-655.
Satake et al., "Interconvertible Cationic and Neutral Pyridinylimidazole η3-Allylpalladium Complexes. Structural Assignment by 1H, 13C, and 15N NMR and X-ray Diffraction", Organometallics, vol. 18, No. 24, 1999, pp. 5108-5111.

(56) References Cited

OTHER PUBLICATIONS

Baldo et al., "Highly Efficient Phosphorescent Emission from Organic Electroluminescent Devices," Nature, vol. 395, Sep. 10, 1998, pp. 151-154.
Baldo et al., "Very high-efficiency green organic light-emitting devices based on electrophosphorescence," Applied Physics Letters, vol. 75, No. 1, Jul. 5, 1999, pp. 4-6.
Ying Yang et al., "Induction of Circularly Polarized Electroluminescence from an Achiral Light-Emitting Polymer via a Chiral Small-Molecule Dopant," Advanced Materials, vol. 25, Issue 18, May 14, 2013, pp. 2624-2628.
Ayan Maity et al., "Room-temperature synthesis of cyclometalated iridium(III) complexes; kinetic isomers and reactive functionalities" Chem. Sci., vol. 4, pp. 1175-1181 (2013).
Shiro Koseki et al., "Spin-orbit coupling analyses of the geometrical effects on phosphorescence in Ir(ppy)3 and its derivatives", J. Phys. Chem. C, vol. 117, pp. 5314-5327 (2013).
Ji Hyun Seo et al., "Efficient blue-green organic light-emitting diodes based on heteroleptic tris-cyclometalated iridium (III) complexes". Thin Solid Films, vol. 517, pp. 1807-1810 (2009).
Barry O'Brien et al.: White organic light emitting diodes using Pt-based red, green and blue phosphorescent dopants. Proc. SPIE, vol. 8829, pp. 1-6, Aug. 25, 2013.
Xiao-Chu Hang et al., "Highly Efficient Blue-Emitting Cyclometalated Platinum(II) Complexes by Judicious Molecular Design," Angewandte Chemie, International Edition, vol. 52, Issue 26, Jun. 24, 2013, pp. 6753-6756.
Vanessa Wood et al., "Colloidal quantum dot light-emitting devices," Nano Reviews, vol. 1, 2010, 8 pages.
Glauco Ponterini et al., "Comparison of Radiationless Decay Processes in Osmium and Platinum Porphyrins," J. Am. Chem. Soc., vol. 105, No. 14, 1983, pp. 4639-4645.
Shizuo Tokito et al., "Confinement of triplet energy on phosphorescent molecules for highly-efficient organic blue-light-emitting devices," Applied Physics Letters, vol. 83, No. 3, Jul. 21, 2003, pp. 569-571.
Brian W. D'Andrade et al., "Controlling Exciton Diffusion in Multilayer White Phosphorescent Organic Light Emitting Devices," Adv. Mater., vol. 14, No. 2, Jan. 16, 2002, pp. 147-151.
Dileep A. K. Vezzu et al., "Highly Luminescent Tetradentate Bis-Cyclometalated Platinum Complexes: Design, Synthesis, Structure, Photophysics, and Electroluminescence Application," Inorg. Chem., vol. 49, 2010, pp. 5107-5119.
Evan L. Williams et al., "Excimer-Based White Phosphorescent Organic Light Emitting Diodes with Nearly 100% Internal Quantum Efficiency," Adv. Mater., vol. 19, 2007, pp. 197-202.
Shih-Chun Lo et al., "High-Triplet-Energy Dendrons: Enhancing the Luminescence of Deep Blue Phosphorescent Iridium(III) Complexes," J. Am. Chem. Soc., vol. 131, 2009, pp. 16681-16688.
Jan Kalinowski et al., "Light-emitting devices based on organometallic platinum complexes as emitters," Coordination Chemistry Reviews, vol. 255, 2011, pp. 2401-2425.
Ke Feng et al., "Norbornene-Based Copolymers Containing Platinum Complexes and Bis(carbazolyl)benzene Groups in Their Side-Chains," Macromolecules, vol. 42, 2009, pp. 6855-6864.
Chi-Ming Che et al., "Photophysical Properties and OLED Applications of Phosphorescent Platinum(II) Schiff Base Complexes," Chem. Eur. J., vol. 16, 2010, pp. 233-247.
Stephen R. Forrest, "The path to ubiquitous and low-cost organic electronic appliances on plastic," Nature, vol. 428, Apr. 29, 2004, pp. 911-918.
Nicholas R. Evans et al., "Triplet Energy Back Transfer in Conjugated Polymers with Pendant Phosphorescent Iridium Complexes," J. Am. Chem. Soc., vol. 128, 2006, pp. 6647-6656.
Xiaofan Ren et al., "Ultrahigh Energy Gap Hosts in Deep Blue Organic Electrophosphorescent Devices," Chem. Mater., vol. 16, 2004, pp. 4743-4747.
Jeonghun Kwak et al., "Bright and Efficient Full-Color Colloidal Quantum Dot Light-Emitting Diodes Using an Inverted Device Structure," Nano Lett., 2012, Vo. 12, pp. 2362-2366.
Hirohiko Fukagawa et al., "Highly Efficient and Stable Red Phosphorescent Organic Light-Emitting Diodes Using Platinum Complexes," Adv. Mater., 2012, vol. 24, pp. 5099-5103.
Eric Turner et al., "Cyclometalated Platinum Complexes with Luminescent Quantum Yields Approaching 100%," Inorg. Chem., 2013, vol. 52, pp. 7344-7351.
Steven C. F. Kui et al., "Robust Phosphorescent Platinum(II) Complexes Containing Tetradentate O/\N/\C/\N Ligands: Excimeric Excited State and Application in Organic White-Light-Emitting Diodes," Chem. Eur. J., 2013, vol. 19, pp. 69-73.
Steven C. F. Kui et al., "Robust phosphorescent platinum(II) complexes with tetradentate O/\N/\C/\N ligands: high efficiency OLEDs with excellent efficiency stability," Chem. Commun., 2013, vol. 49, pp. 1497-1499.
Guijie Li et al., "Efficient and stable red organic light emitting devices from a tetradentate cyclometalated platinum complex," Organic Electronics, 2014, vol. 15 pp. 1862-1867.
Guijie Li et al., Efficient and Stable White Organic Light-Emitting Diodes Employing a Single Emitter, Adv. Mater., 2014, vol. 26, pp. 2931-2936.
Barry O'Brien et al., "High efficiency white organic light emitting diodes employing blue and red platinum emitters," Journal of Photonics for Energy, vol. 4, 2014, pp. 043597-1-8.
Kai Li et al., "Light-emitting platinum(II) complexes supported by tetradentate dianionic bis(N-heterocyclic carbene) ligands: towards robust blue electrophosphors," Chem. Sci., 2013, vol. 4, pp. 2630-2644.
Tyler Fleetham et al., "Efficient "pure" blue OLEDs employing tetradentate Pt complexes with a narrow spectral bandwidth," Advanced Materials (Weinheim, Germany), Vo. 26, No. 41, 2014, pp. 7116-7121.
Dorwald; "Side Reactions in Organic Synthesis: A Guide to Successful Synthesis Design," Chapter 1, 2005 Wiley-VCH Verlag GmbH & Co. KGaA, Wienheim, 32 pages.
Murakami; JP 2007258550, English machine translation from EPO, Oct. 4, 2007. 80 pages.
Murakami; JP 2007324309, English machine translation from EPO, Dec. 13, 2007, 89 pages.
Marc Lepeltier et al., "Efficient blue green organic light-emitting devices based on a monofluorinated heteroleptic iridium(III) complex," Synthetic Metals, vol. 199, 2015, pp. 139-146.
Stefan Bernhard, "The First Six Years: A Report," Department of Chemistry, Princeton University, May 2008, 11 pages.
Maestri et al., "Absorption Spectra and Luminescence Properties of Isomeric Platinum (II) and Palladium (II) Complexes Containing 1,1'-Biphenyldiyl, 2-Phenylpyridine, and 2,2'-Bipyridine as Ligands," Helvetica Chimica Acta, vol. 71, Issue 5, Aug. 10, 1988, pp. 1053-1059.
Guijie Li et al., "Modifying Emission Spectral Bandwidth of Phosphorescent Platinum(II) Complexes Through Synthetic Control," Inorg. Chem. 2017, 56, 8244-8256.
Tyler Fleetham et al., "Efficient Red-Emitting Platinum Complex with Long Operational Stability," ACS Appl. Mater. Interfaces 2015, 7, 16240-16246.
Supporting Information: Xiao-Chun Hang et al., "Highly Efficient Blue-Emitting Cyclometalated Platinum(II) Complexes by Judicious Molecular Design," Wiley-VCH 2013, 7 pages.
Russell J. Holmes et al., "Blue and Near-UV Phosphorescence from Iridium Complexes with Cyclometalated Pyrazolyl or N-Heterocyclic Carbene Ligands," Inorganic Chemistry, 2005, vol. 44, No. 22, pp. 7995-8003.
Office Action issued by Japanese Patent Office dated Mar. 20, 2018, for Patent Application No. 2014-119789, 10 pages.
U.S. Appl. No. 15/119,961, filed Aug. 18, 2016, US-2017-0069855-A1, Chiral Metal Complexes as Emitters for Organic Polarized Electroluminescent Devices, Jian Li.
U.S. Appl. No. 15/503,690, filed Feb. 13, 2017, US-2017-0305881-A1, Non-Platinum Metal Complexes for Excimer Based Single Dopant White Organic Light Emitting Diodes, Jian Li, Liang Huang, Tyler Fleetham.
U.S. Appl. No. 15/505,527, filed Feb. 21, 2017, US-2017-0271511-A1, Organic Light-Emitting Diodes With Fluorescent and Phosphorescent Emitters, Jian Li, Tyler Fleetham.

(56) References Cited

OTHER PUBLICATIONS

U.S. Appl. No. 15/505,544, filed Feb. 21, 2017, U.S. Pat. No. 9,920,242, Metal-Assisted Delayed Fluorescent Materials as Co-Host Materials for Fluorescent OLEDS, Jian Li.
U.S. Appl. No. 15/925,203, filed Mar. 19, 2018, Metal-Assisted Delayed Fluorescent Materials as Co-Host Materials for Fluorescent OLEDS, Jian Li.
U.S. Appl. No. 15/508,032, filed Mar. 1, 2017, US-2017-0309943-A1, Ionic Liquid Catholytes and Electrochemical Devices Containing Same, Charles Austen Angell, Leigang Xue.
U.S. Appl. No. 15/577,655, filed Nov. 28, 2017, Transparent Electroluminescent Devices With Controlled One-Side Emissive Displays, Jian Li.
U.S. Appl. No. 62/323,383, filed Apr. 15, 2016, OLED With Doped Electron Blocking Layer, Jian Li.
U.S. Appl. No. 62/377,747, filed Aug. 22, 2016, OLED With Multi-Emissive Material Layer, Jian Li.
U.S. Appl. No. 62/407,020, filed Oct. 12, 2016, Narrow Band Red Phosphorescent Tetradentate Platinum (II) Complexes, Jian Li, Qunbo Mei.
U.S. Appl. No. 62/435,455, filed Dec. 16, 2016, Organic Light Emitting Diode With Split Emissive Layer, Jian Li, Kody George Klimes.
U.S. Appl. No. 14/437,963, filed Apr. 23, 2015, US-2015-0273762-A1, Metal Complexes, Methods, and Uses Thereof, Eric Turner, Jian Li.
U.S. Appl. No. 15/905,385, filed Feb. 26, 2018, Metal Complexes, Methods, and Uses Thereof, Eric Turner, Jian L.
U.S. Appl. No. 13/263,096, filed Jan. 3, 2014, U.S. Pat. No. 8,946,417, Synthesis of Four Coordinated Platinum Complexes and Their Applications in Light Emitting Devices Thereof, Eric Turner, Jian Li, Zixing Wang.
U.S. Appl. No. 14/611,654, filed Feb. 2, 2015, U.S. Pat. No. 9,550,801, Synthesis of Four Coordinated Platinum Complexes and Their Applications in Light Emitting Devices Thereof, Eric Turner, Jian Li, Zixing Wang.
U.S. Appl. No. 13/695,338, filed May 16, 2013, U.S. Pat. No. 9,324,957, Synthesis of Four Coordinated Gold Complexes and Their Applications in Light Emitting Devices Thereof, Eric Turner, Jian Li.
U.S. Appl. No. 14/562,195, filed Dec. 5, 2014, U.S. Pat. No. 9,244,963, Stable Emitters, Jian Li, Guijie Li.
U.S. Appl. No. 13/695,337, filed Mar. 13, 2013, US-2013-0203996-A1, Synthesis of Four Coordinated Palladium Complexes and Their Applications in Light Emitting Devices Thereof, Eric Turner, Jian Li.
U.S. Appl. No. 14/145,461, filed Dec. 31, 2013, U.S. Pat. No. 9,382,273, Synthesis of Four Coordinated Palladium Complexes and Their Applications in Light Emitting Devices Thereof, Eric Turner, Jian Li.
U.S. Appl. No. 15/202,058, filed Jul. 5, 2016, U.S. Pat. No. 9,755,163, Synthesis of Four Coordinated Palladium Complexes and Their Applications in Light Emitting Devices Thereof, Eric Turner, Jian Li.
U.S. Appl. No. 15/692,660, filed Aug. 31, 2017, Synthesis of Four Coordinated Palladium Complexes and Their Applications in Light Emitting Devices Thereof, Eric Turner, Jian Li.
U.S. Appl. No. 13/399,252, filed Feb. 17, 2012, U.S. Pat. No. 8,816,080, Four Coordinated Platinum and Palladium Complexes With Geometrically Distorted Charge Transfer State and Their Applications in Light Emitting Devices, Eric Turner, Jian Li, Xiaochun Hang.
U.S. Appl. No. 14/332,610, filed Jul. 16, 2014, U.S. Pat. No. 8,927,713, Four Coordinated Platinum and Palladium Complexes With Geometrically Distorted Charge Transfer State and Their Applications in Light Emitting Devices, Eric Turner, Jian Li, Xiaochun Hang.
U.S. Appl. No. 14/589,599, filed Jan. 5, 2015, U.S. Pat. No. 9,425,415, Four Coordinated Platinum and Palladium Complexes With Geometrically Distorted Charge Transfer State and Their Applications in Light Emitting Devices, Eric Turner, Jian Li, Xiaochun Hang.
U.S. Appl. No. 15/243,801, filed Aug. 22, 2016, U.S. Pat. No. 9,711,742, Four Coordinated Platinum and Palladium Complexes With Geometrically Distorted Charge Transfer State and Their Applications in Light Emitting Devices, Eric Turner, Jian Li, Xiaochun Hang.
U.S. Appl. No. 13/479,921, filed May 24, 2012, U.S. Pat. No. 9,238,668, Synthesis of Platinum and Palladium Complexes as Narrow-Band Phosphorescent Emitters for Full Color Displays, Eric Turner, Jian Li.
U.S. Appl. No. 14/996,522, filed Jan. 15, 2016, U.S. Pat. No. 9,698,359, Synthesis of Platinum and Palladium Complexes as Narrow-Band Phosphorescent Emitters for Full Color Displays, Eric Turner, Jian Li.
U.S. Appl. No. 15/640,686, filed Jul. 3, 2017, US-2017-0373260-A1, Synthesis of Platinum and Palladium Complexes as Narrow-Band Phosphorescent Emitters for Full Color Displays, Eric Turner, Jian Li.
U.S. Appl. No. 14/430,454, filed Mar. 23, 2015, U.S. Pat. No. 9,882,150, Metal Compounds, Methods, and Uses Thereof, Guijie Li, Jian Li.
U.S. Appl. No. 15/882,358, filed Jan. 29, 2018, Metal Compounds, Methods, and Uses Thereof, Guijie Li, Jian Li.
U.S. Appl. No. 14/913,306, filed Feb. 19, 2016, U.S. Pat. No. 9,899,614, Phosphorescent Tetradentate Metal Complexes Having Modified Emissions Spectra, Guijie Li, Jason Brooks, Jian Li.
U.S. Appl. No. 14/300,832, filed Jun. 10, 2014, U.S. Pat. No. 9,673,409, Phosphorescent Tetradentate Metal Complexes Having Modified Emission Spectra, Guijie Li, Jason Brooks, Jian Li.
U.S. Appl. No. 15/900,260, filed Feb. 20, 2018, Phosphorescent Tetradentate Metal Complexes Having Modified Emission Spectra, Guijie Li, Jason Brooks, Jian Li, Jason Brooks.
U.S. Appl. No. 14/513,506, filed Oct. 14, 2014, U.S. Pat. No. 9,385,329, Platinum Complexes and Devices, Guijie Li, Jason Brooks, Jian Li.
U.S. Appl. No. 15/202,111, filed Jul. 5, 2016, U.S. Pat. No. 9,947,881, Platinum Complexes and Devices, Guijie Li, Jason Brooks, Jian Li.
U.S. Appl. No. 15/947,273, filed Apr. 6, 2018, Platinum Complexes and Devices, Guijie Li, Jason Brooks, Jian Li.
U.S. Appl. No. 14/591,188, filed Jan. 7, 2015, US-2015-0194616-A1, Tetradentate Plantinum and Palladium Complex Emitters Containing Phenyl-Pyrazole and its Analogues, Guijie Li, Jian Li.
U.S. Appl. No. 61/897,065, filed Oct. 29, 2013, Efficient and Stable Blue and White Organic Light Emitting Diodes, Guijie Li, Jian Li.
U.S. Appl. No. 14/728,848, filed Jun. 2, 2015, U.S. Pat. No. 9,941,479, Tetradentate Cyclometalated Platinum Complexes Containing 9,10-Dihydroacridine and Its Analogues, Guijie Li, Jian Li, Zhi-Qiang Zhu.
U.S. Appl. No. 15/947,092, filed Apr. 6, 2018, Tetradentate Cyclometalated Platinum Complexes Containing 9,10-Dihydroacridine and Its Analgoues, Guijie Li, Jian Li, Zhi-Qiang Zhu.
U.S. Appl. No. 14/809,981, filed Jul. 27, 2015, U.S. Pat. No. 9,818,959, Metal-Assisted Delayed Fluorescent Emitters Containing Tridentated Ligands, Guijie Li, Jian Li.
U.S. Appl. No. 15/711,525, filed Sep. 21, 2017, Metal-Assisted Delayed Fluorescent Emitters Containing Tridentate Ligands, Guijie Li, Jian Li.
U.S. Appl. No. 14/805,691, filed Jul. 22, 2015, U.S. Pat. No. 9,923,155, Tetradentate Platinum (II) Complexes Cyclometalated With Functionalized Phenyl Carbene Ligands and Their Analogues, Jian Li, Zhi-Qiang Zhu.
U.S. Appl. No. 15/925,084, filed Mar. 19, 2018, Tetradentate Platinum (II) Complexes Cyclometalated With Functionalized Phenyl Carbene Ligands and Their Analogues, Jian Li, Zhi-Qiang Zhu.
U.S. Appl. No. 62/040,133, filed Aug. 21, 2014, Efficient Cyclometalated Platinum Complexes for Displays and Lighting Applications, Jian Li.
U.S. Appl. No. 14/937,318, filed Nov. 10, 2015, US-2016-0133862-A1, Tetradentate Metal Complexes With Carbon Group Bridging Ligands, Guijie Li, Jian Li.

(56) References Cited

OTHER PUBLICATIONS

U.S. Appl. No. 15/168,942, filed May 31, 2016, U.S. Pat. No. 9,879,039, Tetradentate and Octahedral Metal Complexes Containing Naphthyridinocarbazole and Its Analogues, Guijie Li, Jian Li.

U.S. Appl. No. 15/354,280, filed Nov. 17, 2016, U.S. Pat. No. 9,617,291, Tetradentate and Octahedral Metal Complexes Containing Naphthyridinocarbazole and Its Analogues, Guijie Li, Jian Li.

U.S. Appl. No. 15/882,267, filed Jan. 29, 2018, Tetradentate and Octahedral Metal Complexes Containing Naphthyridinocarbazole and its Analgoues, Guijie Li, Jian Li.

U.S. Appl. No. 15/168,910, filed May 31, 2016, U.S. Pat. No. 9,711,739, Tetradentate Metal Complexes Containing Indoloacridine and Its Analogues, Jian Li.

U.S. Appl. No. 15/651,972, filed Jul. 17, 2017, US-2018-0006246-A1, Tetradentate Metal Complexes Containing Indoloacridine and its Analogues, Jian Li.

U.S. Appl. No. 15/228,401, filed Aug. 4, 2016, US-2017-0040555-A1, Tetradentate Platinum (II) and Palladium (II) Complexes, Devices, and Uses Thereof, Jian Li, Zhi-Qiang Zhu.

U.S. Appl. No. 15/625,082, filed Jun. 16, 2017, US-2018-0053904-A1, Tetradentate Platinum (II) and Palladium (II) Complexes and Octahedral Iridium Complexes Employing Azepine Functional Groups and Their Analogues, Jian Li, Zhi-Qiang Zhu.

U.S. Appl. No. 62/377,884, filed Aug. 22, 2016, Tetradentate Platinum (II) and Palladium (II) Complexes Employing Azepine Functional Group and Their Analogues, Jian Li, Zhi-Qiang Zhu.

U.S. Appl. No. 62/451,574, filed Jan. 27, 2017, Metal-Assisted Delayed Fluorescent Emitters Employing Pyrido-Pyrrolo-Acridine and Analogues, Jian Li, Yunlong Ji.

U.S. Appl. No. 15/487,476, filed Apr. 14, 2017, US-2017-0301871-A1, OLED With Multi-Emissive Material Layer, Jian Li.

U.S. Appl. No. 62/508,560, filed May 19, 2017, Metal-Assisted Delayed Fluorescent Emitters Employing Benzo-Imidazo-Phenanthridine and Analogues, Jian Li, Yunlong Ji.

U.S. Appl. No. 62/508,849, filed May 19, 2017, Tetradentate Platinum and Palladium Complexes Based on Biscarbazole and Analogues, Jian Li, Zhiqiang Zhu.

U.S. Appl. No. 62/573,596, filed Oct. 17, 2017, Hole-Blocking Materials for Organic Light Emitting Diodes, Jian Li.

U.S. Appl. No. 62/573,472, filed Oct. 17, 2017, Phosphorescent Excimers With Preferred Molecular Orientation as Monochromatic Emitters for Display and Lighting Applications, Jian Li.

U.S. Appl. No. 62/573,639, filed Oct. 17, 2017, Phosphorescent Excimers With Preferred Molecular Orientation as Monochromatic Emitters for Display and Lighting Applications, Jian Li.

U.S. Appl. No. 62/573,462, filed Oct. 17, 2017, Single-Doped White OLED With Extraction Layer Doped With Down-Conversion Red Phosphors, Jian Li.

U.S. Appl. No. 15/845,575, filed Dec. 18, 2017, Organic Light Emitting Diode With Split Emissive Layer, Jian Li, Kody George Klimes.

U.S. Appl. No. 16/031,517, filed Jul. 10, 2018, Tetradentate Plantinum and Palladium Complex Emitters Containing Phenyl-Pyrazole and its Analogues, Guijie Li, Jian Li.

U.S. Appl. No. 16/043,908, filed Jul. 24, 2018, Tetradentate Metal Complexes with Carbon Group Bridging Ligands, Guijie Li, Jian Li.

U.S. Appl. No. 15/983,680, filed Aug. 18, 2018, Metal-Assisted Delayed Fluorescent Emtters Employing Benzo-Imidazo-Phenanthridine and Analogues, Jian Li, Yunlong Ji, Linyu Cao.

U.S. Appl. No. 15/984,036, filed May 18, 2018, Tetradentate Platinum And Palladium Complexes Based On Biscarbazole and Analogues, Jian Li, Zhiqiang Zhu.

PHOSPHORESCENT TETRADENTATE METAL COMPLEXES HAVING MODIFIED EMISSION SPECTRA

CROSS-REFERENCE TO RELATED APPLICATION

This application is a continuation of to U.S. application Ser. No. 14/300,832 filed on Jun. 10, 2014, entitled "PHOSPHORESCENT TETRADENTATE METAL COMPLEXES HAVING MODIFIED EMISSION SPECTRA," now U.S. Pat. No. 9,673,409, which claims priority to U.S. application Ser. No. 61/833,091 filed on Jun. 10, 2013, entitled "PHOSPHORESCENT TETRADENTATE METAL COMPLEXES HAVING MODIFIED EMISSION SPECTRA," which are incorporated by reference herein in their entirety.

TECHNICAL FIELD

The present disclosure relates to multidentate metal complexes and compositions including the same that can be useful as emitters in display and lighting applications, as well as devices including these complexes and compositions.

BACKGROUND

Compounds capable of absorbing and/or emitting light can be ideally suited for use in a wide variety of optical and electro-optical devices, including, for example, photo-absorbing devices such as solar- and photo-sensitive devices, organic light emitting diodes (OLEDs), photo-emitting devices, or devices capable of both photo-absorption and emission and as markers for bio-applications.

FIG. 1 depicts an example of an OLED. As shown in FIG. 1, OLED 100 may include a layer of indium tin oxide (ITO) as an anode 102, a layer of hole-transporting materials (HTL) 104, a layer of emissive materials (EML) 106 including emitter(s) and host(s), a layer of electron-transporting materials (ETL) 108, and a metal cathode layer 110 on substrate 112. The emission color of OLED 100 may be determined by the emission energy (optical energy gap) of the emitter(s) in the layer of emissive materials.

Much research has been devoted to the discovery and optimization of organic and organometallic materials for using in optical and electro-optical devices such as OLEDs. Generally, research in this area aims to accomplish a number of goals, including improvements in absorption and emission efficiency, as well as improvements in processing ability. Despite significant advances in research devoted to optical and electro-optical materials, many currently available materials exhibit a number of disadvantages, including poor processing ability, inefficient emission or absorption, and less than ideal stability, among others. Thus, a need exists for new materials which exhibit improved performance in optical emitting and absorbing applications.

SUMMARY

Multidentate metal complexes and compositions including one or more of the complexes can be useful as emitters in organic light emitting diodes (OLEDs), displays and lighting applications, and photovoltaic devices.

Generally, a chemical structural change will affect the electronic structure of the compounds, which thereby affects the optical properties of the compounds (e.g., emission and absorption spectra). Thus, the compounds described herein can be tailored or tuned to a particular emission or absorption energy. In some aspects, the optical properties of the compounds disclosed herein can be tuned by varying the structure of the ligand surrounding the metal center. For example, compounds having a ligand with electron donating substituents or electron withdrawing substituents generally exhibit different optical properties, including different emission and absorption spectra.

As described herein, the emission spectra of the compounds can be modified by altering one or more of the substitution groups of the ancillary ligands. In some aspects, one or more features of an emission spectrum becomes narrower or broader, exhibits a blue shift or a red shift, or a combination thereof.

In a first general aspect, a composition includes one or more compounds of the formulas:

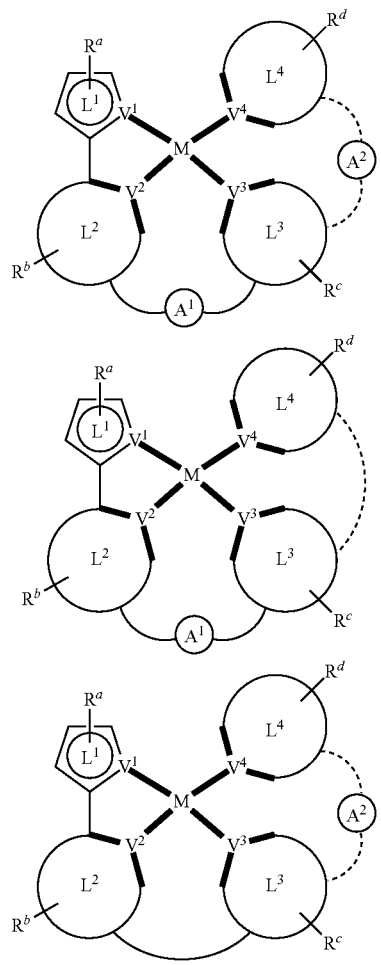

wherein, for each of the one or more compounds:

($L^1$^$L^2$) represents an emitting portion of the compound, ($L^3$^$L^4$) represents an ancillary portion of the compound, $L^1$, $L^2$ and $L^3$ each independently represents a substituted or unsubstituted aromatic ring, heterocyclic group, carbene group, or N-heterocyclic carbene, $L^4$ represents a substituted or unsubstituted aromatic ring, heterocyclic group, carbene group, N-heterocyclic carbene, chlorine (Cl), fluorine (F), nitrile, substituted alkyl, substituted alkenyl, or $C_3$-$C_6$ alkynyl, $L^1$ and $L^2$ are linked directly, $L^2$ and $L^3$ are linked directly or through a linking atom $A^1$, wherein $A^1$ represents oxygen (O), sulfur (S), nitrogen (N), carbon (C), phosphorous (P), silicon (Si), or boron (B), $L^3$ and $L^4$ are unlinked, linked directly, or, when $L^4$ represents a substituted or unsubstituted aromatic ring, heterocyclic group, carbene group, or N-heterocyclic carbene, linked through a linking atom $A^2$, wherein $A^2$ represents oxygen (O), sulfur (S), nitrogen (N), carbon (C), phosphorous (P), silicon (Si), or boron (B), $V^1$, $V^2$, $V^3$ and $V^4$ represent coordinated atoms of $L^1$, $L^2$, $L^3$ or $L^4$, respectively, wherein $V^1$, $V^2$, $V^3$ and $V^4$ each independently represents nitrogen (N), carbon (C), phosphorous (P), boron (B), or silicon (Si), M represents platinum (Pt), gold (Au), iridium (Ir), rhodium (Rh), ruthenium (Ru), iron (Fe), cobalt (Co), nickel (Ni), copper (Cu), zinc (Zn), silver (Ag), mercury (Hg), cadmium (Cd), or zirconium (Zr), and $R^a$, $R^b$, $R^c$ and $R^d$ each independently represents mono-, di-, tri-, or tetra-substitution, and each independently represents one or more of deuterium, a halogen atom, a hydroxyl group, a thiol group, a nitro group, a cyano group, a substituted or unsubstituted alkyl group, a substituted or unsubstituted haloalkyl group, a substituted or unsubstituted aralkyl group, a substituted or unsubstituted alkenyl group, a substituted or unsubstituted alkynyl group, a substituted or unsubstituted aryl group, a substituted or unsubstituted amino group, a substituted or unsubstituted mono- or dialkylamino group, a substituted or unsubstituted mono- or diarylamino group, a substituted or unsubstituted alkoxy group, a substituted or unsubstituted aryloxy group, a substituted or unsubstituted heteroaryl group, an alkoxycarbonyl group, an acyloxy group, an acylamino group, an alkoxycarbonylamino group, an aryloxycarbonylamino group, a sulfonylamino group, a sulfamoyl group, a carbamoyl group, an alkylthio group, a sulfinyl group, a ureido group, a phosphoramide group, a mercapto group, a sulfo group, a carboxyl group, a hydrazino group, a substituted silyl group, a polymeric group, or a combination thereof.

Implementations may include one or more of the following features. In some cases, for example, the the polymeric group includes a polyalkylene, a polyether, or a polyester. In certain cases, for at least one of the compounds, at least one of the following is true: $R^a$ is fused to $L^1$, $R^b$ is fused to $L^2$, $R^c$ is fused to $L^3$, and $R^d$ is fused to $L^4$. The composition, or a compound of the composition, may have a neutral charge.

In a second general aspect, a light emitting device includes the composition of the first general aspect. In some cases, the light emitting device includes an organic light emitting diode. In certain cases, the light emitting device is an organic light emitting diode.

In a third general aspect, a device includes the composition of the first general aspect or the light emitting device of the second general aspect. The device may include, for example, a full color display, a photovoltaic device, or a luminescent or phosphorescent display device. In some cases, the device includes an organic light emitting diode. In certain cases, the device is an organic light emitting diode.

Additional aspects will be set forth in the description which follows. Advantages will be realized and attained by means of the elements and combinations particularly pointed out in the claims. It is to be understood that both the foregoing general description and the following detailed description are exemplary and explanatory only and are not restrictive.

DETAILED DESCRIPTION

Figure 1:
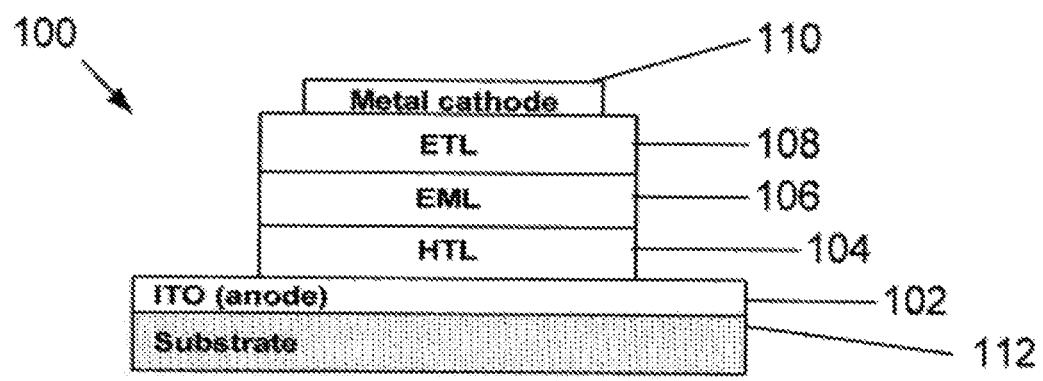
FIG. 1 depicts an organic light emitting device (OLED).

The present disclosure can be understood more readily by reference to the following detailed description and the Examples included therein. Before the present compounds, devices, and/or methods are disclosed and described, it is to be understood that they are not limited to specific synthetic methods unless otherwise specified, or to particular reagents unless otherwise specified, as such can, of course, vary. It is also to be understood that the terminology used herein is for the purpose of describing particular aspects only and is not intended to be limiting. Although any methods and materials similar or equivalent to those described herein can be used in the practice or testing, example methods and materials are now described.

As used in the specification and the appended claims, the singular forms "a", "an", and "the" include plural referents unless the context clearly dictates otherwise. Thus, for example, reference to "a component" includes mixtures of two or more components.

In some aspects, ranges expressed herein as from "about" one particular value to "about" another particular value include from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "optional" or "optionally" means that the subsequently described event or circumstance can or cannot occur, and that the description includes instances where said event or circumstance occurs and instances where it does not.

Disclosed are the components to be used to prepare the compositions described herein as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions. Thus, if there are a variety of additional steps that can be performed it is understood that each of these additional steps can be performed with any specific embodiment or combination of embodiments of the methods.

As referred to herein, a linking atom can connect two groups such as, for example, a N and C group. The linking atom can optionally, if valency permits, have other chemical moieties attached. For example, in one aspect, an oxygen would not have any other chemical groups attached as the valency is satisfied once it is bonded to two atom (e.g., N or C). In contrast, when carbon is the linking atom, two additional chemical moieties can be attached to the carbon. Suitable chemical moieties include, but are not limited to, hydrogen, hydroxyl, alkyl, alkoxy, =O, halogen, nitro, amine, amide, thiol, aryl, heteroaryl, cycloalkyl, and heterocyclyl.

The term "cyclic structure" or the like terms used herein refer to any cyclic chemical structure which includes, but is not limited to, aryl, heteroaryl, cycloalkyl, cycloalkenyl, heterocyclyl, carbene, and N-heterocyclic carbene.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound (e.g., a compound that does not spontaneously undergo transformation such as by rearrangement, cyclization, elimination, etc.). It is also contemplated that, in certain aspects, unless expressly indicated to the contrary, individual substituents can be further optionally substituted (i.e., further substituted or unsubstituted).

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, optionally substituted alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms.

Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The terms "amine" or "amino" as used herein are represented by the formula $NA^1A^2A^3$, where $A^1$, $A^2$, and $A^3$ are independently hydrogen, optionally substituted alkyl, cycloalkyl, alkenyl, cycloalkenyl, alkynyl, cycloalkynyl, aryl, or heteroaryl group as described herein.

The terms "alkoxy" and "alkoxyl" as used herein to refer to an alkyl or cycloalkyl group bonded through an ether linkage; that is, an "alkoxy" group can be defined as —$OA^1$ where $A^1$ is alkyl or cycloalkyl as defined above. "Alkoxy" also includes polymers of alkoxy groups as just described; that is, an alkoxy can be a polyether such as —$OA^1$—$OA^2$ or —$OA^1$—$(OA^2)_a$—$OA^3$, where "a" is an integer of from 1 to 200 and $A^1$, $A^2$, and $A^3$ are each independently alkyl groups, cycloalkyl groups, or a combination thereof.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This can be presumed in structural formulas herein wherein an asymmetric alkene is present, or it can be explicitly indicated by the bond symbol C=C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bond. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The term "alkylamino" as used herein is represented by the formula —NH(-alkyl) where alkyl is as described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl) amino group, hexylamino group, and the like.

The term "dialkylamino" as used herein is represented by the formula —N(-alkyl)$_2$ where alkyl is as described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula —OC(O)A$^1$ or —C(O)OA$^1$, where A$^1$ can be alkyl, cycloalkyl, alkenyl, cycloalkenyl, alkynyl, cycloalkynyl, aryl, or heteroaryl as described herein. The term "polyester" as used herein is represented by the formula -(A$^1$O(O)C-A$^2$-C(O)O)$_a$— or -(A$^1$O(O)C-A$^2$-OC(O))$_a$—, where A$^1$ and A$^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula A$^1$OA$^2$, where A$^1$ and A$^2$ can be, independently, an alkyl, cycloalkyl, alkenyl, cycloalkenyl, alkynyl, cycloalkynyl, aryl, or heteroaryl group described herein. The term "polyether" as used herein is represented by the formula -(A$^1$O-A$^2$O)$_a$—, where A$^1$ and A$^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The term "polymeric" includes polyalkylene, polyether, polyester, and other groups with repeating units, such as, but not limited to —(CH$_2$O)$_n$—CH$_3$, —(CH$_2$CH$_2$O)$_n$—CH$_3$, —[CH$_2$CH(CH$_3$)]$_n$—CH$_3$, —[CH$_2$CH(COOCH$_3$)]$_n$—CH$_3$, —[CH$_2$CH(COO CH$_2$CH$_3$)]$_n$—CH$_3$, and —[CH$_2$CH(COO$^t$Bu)]$_n$—CH$_3$, where n is an integer (e.g., n>1 or n>2).

The term "halide" as used herein refers to the halogens fluorine, chlorine, bromine, and iodine.

The term "heterocyclyl," as used herein refers to single and multi-cyclic non-aromatic ring systems and "heteroaryl" as used herein refers to single and multi-cyclic aromatic ring systems: in which at least one of the ring members is other than carbon. The term includes azetidine, dioxane, furan, imidazole, isothiazole, isoxazole, morpholine, oxazole, oxazole, including, 1,2,3-oxadiazole, 1,2,5-oxadiazole and 1,3,4-oxadiazole, piperazine, piperidine, pyrazine, pyrazole, pyridazine, pyridine, pyrimidine, pyrrole, pyrrolidine, tetrahydrofuran, tetrahydropyran, tetrazine, including 1,2,4,5-tetrazine, tetrazole, including 1,2,3,4-tetrazole and 1,2,4,5-tetrazole, thiadiazole, including, 1,2,3-thiadiazole, 1,2,5-thiadiazole, and 1,3,4-thiadiazole, thiazole, thiophene, triazine, including 1,3,5-triazine and 1,2,4-triazine, triazole, including, 1,2,3-triazole, 1,3,4-triazole, and the like.

The term "hydroxyl" as used herein is represented by the formula —OH.

The term "ketone" as used herein is represented by the formula A$^1$C(O)A$^2$, where A$^1$ and A$^2$ can be, independently, an alkyl, cycloalkyl, alkenyl, cycloalkenyl, alkynyl, cycloalkynyl, aryl, or heteroaryl group as described herein.

The term "azide" as used herein is represented by the formula —N$_3$.

The term "nitro" as used herein is represented by the formula —NO$_2$.

The term "nitrile" as used herein is represented by the formula —CN.

The term "silyl" as used herein is represented by the formula —SiA$^1$A$^2$A$^3$, where A$^1$, A$^2$, and A$^3$ can be, independently, hydrogen or an alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —S(O)A$^1$, —S(O)$_2$A$^1$, —OS(O)$_2$A$^1$, or —OS(O)$_2$OA$^1$, where A$^1$ can be hydrogen or an alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula —S(O)$_2$A$^1$, where A$^1$ can be hydrogen or an alkyl, cycloalkyl, alkenyl, cycloalkenyl, alkynyl, cycloalkynyl, aryl, or heteroaryl group as described herein. The term "sulfone" as used herein is represented by the formula A$^1$S(O)$_2$A$^2$, where A$^1$ and A$^2$ can be, independently, an alkyl, cycloalkyl, alkenylcycloalkenyl, alkynyl, cycloalkynyl, aryl, or heteroaryl group as described herein. The term "sulfoxide" as used herein is represented by the formula A$^1$S(O)A$^2$, where A$^1$ and A$^2$ can be, independently, an alkyl, cycloalkyl, alkenyl, cycloalkenyl, alkynyl, cycloalkynyl, aryl, or heteroaryl group as described herein.

The term "thiol" as used herein is represented by the formula —SH.

"R$^1$," "R$^2$," "R$^3$," "R$^n$," where n is an integer, as used herein can, independently, possess one or more of the groups listed above. For example, if R$^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

Compounds described herein may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. In is also contemplated that, in certain aspects, unless expressly indicated to the contrary, individual substituents can be further optionally substituted (i.e., further substituted or unsubstituted).

A structure of a compound may be represented by a formula:

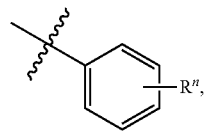

which is understood to be equivalent to a formula:

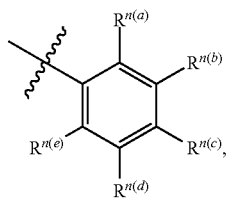

where n is typically an integer. That is, R" is understood to represent five independent substituents, $R^{n(a)}$, $R^{n(b)}$, $R^{n(c)}$, $R^{n(d)}$, $R^{n(e)}$. By "independent substituents," it is meant that each R substituent can be independently defined. For example, if in one instance R"(a) is halogen, then $R^{n(b)}$ is not necessarily halogen in that instance.

Several references to R, $R^1$, $R^2$, $R^3$, $R^4$, $R^5$, $R^6$, etc. are made in chemical structures and moieties disclosed and described herein. Any description of $R^1$, $R^2$, $R^3$, $R^4$, $R^5$, $R^6$, etc. in the specification is applicable to any structure or moiety reciting $R^1$, $R^2$, $R^3$, $R^4$, $R^5$, $R^6$, etc. respectively, unless otherwise noted.

Multidentate (e.g., tetradentate) cyclometalated complexes are described herein. In some cases, such complexes can be incorporated with heptacyclic or higher order materials. In another aspect, such complexes can be useful, for example, in displays and lighting applications.

"Compound" and "complex" are used interchangeably herein. A "composition" includes one or more compounds.

In various aspects, the compounds disclosed herein can include one or more of platinum (Pt) complexes, palladium (Pd) complexes, gold (Au) complexes, iridium (Ir) complexes, rhodium (Rh) complexes, ruthenium (Ru) complexes, iron (Fe) complexes, cobalt (Co) complexes, nickel (Ni) complexes, copper (Cu) complexes, zinc (Zn) complexes, silver (Ag) complexes, mercury (Hg) complexes, cadmium (Cd) complexes, zirconium (Zr) complexes, or other metal complexes not specifically recited herein which are capable of emitting light and are thus useful as an emissive materials in devices.

In one aspect, the present application discloses platinum (Pt), palladium (Pd), gold (Au), iridium (Ir), rhodium (Rh), ruthenium (Ru), iron (Fe), cobalt (Co), nickel (Ni), copper (Cu), zinc (Zn), silver (Ag), mercury (Hg), cadmium (Cd), and/or zirconium (Zr) complexes that can emit electromagnetic radiation. In another aspect, the emission of the complexes can be tuned (e.g. from ultraviolet to near-infrared), by, for example, modifying the ligand structure. In another aspect, the complexes are emissive over a majority of the visible spectrum. In some examples, the complexes can emit light over a range of from about 400 nm to about 700 nm. In another aspect, the complexes have improved stability and efficiency over traditional emission complexes. In yet another aspect, the complexes can be useful as luminescent labels in, for example, bio-applications, anti-cancer agents, or a combination thereof. In another aspect, the complexes can be useful in light emitting devices, such as, for example, emitters in organic light emitting diodes (OLEDs), compact fluorescent lamps (CFLs), light emitting diodes (LEDs), incandescent lamps, and combinations thereof. For any of the formulas herein, R, $R^a$, $R^b$, $R^c$, $R^d$, $R^1$, $R^2$, $R^3$, $R^4$, $R^5$, $R^6$, $R^7$, $R^8$, $R^9$, $R^{10}$, $R^{11}$, $R^{12}$, $R^{13}$ and $R^{14}$ can, in various aspects, each independently represent a deuterium, a halogen atom, a hydroxyl group, a thiol group, a nitro group, a cyano group, a substituted or unsubstituted alkyl group, a substituted or unsubstituted haloalkyl group, a substituted or unsubstituted aralkyl group, a substituted or unsubstituted alkenyl group, a substituted or unsubstituted alkynyl group, a substituted or unsubstituted aryl group, an amino group, a mono- or dialkylamino group, a mono- or diarylamino group, a substituted or unsubstituted alkoxy group, a substituted or unsubstituted aryloxy group, a substituted or unsubstituted heteroaryl group, an alkoxycarbonyl group, an acyloxy group, an acylamino group, an alkoxycarbonylamino group, an aryloxycarbonylamino group, a sulfonylamino group, a sulfamoyl group, a carbamoyl group, an alkylthio group, a sulfinyl group, a ureido group, a phosphoramide group, a mercapto group, a sulfo group, a carboxyl group, a hydrazine group, a substituted silyl group, a polymeric group, or a combination thereof. In some cases, any two or more substitutions can represent the same or a different group. Further, the letters "m", "n", "o", "p", "q" and "r" can, in various aspects, represent an integer of 0, 1, 2, 3, 4, 5, 6, 7, 8, 9, 10, 11, 12 . . . etc., and any two or more letters can represent the same or a different number.

As described herein, a composition may include one or more compounds of the formulas:

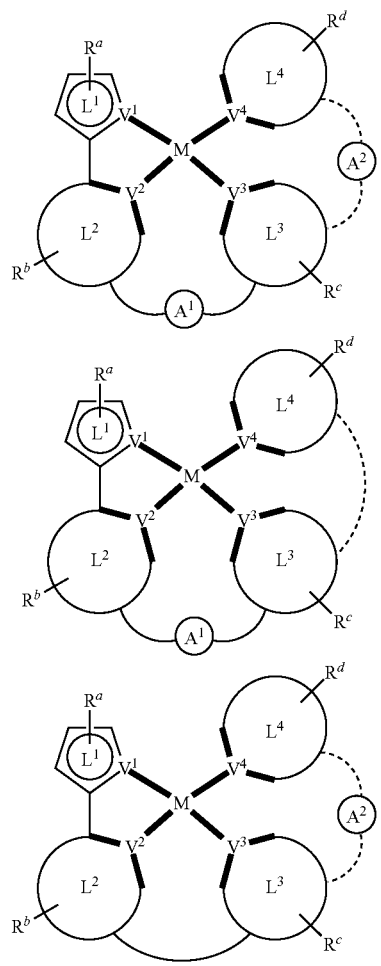

wherein, for each of the one or more compounds:
($L^1 \frown L^2$) represents an emitting portion of the compound,
($L^3 \frown L^4$) represents an ancillary portion of the compound,
$L^1$, $L^2$ and $L^3$ each independently represents a substituted or unsubstituted aromatic ring, heterocyclic group, carbene group, or N-heterocyclic carbene, L⁴ represents a substituted or unsubstituted aromatic ring, heterocyclic group, carbene group, N-heterocyclic carbene, chlorine (Cl), fluorine (F), nitrile, substituted alkyl, substituted alkenyl, or $C_3$-$C_6$ alkynyl, L¹ and L² are linked directly, L² and L³ are linked directly or through a linking atom A¹, wherein A¹ represents oxygen (O), sulfur (S), nitrogen (N), carbon (C), phosphorous (P), silicon (Si), or boron (B), L³ and L⁴ are unlinked, linked directly, or, when L⁴ represents a substituted or unsubstituted aromatic ring, heterocyclic group, carbene group, or N-heterocyclic carbene, linked through a linking atom A², wherein A² represents oxygen (O), sulfur (S), nitrogen (N), carbon (C), phosphorous (P), silicon (Si), or boron (B), V¹, V², V³ and V⁴ represent coordinated atoms of L¹, L², L³ or L⁴, respectively, wherein V¹, V², V³ and V⁴ each independently represents nitrogen (N), carbon (C), phosphorous (P), boron (B), or silicon (Si), M represents platinum (Pt), gold (Au), iridium (Ir), rhodium (Rh), ruthenium (Ru), iron (Fe), cobalt (Co), nickel (Ni), copper (Cu), zinc (Zn), silver (Ag), mercury (Hg), cadmium (Cd), or zirconium (Zr), and $R^a$, $R^b$, $R^c$ and $R^d$ each independently represents mono-, di-, tri, or tetra-substitution, and each independently represents one or more of deuterium, a halogen atom, a hydroxyl group, a thiol group, a nitro group, a cyano group, a substituted or unsubstituted alkyl group, a substituted or unsubstituted haloalkyl group, a substituted or unsubstituted aralkyl group, a substituted or unsubstituted alkenyl group, a substituted or unsubstituted alkynyl group, a substituted or unsubstituted aryl group, a substituted or unsubstituted amino group, a substituted or unsubstituted mono- or dialkylamino group, a substituted or unsubstituted mono- or diarylamino group, a substituted or unsubstituted alkoxy group, a substituted or unsubstituted aryloxy group, a substituted or unsubstituted heteroaryl group, an alkoxycarbonyl group, an acyloxy group, an acylamino group, an alkoxycarbonylamino group, an aryloxycarbonylamino group, a sulfonylamino group, a sulfamoyl group, a carbamoyl group, an alkylthio group, a sulfinyl group, a ureido group, a phosphoramide group, a mercapto group, a sulfo group, a carboxyl group, a hydrazino group, a substituted silyl group, a polymeric group, or a combination thereof.

In some cases, one or more of the following is true: $R^a$ is fused to ligand L¹, $R^b$ is fused to ligand L², $R^c$ is fused to ligand L³, and $R^d$ is fused to ligand L⁴. In certain cases, the composition, each compound therein, or both are neutral in charge. In some implementations, "polymeric" includes a polyalkylene, a polyether, a polyester, or a combination thereof.

Generally, a chemical structural change will affect the electronic structure of the compounds, which thereby affects the optical properties of the compounds (e.g., emission and absorption spectra). Thus, the compounds described herein can be tailored or tuned to a particular emission or absorption energy. In some aspects, the optical properties of the compounds disclosed herein can be tuned by varying the structure of the ligand surrounding the metal center. For example, compounds having a ligand with electron donating substituents or electron withdrawing substituents generally exhibit different optical properties, including different emission and absorption spectra.

As described herein, the emission spectra of the compounds can be modified by altering one or more of the substitution groups of the ancillary ligands. In some aspects, one or more features of an emission spectrum become narrower or broader, exhibits a blue shift or a red shift, or a combination thereof.

For the formulas disclosed herein,

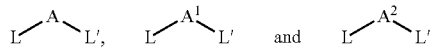

are intended to illustrate that L and L' are either linked directly or that L and L' are linked by a linkage group A, A¹, or A², wherein each of the linkage groups may independently represent oxygen (O), sulfur (S), nitrogen (N), phosphorous (P), carbon (C), silicon (Si), or boron (B). In some cases,

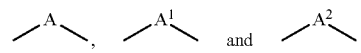

may each independently represent the following:

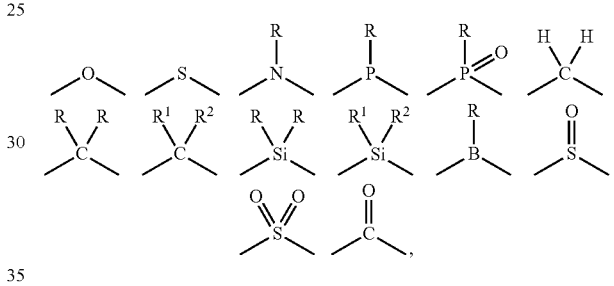

R, R¹, and R² each independently represents deuterium, a halogen atom, a hydroxyl group, a thiol group, a nitro group, a cyano group, a substituted or unsubstituted alkyl group, a substituted or unsubstituted haloalkyl group, a substituted or unsubstituted aralkyl group, a substituted or unsubstituted alkenyl group, a substituted or unsubstituted alkynyl group, a substituted or unsubstituted aryl group, an amino group, a mono- or dialkylamino group, a mono- or diarylamino group, a substituted or unsubstituted alkoxy group, a substituted or unsubstituted aryloxy group, a substituted or unsubstituted heteroaryl group, an alkoxycarbonyl group, an acyloxy group, an acylamino group, an alkoxycarbonylamino group, an aryloxycarbonylamino group, a sulfonylamino group, a sulfamoyl group, a carbamoyl group, an alkylthio group, a sulfinyl group, a ureido group, a phosphoramide group, a mercapto group, a sulfo group, a carboxyl group, a hydrazino group, a substituted silyl group, a polymeric group, or a combination thereof.

V¹, V², V³ and V⁴ represent atoms coordinated to L¹, L², L³ or L⁴, where V¹, V², V³, and V⁴ may each independently represent nitrogen (N), carbon (C), phosphorous (P), boron (B), or silicon (Si).

For any of the formulas disclosed herein,

may each independently represent the following:

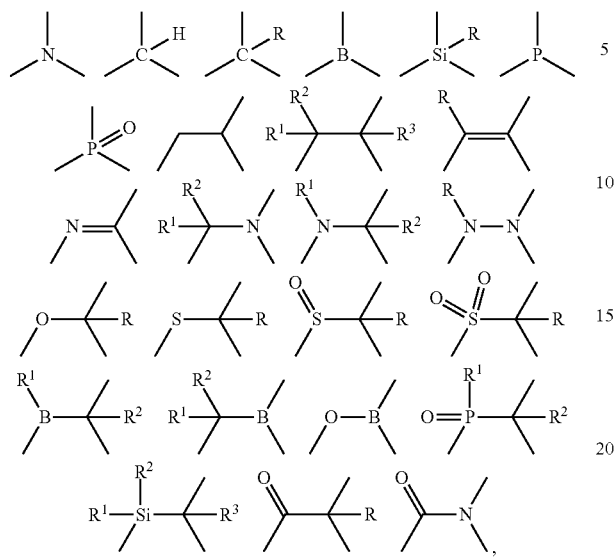

where R, $R^1$, $R^2$ and $R^3$ each independently represents deuterium, a halogen atom, a hydroxyl group, a thiol group, a nitro group, a cyano group, a substituted or unsubstituted alkyl group, a substituted or unsubstituted haloalkyl group, a substituted or unsubstituted aralkyl group, a substituted or unsubstituted alkenyl group, a substituted or unsubstituted alkynyl group, a substituted or unsubstituted aryl group, an amino group, a mono- or dialkylamino group, a mono- or diarylamino group, a substituted or unsubstituted alkoxy group, a substituted or unsubstituted aryloxy group, a substituted or unsubstituted heteroaryl group, an alkoxycarbonyl group, an acyloxy group, an acylamino group, an alkoxycarbonylamino group, an aryloxycarbonylamino group, a sulfonylamino group, a sulfamoyl group, a carbamoyl group, an alkylthio group, a sulfinyl group, a ureido group, a phosphoramide group, a mercapto group, a sulfo group, a carboxyl group, a hydrazino group, a substituted silyl group, a polymeric group, or a combination thereof.

For any of the formulas disclosed herein,

may represent the following:

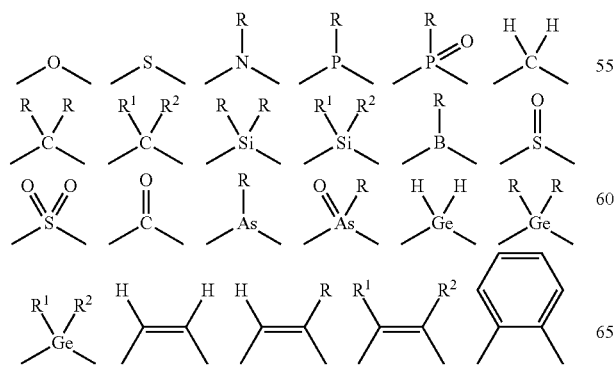

-continued

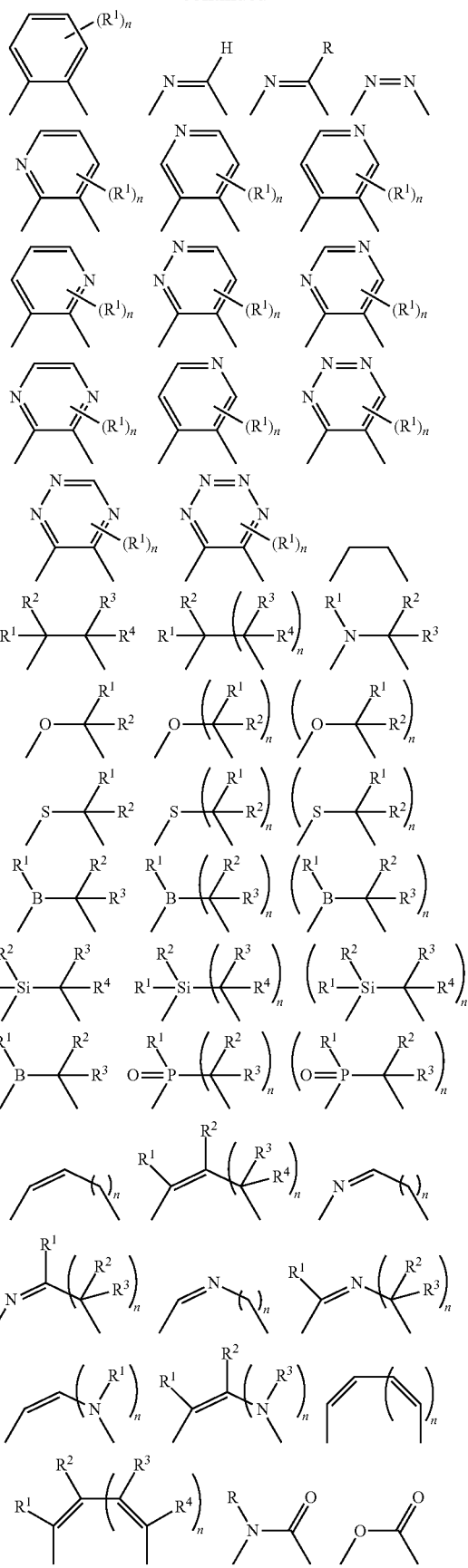

-continued

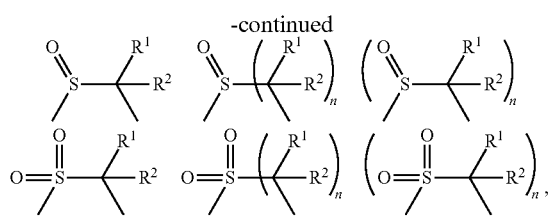

where:

n is an integer, and $R^1$, $R^2$, $R^3$, and $R^4$ each independently represents deuterium, a halogen atom, a hydroxyl group, a thiol group, a nitro group, a cyano group, a substituted or unsubstituted alkyl group, a substituted or unsubstituted haloalkyl group, a substituted or unsubstituted aralkyl group, a substituted or unsubstituted alkenyl group, a substituted or unsubstituted alkynyl group, a substituted or unsubstituted aryl group, an amino group, a mono- or dialkylamino group, a mono- or diarylamino group, a substituted or unsubstituted alkoxy group, a substituted or unsubstituted aryloxy group, a substituted or unsubstituted heteroaryl group, an alkoxycarbonyl group, an acyloxy group, an acylamino group, an alkoxycarbonylamino group, an aryloxycarbonylamino group, a sulfonylamino group, a sulfamoyl group, a carbamoyl group, an alkylthio group, a sulfinyl group, a ureido group, a phosphoramide group, a mercapto group, a sulfo group, a carboxyl group, a hydrazino group, a substituted silyl group, a polymeric group, or a combination thereof.

For any of the formulas disclosed herein,

may represent the following:

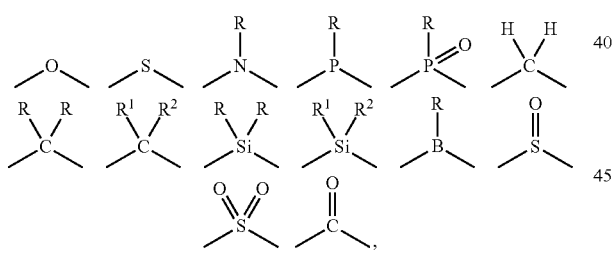

where R, $R^1$ and $R^2$ each independently represents deuterium, a halogen atom, a hydroxyl group, a thiol group, a nitro group, a cyano group, a substituted or unsubstituted alkyl group, a substituted or unsubstituted haloalkyl group, a substituted or unsubstituted aralkyl group, a substituted or unsubstituted alkenyl group, a substituted or unsubstituted alkynyl group, a substituted or unsubstituted aryl group, an amino group, a mono- or dialkylamino group, a mono- or diarylamino group, a substituted or unsubstituted alkoxy group, a substituted or unsubstituted aryloxy group, a substituted or unsubstituted heteroaryl group, an alkoxycarbonyl group, an acyloxy group, an acylamino group, an alkoxycarbonylamino group, an aryloxycarbonylamino group, a sulfonylamino group, a sulfamoyl group, a carbamoyl group, an alkylthio group, a sulfinyl group, a ureido group, a phosphoramide group, a mercapto group, a sulfo group, a carboxyl group, a hydrazino group, a substituted silyl group, a polymeric group, or a combination thereof.

The portion of a tetradentate metal complexes represented as

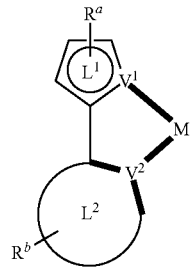

may represent the following:

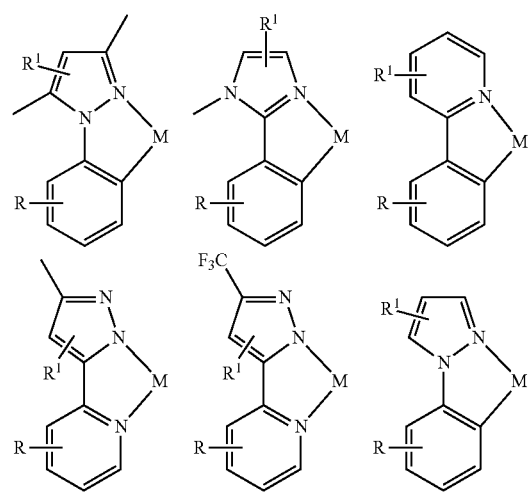

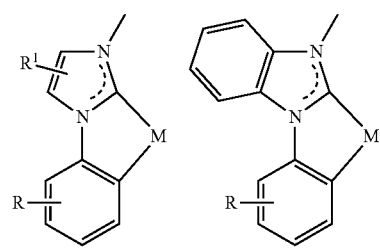

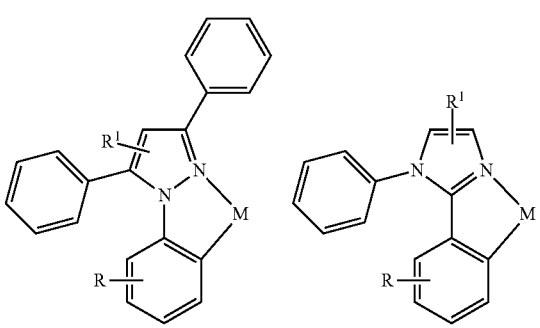

-continued
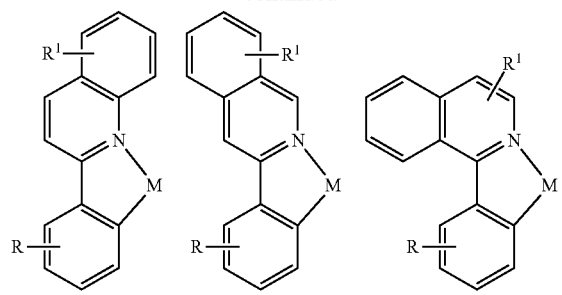
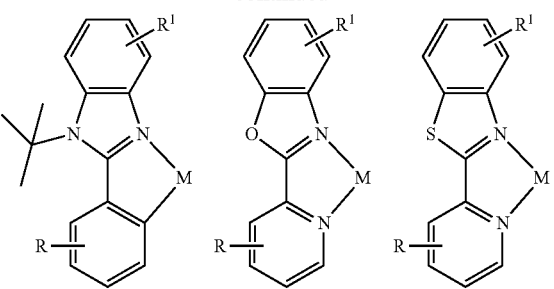
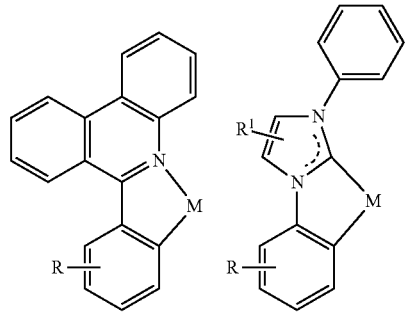
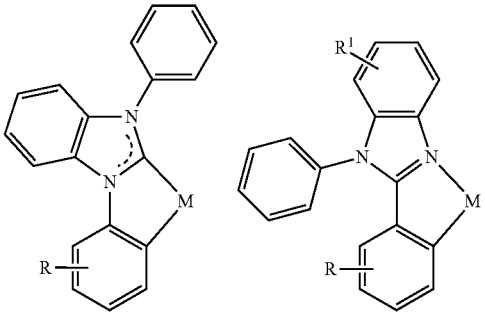
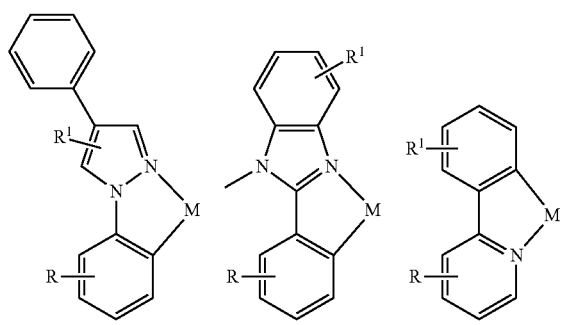
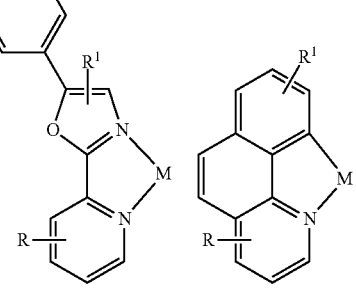
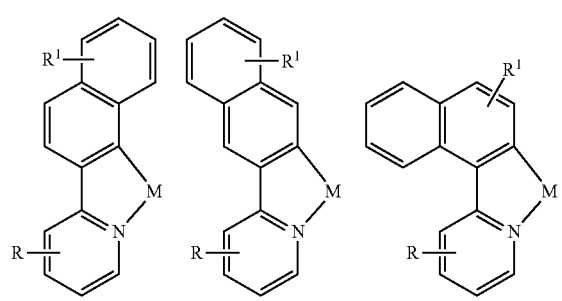
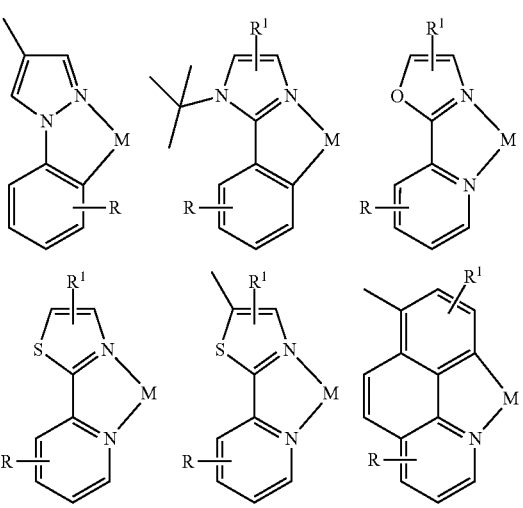
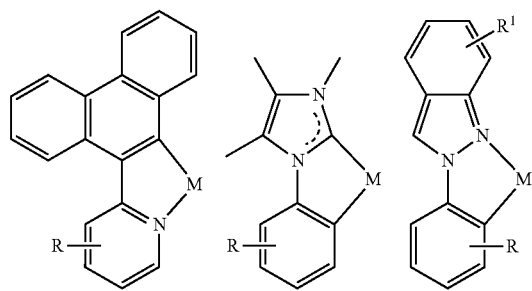

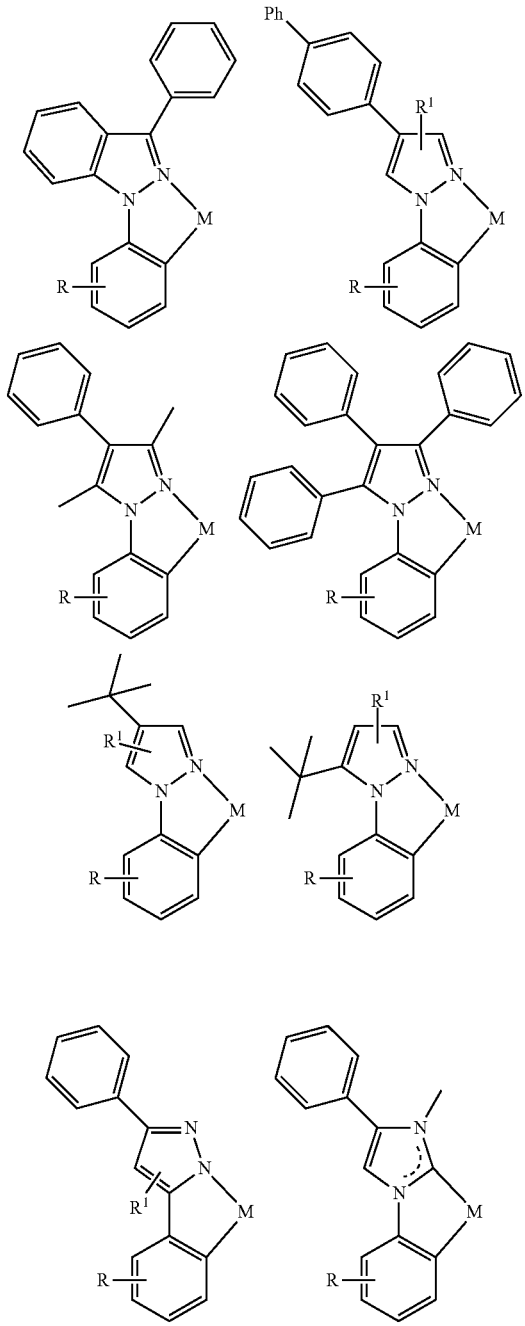
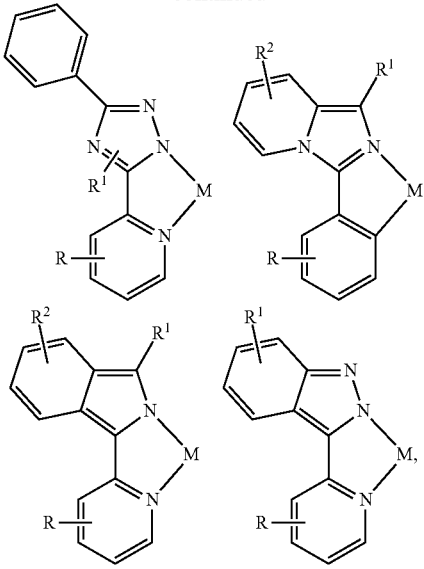

where R, R[1], and R[2] each independently represents mono-, di-, tri, or tetra-substitution, and independently represents deuterium, a halogen atom, a hydroxyl group, a thiol group, a nitro group, a cyano group, a substituted or unsubstituted alkyl group, a substituted or unsubstituted haloalkyl group, a substituted or unsubstituted aralkyl group, a substituted or unsubstituted alkenyl group, a substituted or unsubstituted alkynyl group, a substituted or unsubstituted aryl group, an amino group, a mono- or dialkylamino group, a mono- or diarylamino group, a substituted or unsubstituted alkoxy group, a substituted or unsubstituted aryloxy group, a substituted or unsubstituted heteroaryl group, an alkoxycarbonyl group, an acyloxy group, an acylamino group, an alkoxycarbonylamino group, an aryloxycarbonylamino group, a sulfonylamino group, a sulfamoyl group, a carbamoyl group, an alkylthio group, a sulfinyl group, a ureido group, a phosphoramide group, a mercapto group, a sulfo group, a carboxyl group, a hydrazino group, a substituted silyl group, a polymeric group, or a combination thereof.

For any of the formulas disclosed herein,

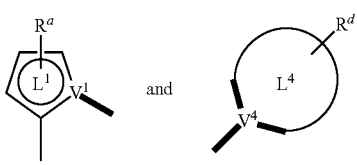

may each independently represent the following:

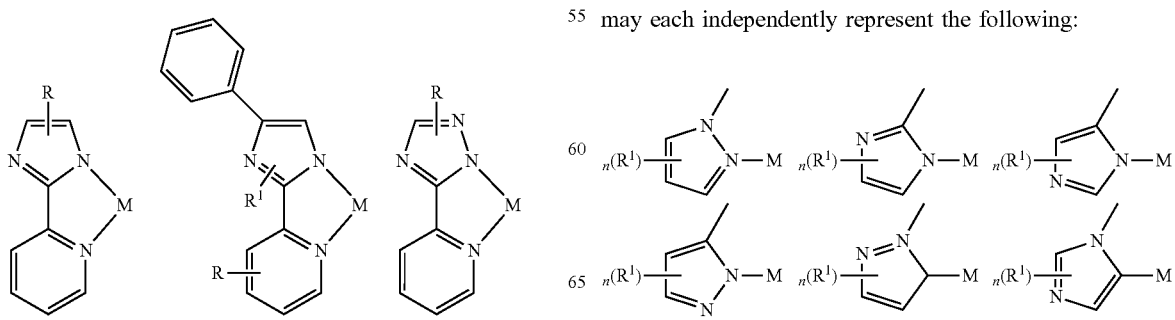

-continued
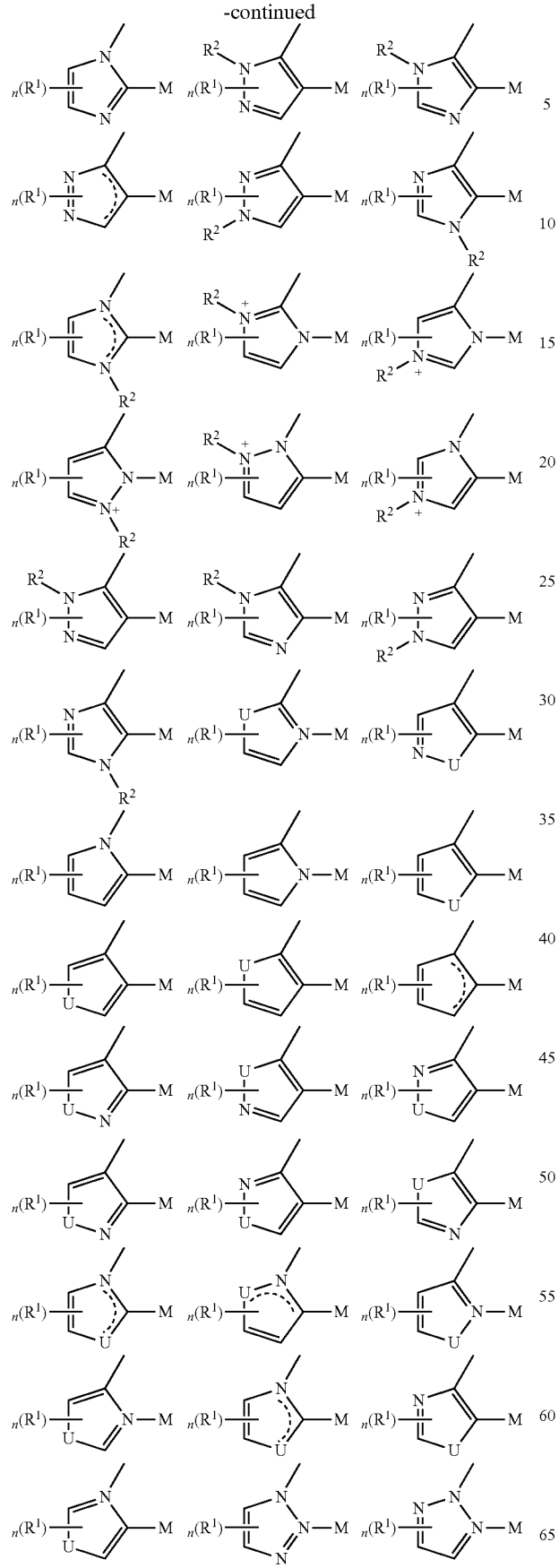
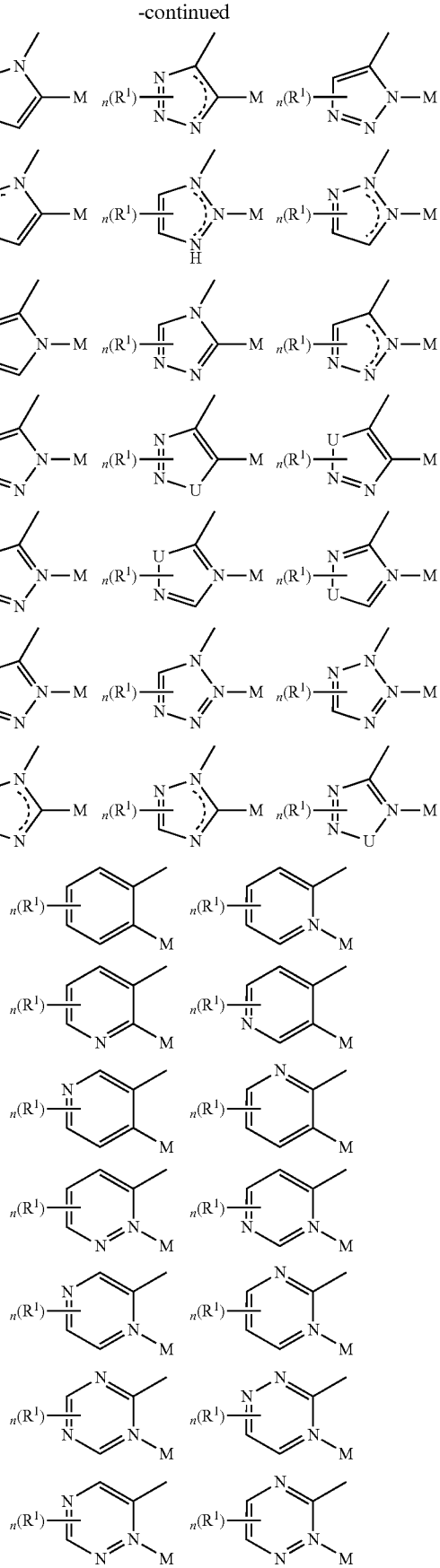

25
-continued

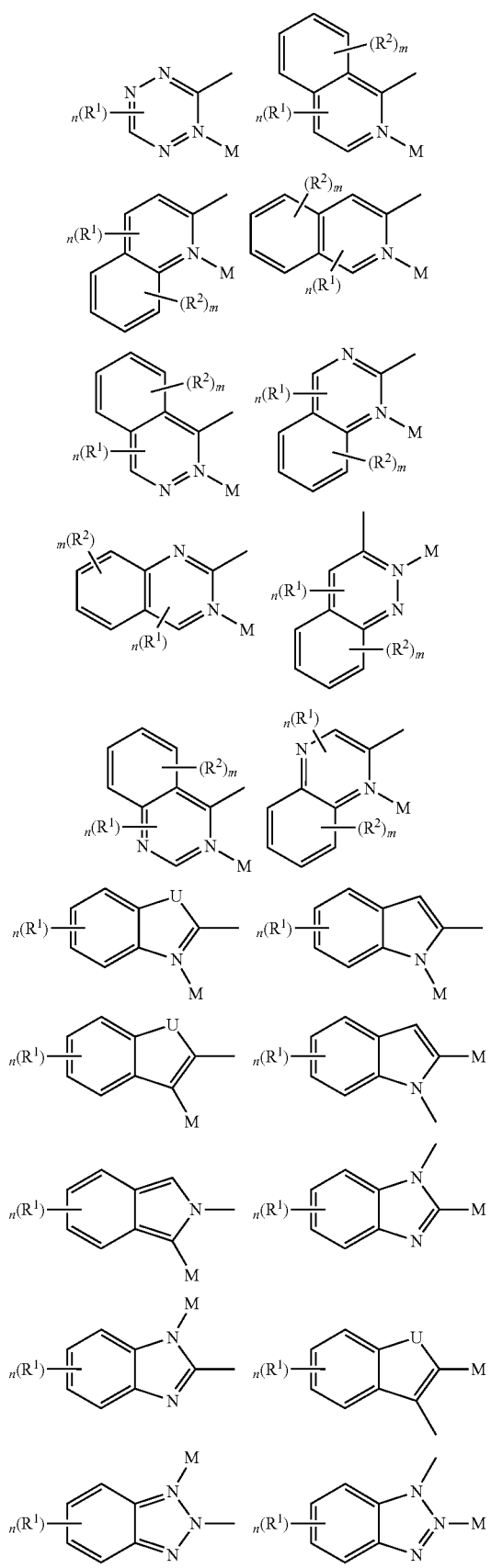

26
-continued

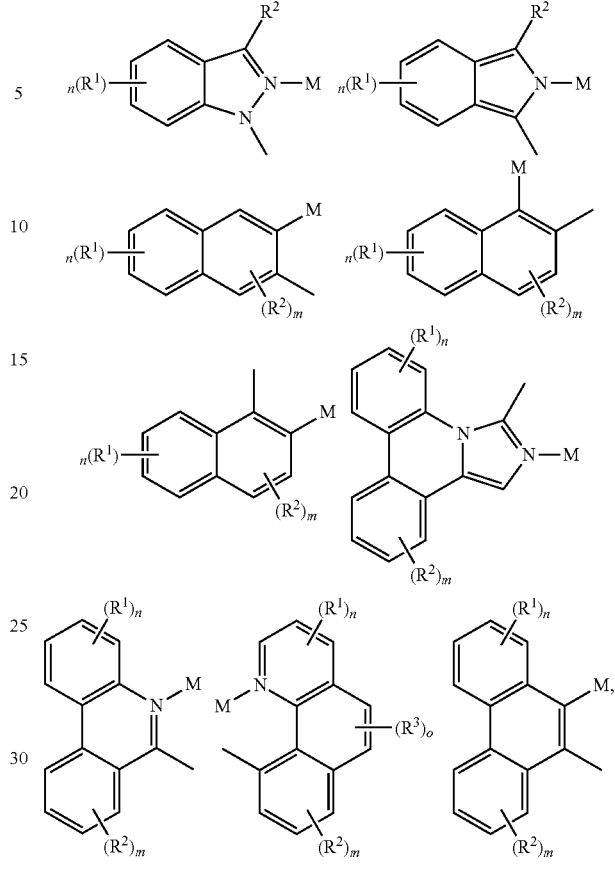

where:

m, n, and o each independently represents an integer from 1 to 4 indicating mono-, di-, tri, or tetra-substitution, and $R^1$ and $R^2$ each independently represents deuterium, a halogen atom, a hydroxyl group, a thiol group, a nitro group, a cyano group, a substituted or unsubstituted alkyl group, a substituted or unsubstituted haloalkyl group, a substituted or unsubstituted aralkyl group, a substituted or unsubstituted alkenyl group, a substituted or unsubstituted alkynyl group, a substituted or unsubstituted aryl group, an amino group, a mono- or dialkylamino group, a mono- or diarylamino group, a substituted or unsubstituted alkoxy group, a substituted or unsubstituted aryloxy group, a substituted or unsubstituted heteroaryl group, an alkoxycarbonyl group, an acyloxy group, an acylamino group, an alkoxycarbonylamino group, an aryloxycarbonylamino group, a sulfonylamino group, a sulfamoyl group, a carbamoyl group, an alkylthio group, a sulfinyl group, a ureido group, a phosphoramide group, a mercapto group, a sulfo group, a carboxyl group, a hydrazino group, a substituted silyl group, a polymeric group, or a combination thereof.

For any of the formulas disclosed herein,

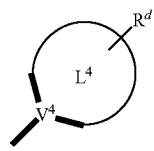

may represent the following:

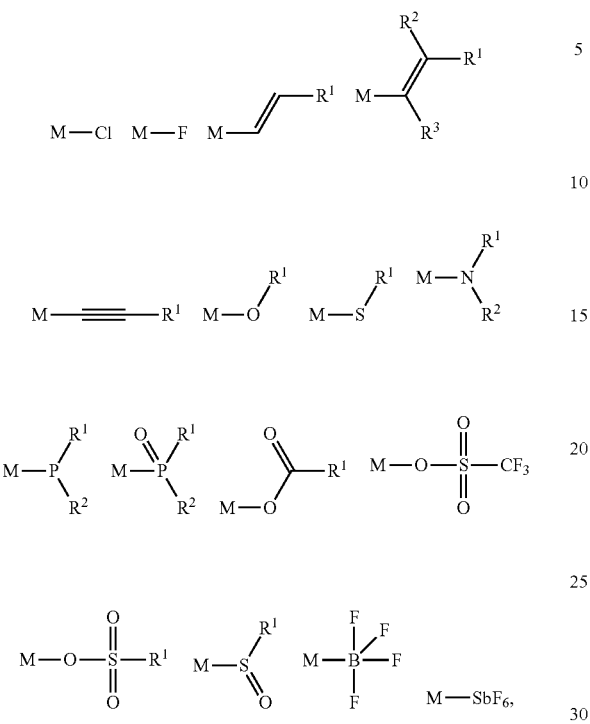

where $R^1$ and $R^2$ each independently represents deuterium, a halogen atom, a hydroxyl group, thiol group, a nitro group, a cyano group, a substituted or unsubstituted alkyl group, a substituted or unsubstituted haloalkyl group, a substituted or unsubstituted aralkyl group, a substituted or unsubstituted alkenyl group, a substituted or unsubstituted alkynyl group, a substituted or unsubstituted aryl group, an amino group, a mono- or dialkylamino group, a mono- or diarylamino group, a substituted or unsubstituted alkoxy group, a substituted or unsubstituted aryloxy group, a substituted or unsubstituted heteroaryl group, an alkoxycarbonyl group, an acyloxy group, an acylamino group, an alkoxycarbonylamino group, an aryloxycarbonylamino group, a sulfonylamino group, a sulfamoyl group, a carbamoyl group, an alkylthio group, a sulfinyl group, a ureido group, a phosphoramide group, a mercapto group, a sulfo group, a carboxyl group, a hydrazino group, a substituted silyl group, a polymeric group, or a combination thereof.

A composition may include one or more of the following:

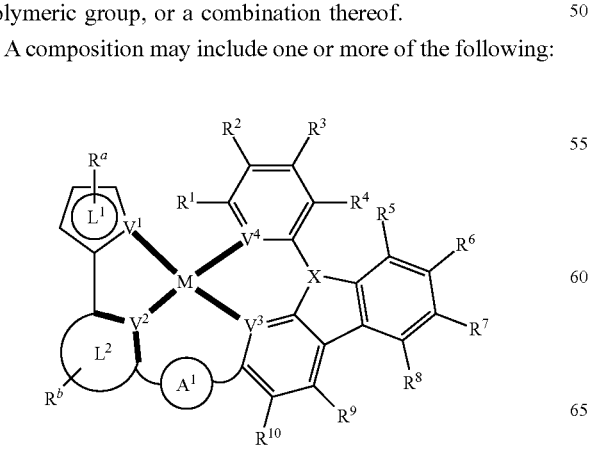

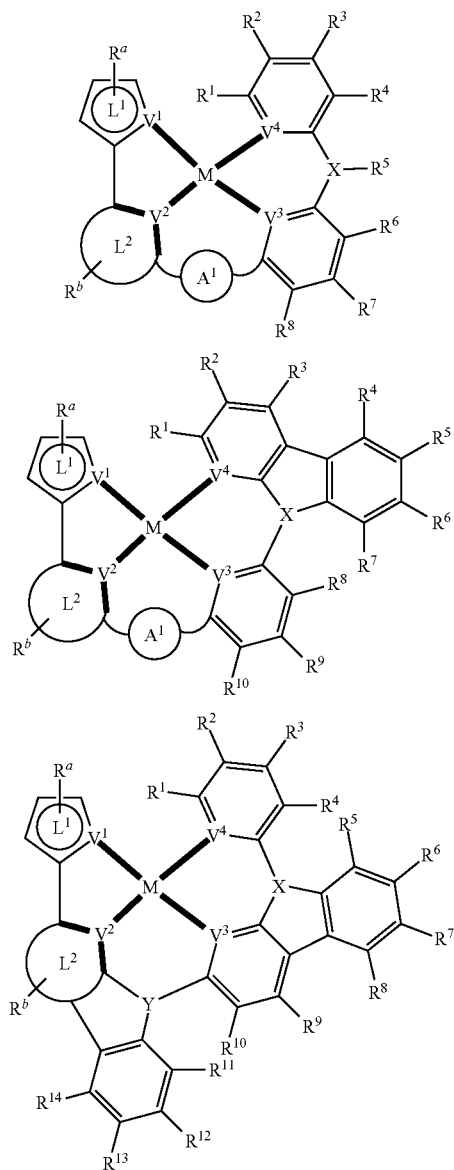

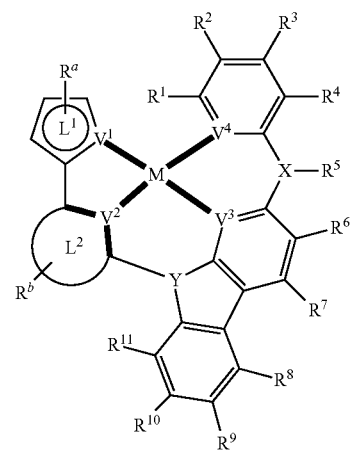

-continued
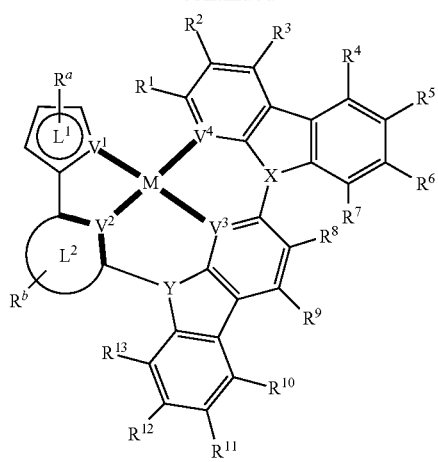
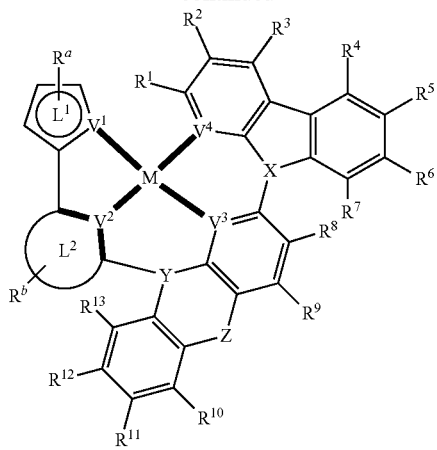
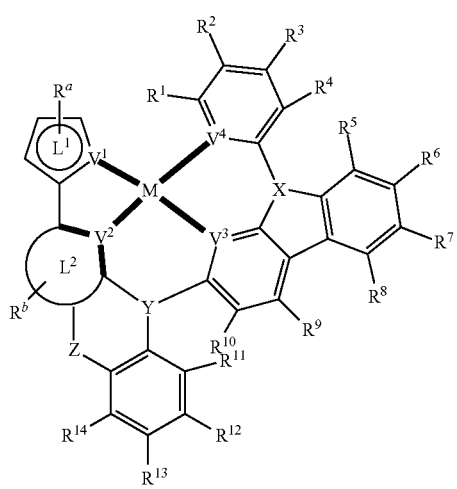
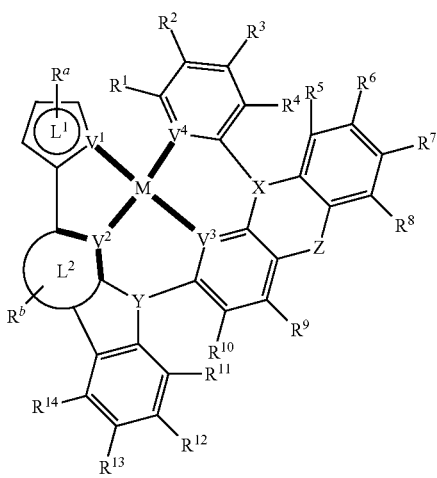
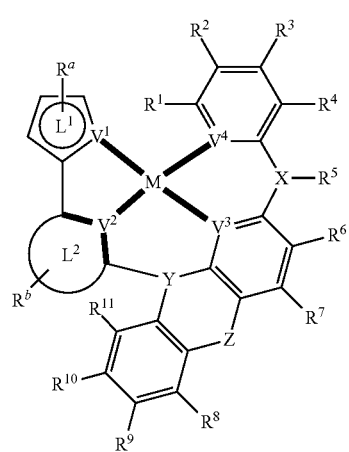
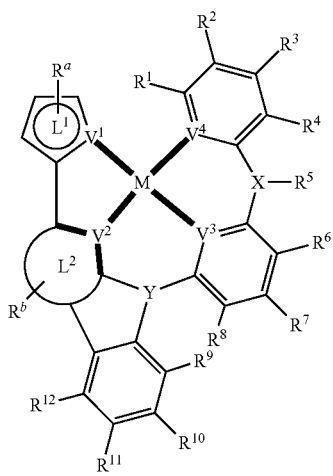

-continued
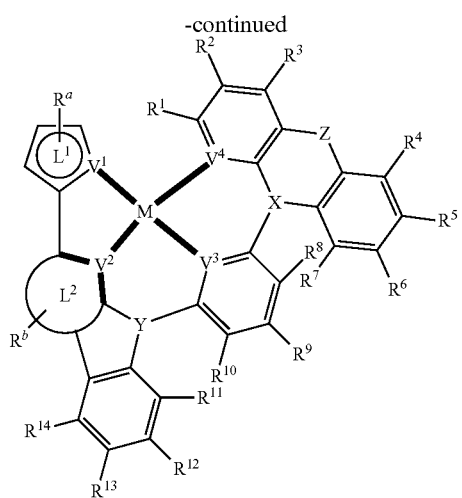
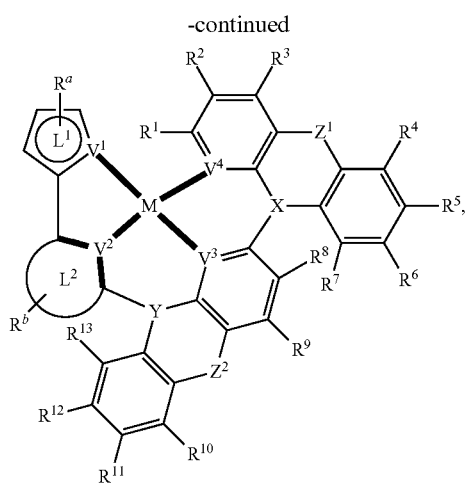
where all symbols have been previously defined.
In some cases, the compositions disclosed herein include one or more of the following:
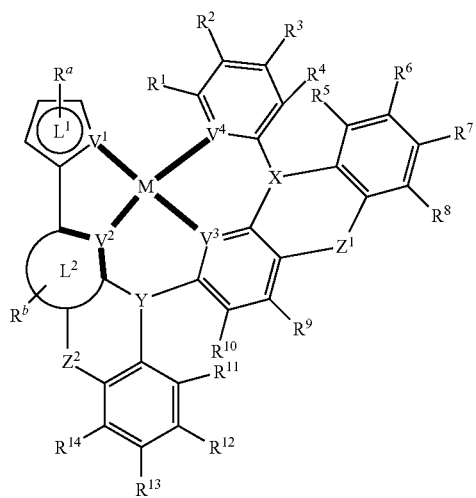
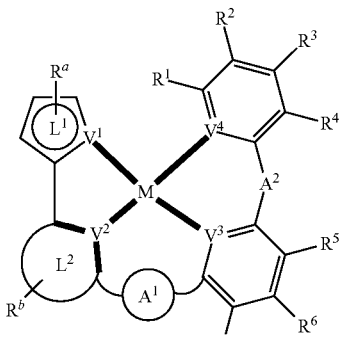
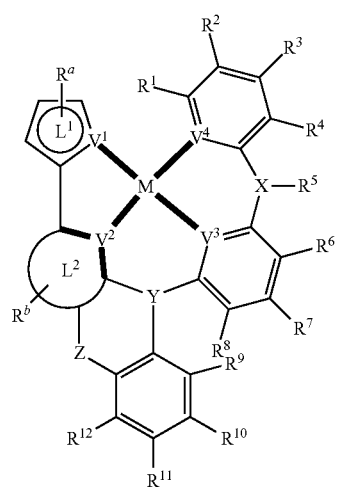
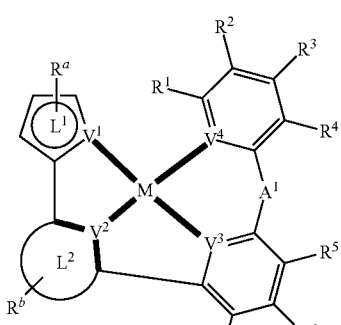
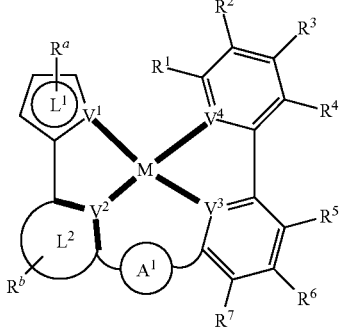

33
-continued
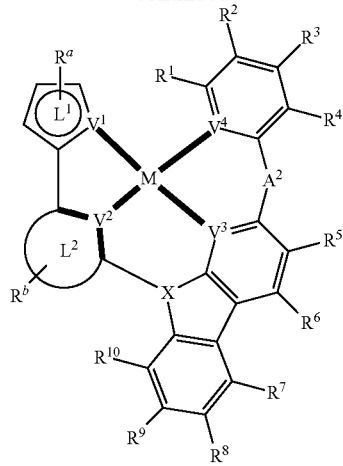
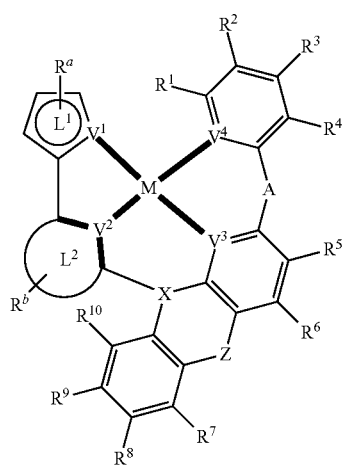
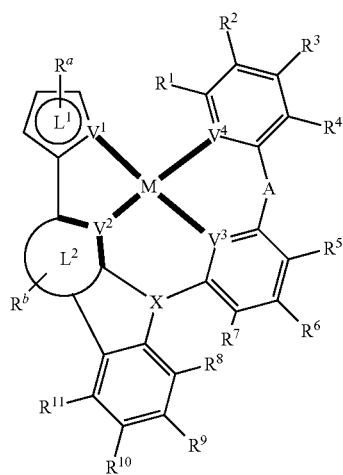
34
-continued
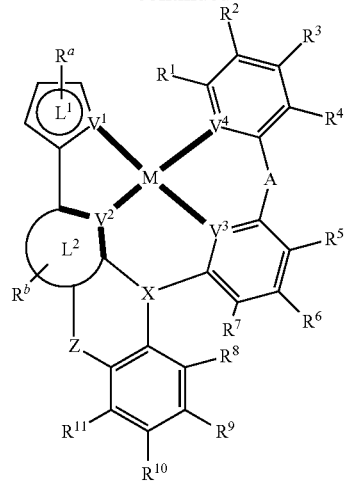
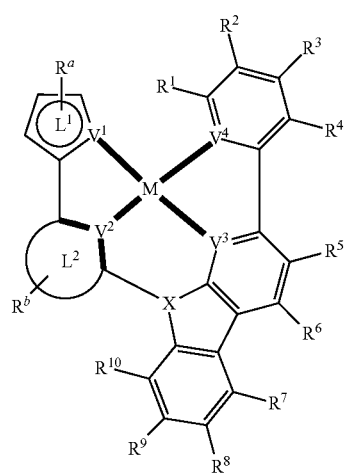
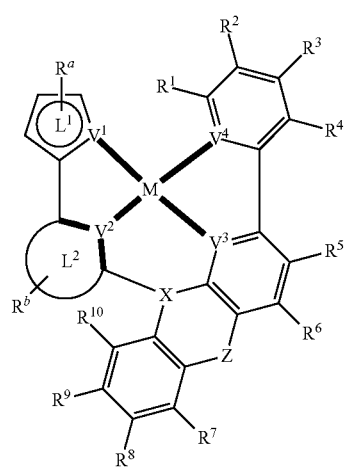

-continued
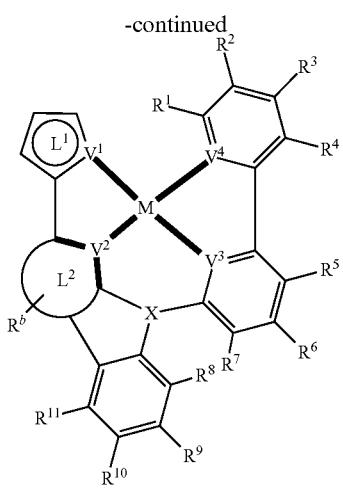
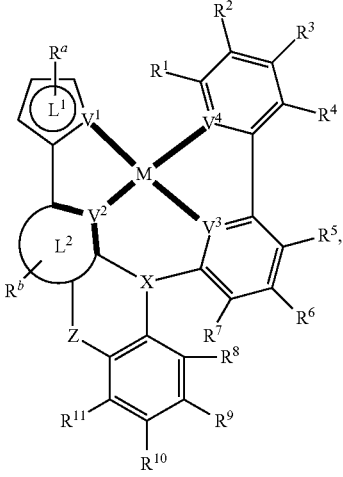
where all symbols have been previously defined.
In certain cases, the compositions disclosed herein include one or more of the following:
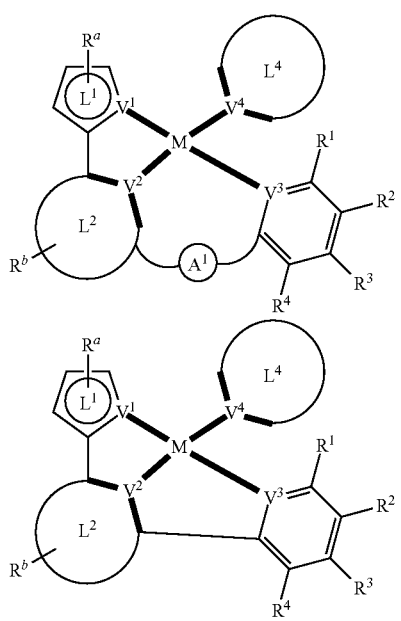
-continued
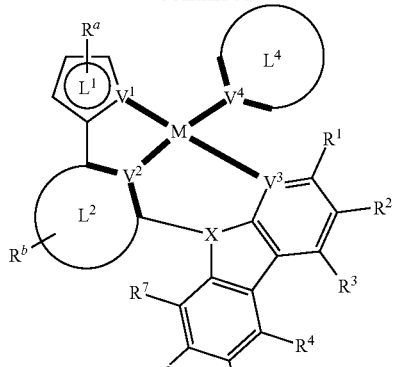
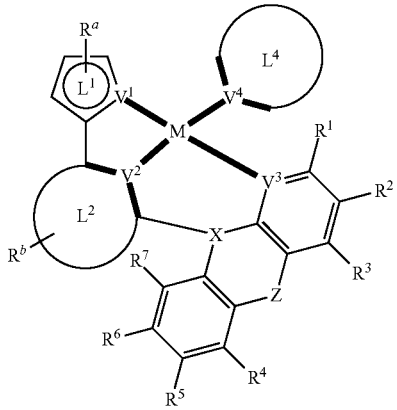
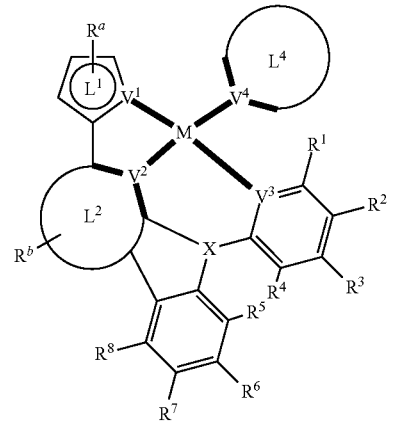
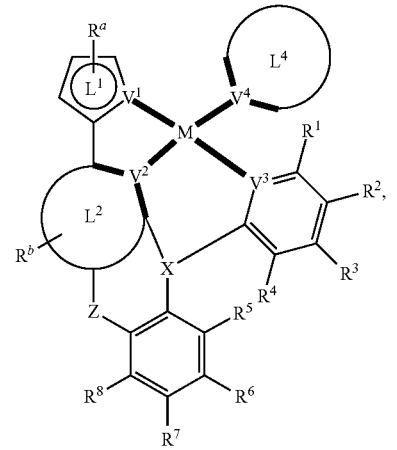
where all symbols have been previously defined.

In certain cases, the compositions disclosed herein include one or more of the following:
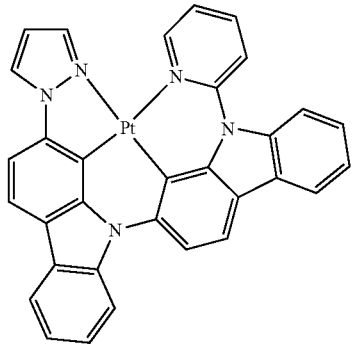
PtN1N
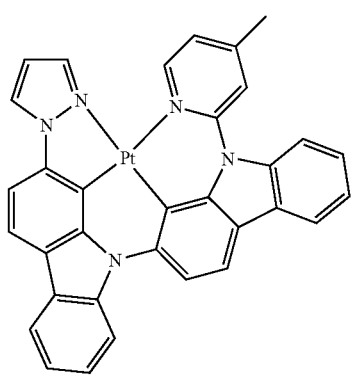
PtN1NMe
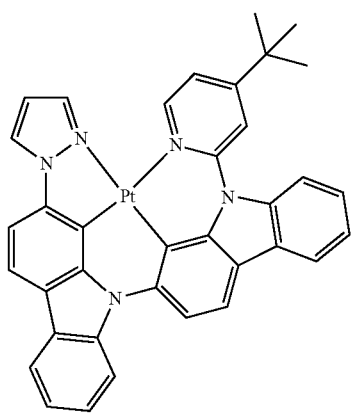
PtN1N-tBu
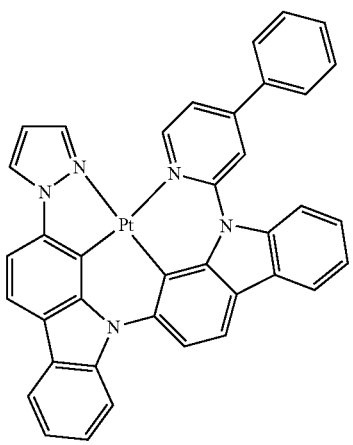
PtN1NPh
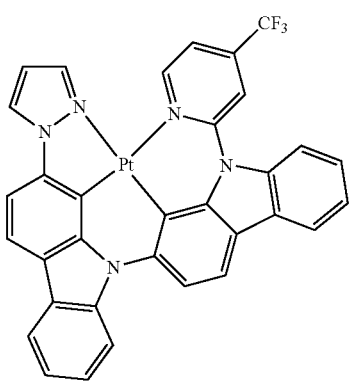
PtN1NCF$_3$
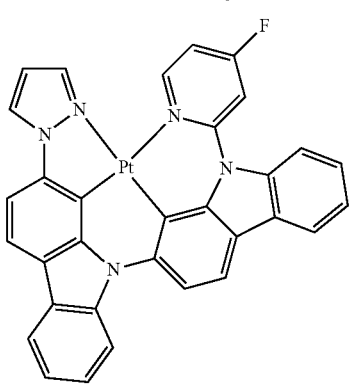
PtN1NF
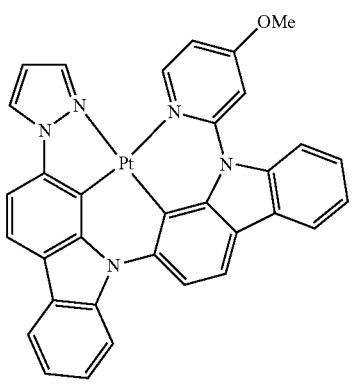
PtN1NOMe

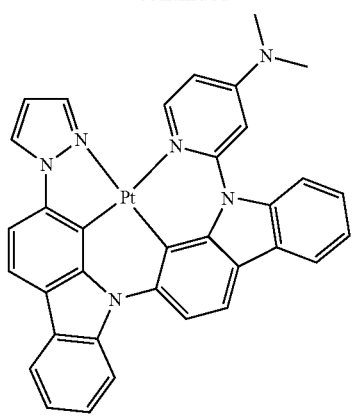
PtN1NNMe2
In certain cases, the compositions disclosed herein include one or more of the following:
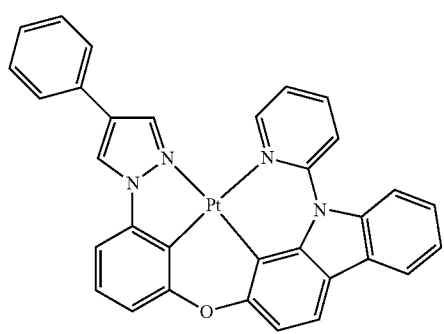
PtON6
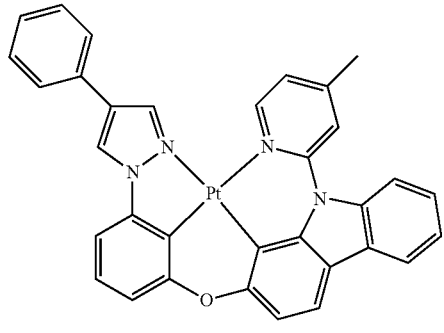
PtON6Me
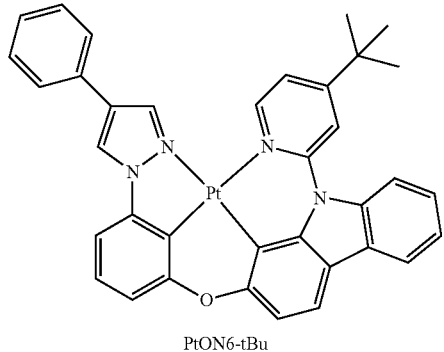
PtON6-tBu
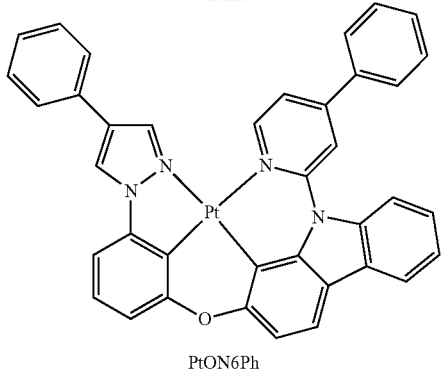
PtON6Ph
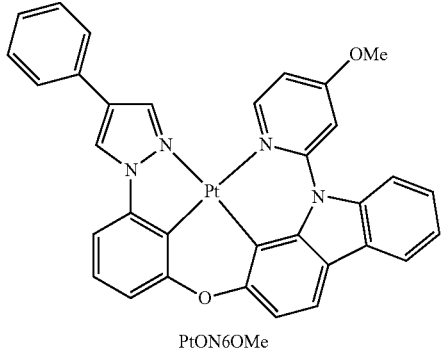
PtON6OMe
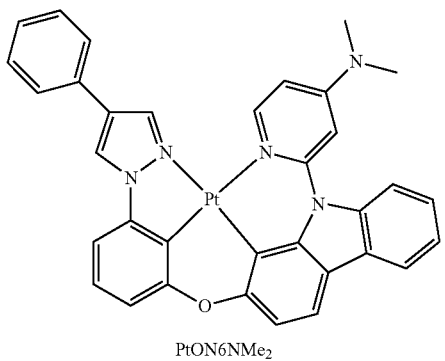
PtON6NMe2
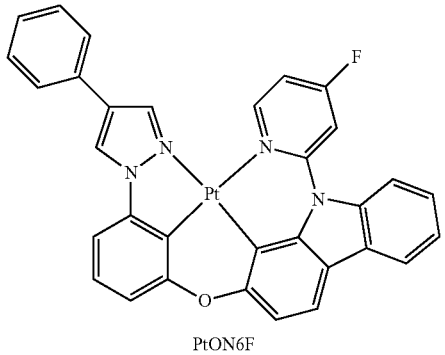
PtON6F -continued
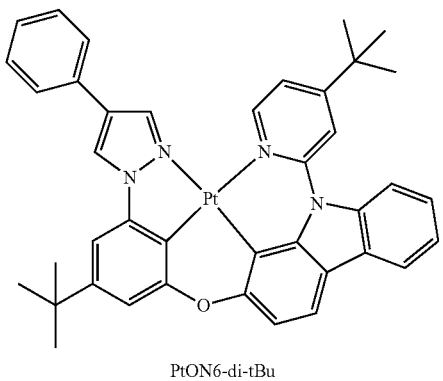
PtON6-di-tBu
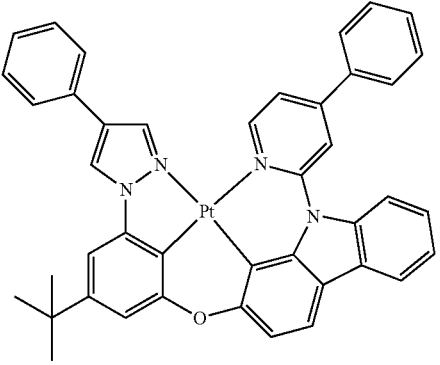
PtON6-ptb
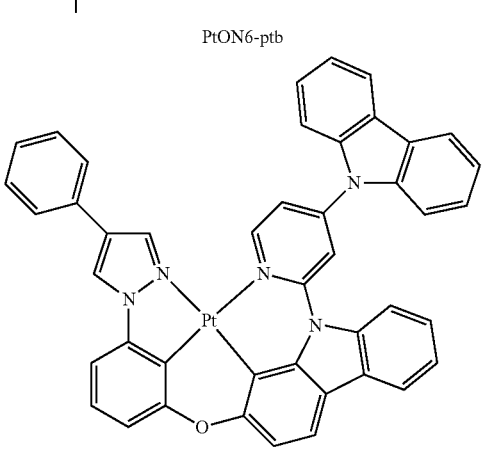
PtON6-Cab
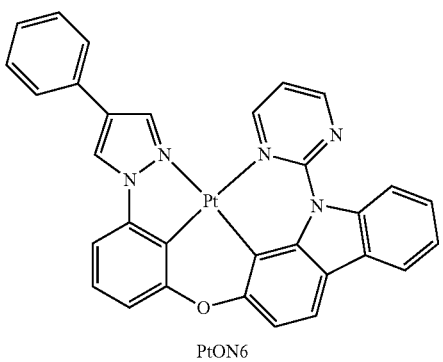
PtON6CF₃
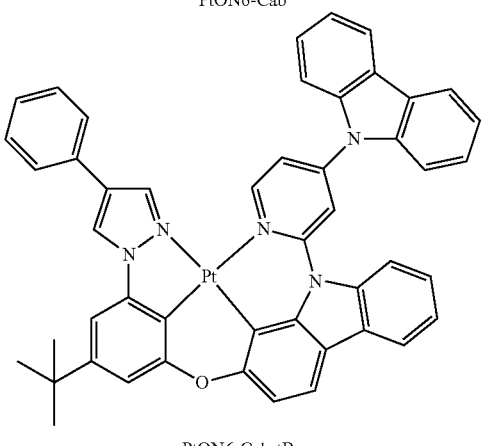
PtON6-Cab-tBu
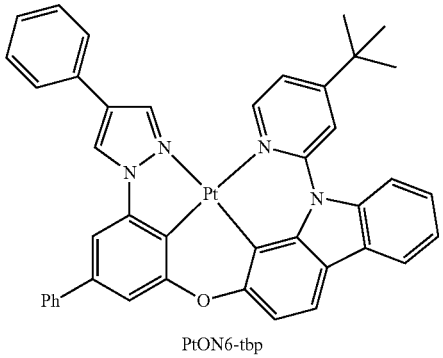
PtON6
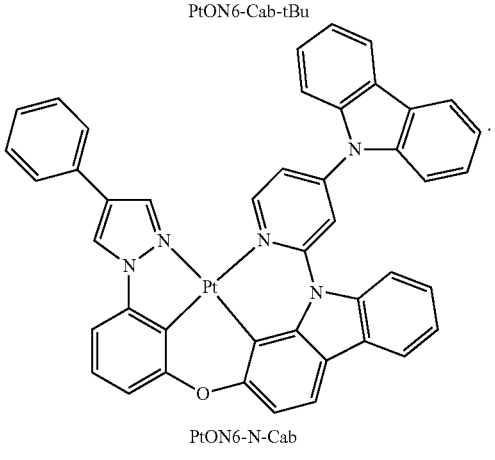
PtON6-N-Cab
PtON6-tbp In still other cases, the compositions disclosed herein include one or more of the following:
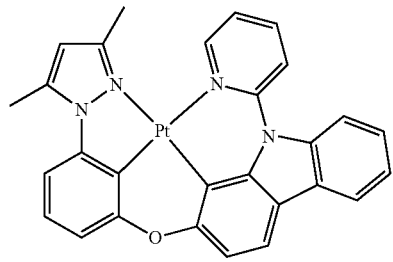
PtON1
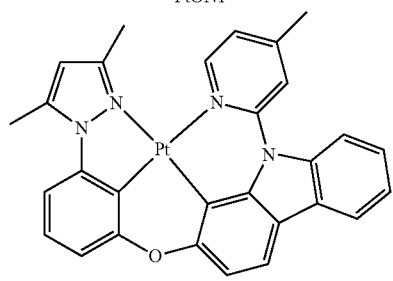
PtON1Me⁴
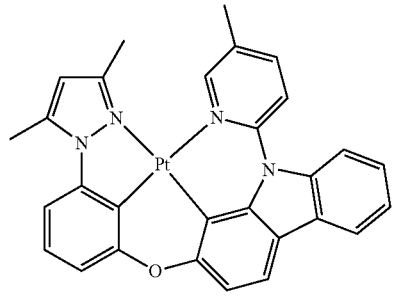
PtON1Me⁵
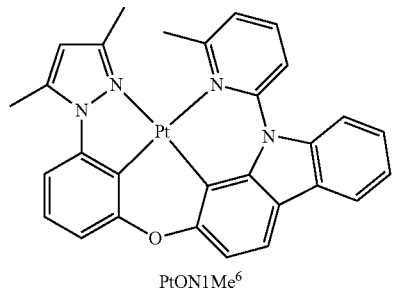
PtON1Me⁶
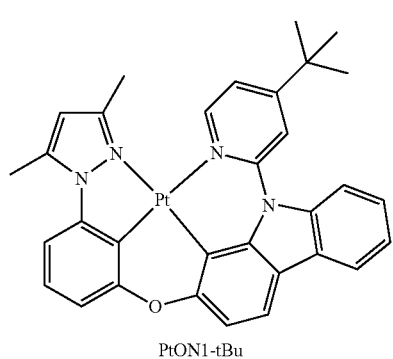
PtON1-tBu
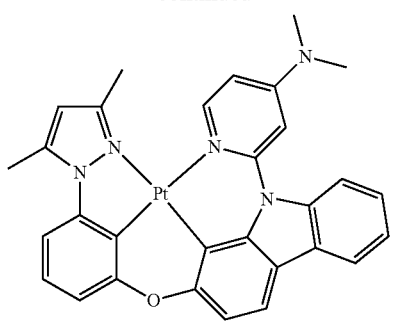
PtON1NMe₂
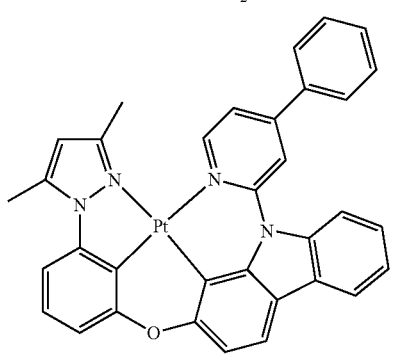
PtON1Ph
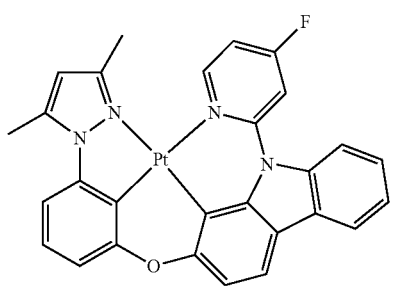
PtON1NF
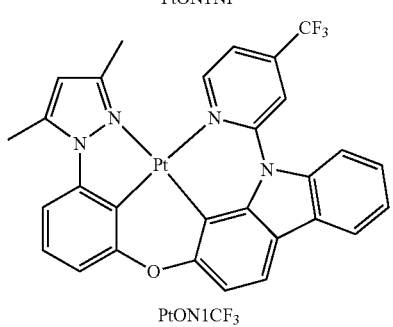
PtON1CF₃
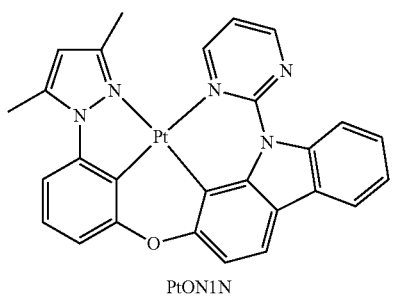
PtON1N

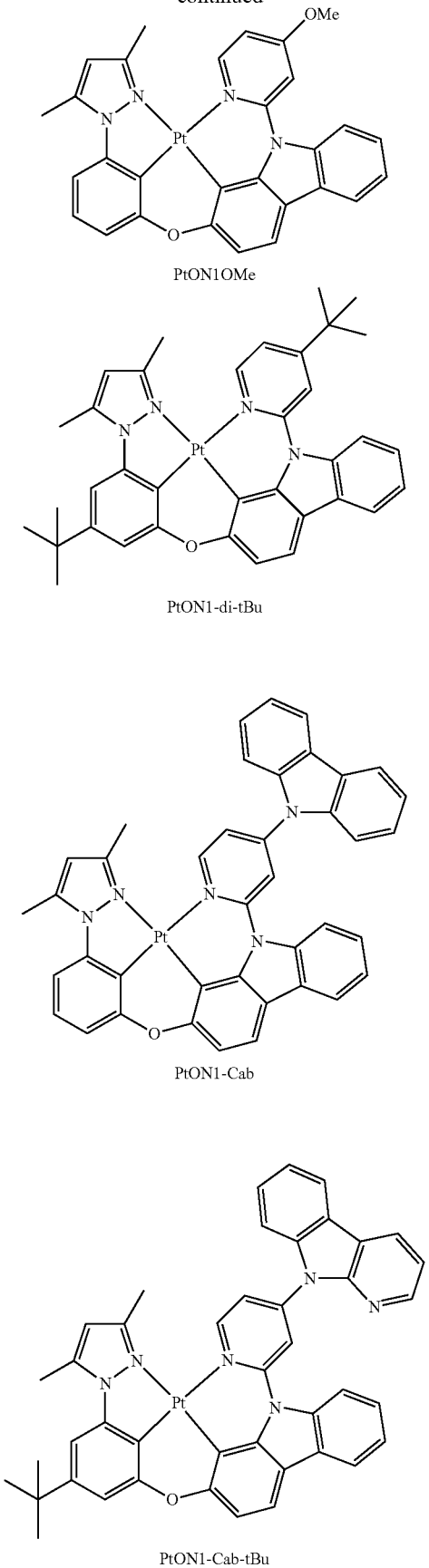

PtON1OMe

PtON1-di-tBu

PtON1-Cab

PtON1-Cab-tBu

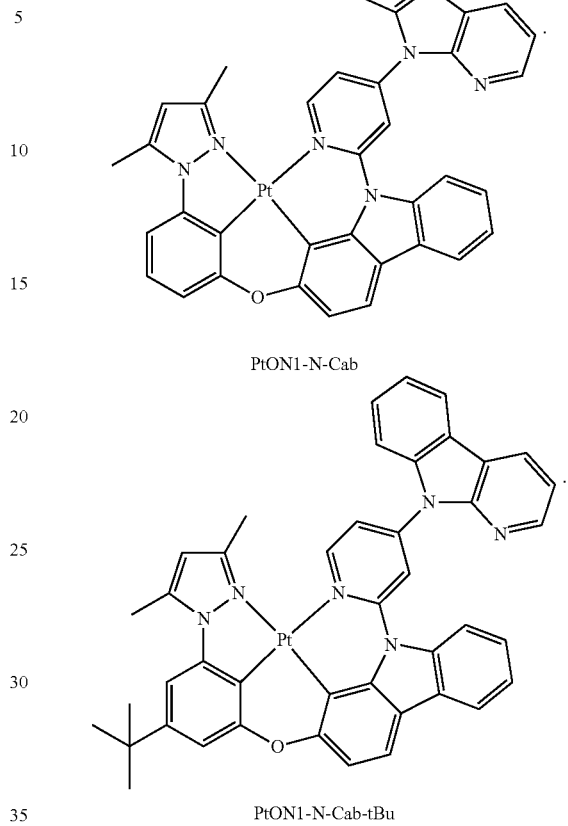

PtON1-N-Cab

PtON1-N-Cab-tBu

In some implementations, the compositions or compounds disclosed herein include one or more derivatives and/or analogues of the compounds described herein, provided that such compounds exhibit desirable properties and have emission or absorption spectra or both that can be tuned via the selection of appropriate ligands.

The compositions disclosed herein are generally suited for use in a wide variety of optical and electro-optical devices, including, for example, photo-absorbing devices such as solar- and photo-sensitive devices, photovoltaic devices, organic light emitting diodes (OLEDs), photo-emitting devices, or devices capable of both photo-absorption and emission and as markers for bio-applications. Compositions described herein include one or more multidentate metal complexes, or compounds. Thus, in some implementations, a composition includes one multidentate metal complex, and in some implementations, a composition includes two or more multidentate metal complexes.

Figure 2:
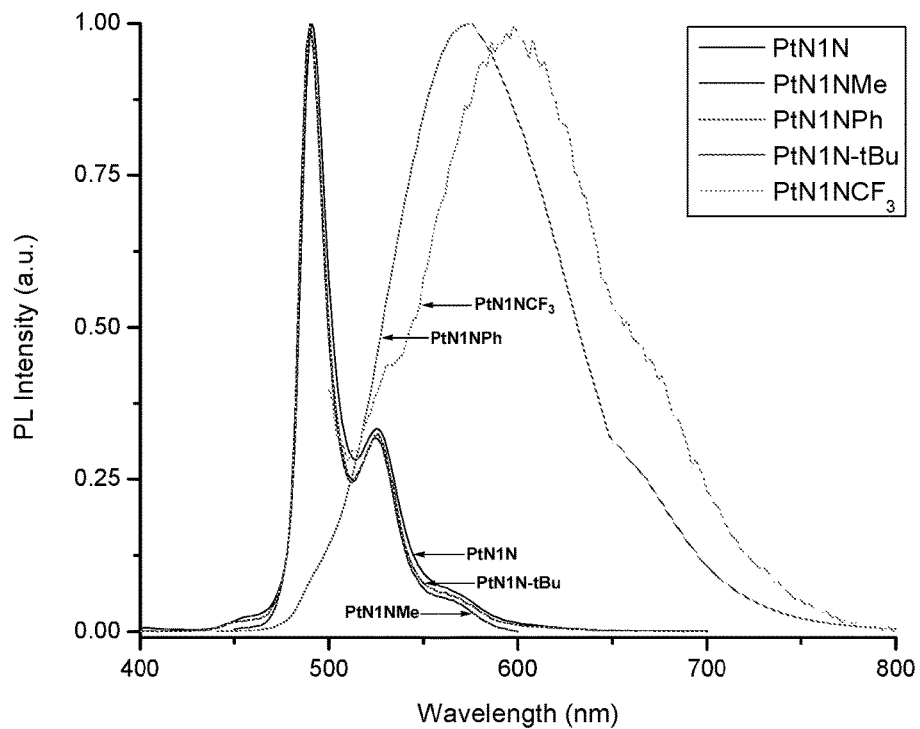
FIG. 2 shows emission spectra of PtN1N, PtN1NMe, PtN1N-tBu, PtN1NPh and PtN1NCF$_3$ in CH$_2$Cl$_2$ at room temperature.
Figure 2:
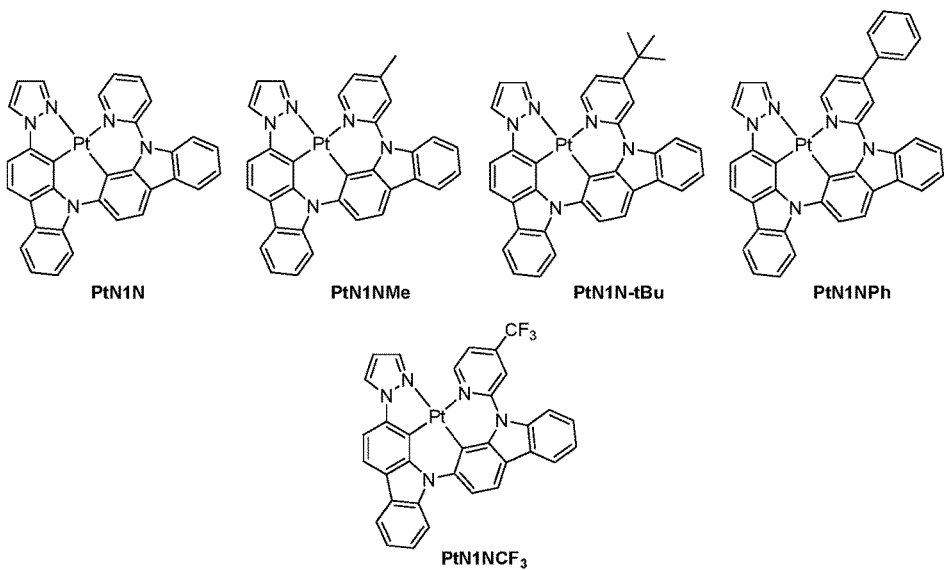
Figure 3:
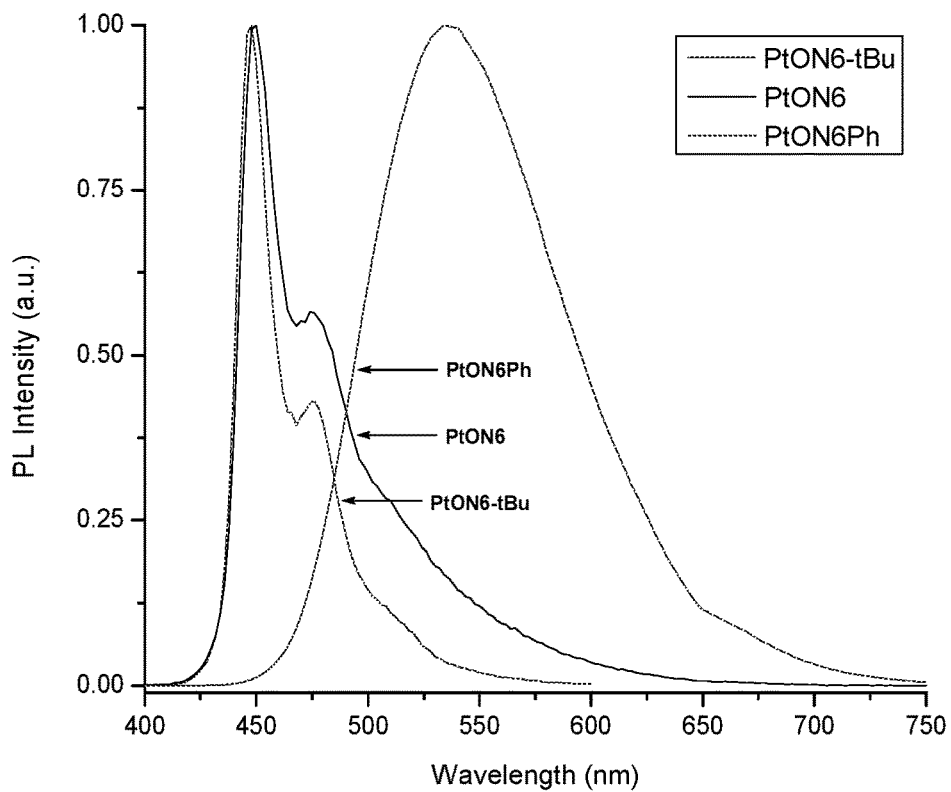
FIG. 3 shows emission spectra of PtON6, PtON6-tBu and PtON6Ph in CH$_2$Cl$_2$ at room temperature.
Figure 3:
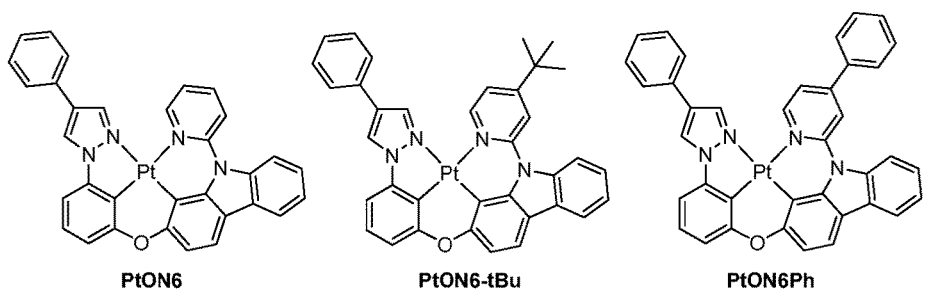
Figure 4:
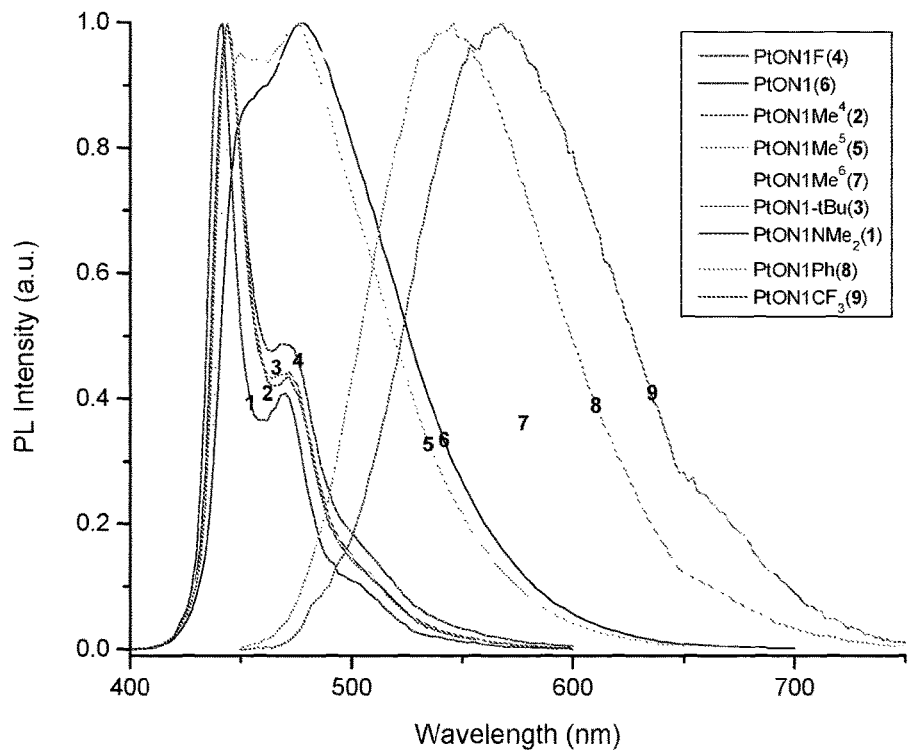
FIG. 4 shows emission spectra of PtON1, PtON1Me$^4$, PtON1Me$^5$, PtON1Me$^6$, PtON1-tBu, PtON1Ph, PtON1NMe$_2$, PtON1F and PtON1CF$_3$ in CH$_2$Cl$_2$ at room temperature.
Figure 4:
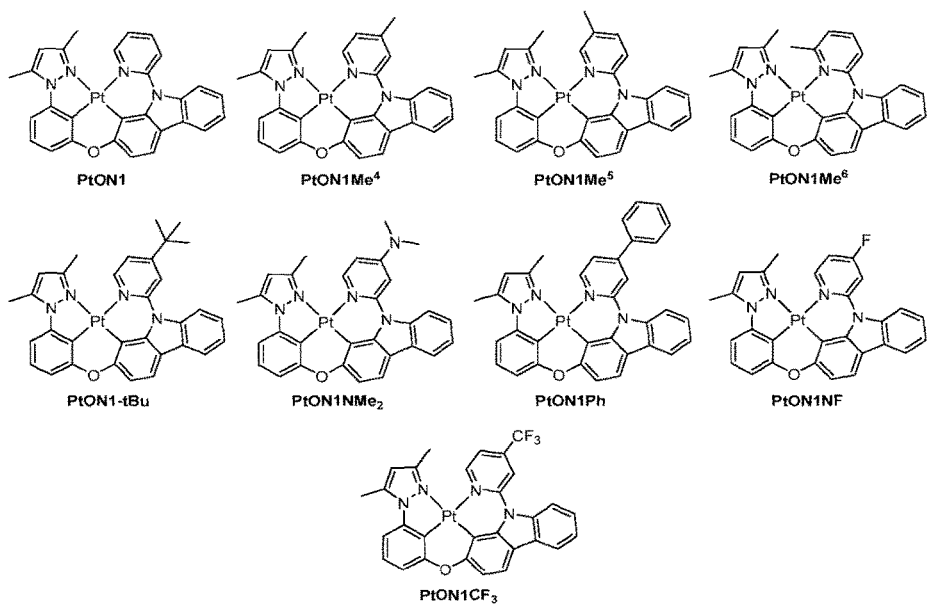

In some implementations, multidentate metal complexes described herein are combined to cover a range of wavelengths. In one example, FIG. 2 shows emission spectra of PtN1N, PtN1NMe, PtN1N-tBu, PtN1NPh and PtN1NCF$_3$ in CH$_2$Cl$_2$ at room temperature. In another example, FIG. 3 shows emission spectra of PtON6, PtON6-tBu and PtON6Ph in CH$_2$Cl$_2$ at room temperature. In yet another example, FIG. 4 shows emission spectra of PtON1, PtON1Me$^4$, PtON1Me$^5$, PtON1Me$^6$, PtON1-tBu, PtON1Ph, PtON1NMe$_2$, PtON1F and PtON1CF$_3$ in CH$_2$Cl$_2$ at room temperature. Thus, as suggested by FIGS. 2-4, compounds described herein can be used singly or combined selectively as an emissive material to yield a desired wavelength range in an OLED.

In some implementations, the compositions disclosed herein are used as host materials for OLED applications, such as full color displays.

In one aspect, the compositions disclosed herein can be useful in a wide variety of applications, such as, for example, lighting devices. In a further aspect, one or more of the complexes can be useful as host materials for an organic light emitting display device.

In another aspect, the compositions disclosed herein are useful in a variety of applications, for example, as light emitting materials. In a further aspect, the compounds can be useful in organic light emitting diodes (OLEDs), luminescent devices and displays, and other light emitting devices.

In another aspect, the compositions disclosed herein can provide improved efficiency and/or operational lifetimes in lighting devices. In some aspects, the compositions disclosed herein can provide improved efficiency and/or operational lifetimes for organic light emitting devices as compared to conventional materials.

In another aspect, the compositions disclosed herein can be useful as, for example, host materials for OLEDs, lighting applications, and combinations thereof.

In another aspect, the compositions disclosed herein can be prepared using a variety of methods, including, but not limited to those recited in the examples provided herein.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to be limiting in scope. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Various methods for the preparation method of the compounds described herein are recited in the examples. These methods are provided to illustrate various methods of preparation, but are not intended to limit any of the methods recited herein. Accordingly, one of skill in the art in possession of this disclosure could readily modify a recited method or utilize a different method to prepare one or more of the compounds described herein. The following aspects are only exemplary and are not intended to be limiting in scope. Temperatures, catalysts, concentrations, reactant compositions, and other process conditions can vary, and one of skill in the art, in possession of this disclosure, could readily select appropriate reactants and conditions for a desired complex.

$^1$H spectra were recorded at 400 MHz, $^{13}$C NMR spectra were recorded at 100 MHz on Varian Liquid-State NMR instruments in CDCl$_3$ or DMSO-d$_6$ solutions and chemical shifts were referenced to residual protiated solvent. If CDCl$_3$ was used as solvent, $^1$H NMR spectra were recorded with tetramethylsilane (δ=0.00 ppm) as internal reference; $^{13}$C NMR spectra were recorded with CDCl$_3$ (δ=77.00 ppm) as internal reference. If DMSO-d$_6$ was used as solvent, $^1$H NMR spectra were recorded with residual H$_2$O (δ=3.33 ppm) as internal reference; $^{13}$C NMR spectra were recorded with DMSO-d$_6$ (δ=39.52 ppm) as internal reference. The following abbreviations (or combinations thereof) were used to explain $^1$H NMR multiplicities: s=singlet, d=doublet, t=triplet, q=quartet, p=quintet, m=multiplet, br=broad.

Example 1

Platinum complex PtN1N can be prepared according to the following scheme:

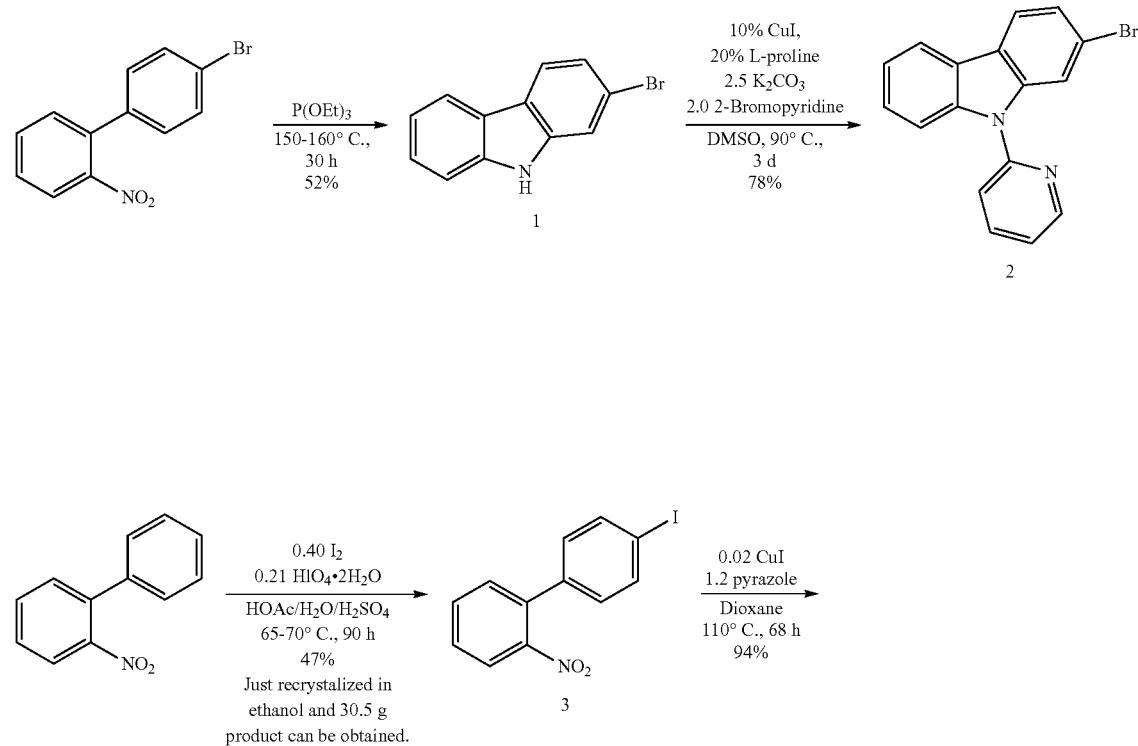

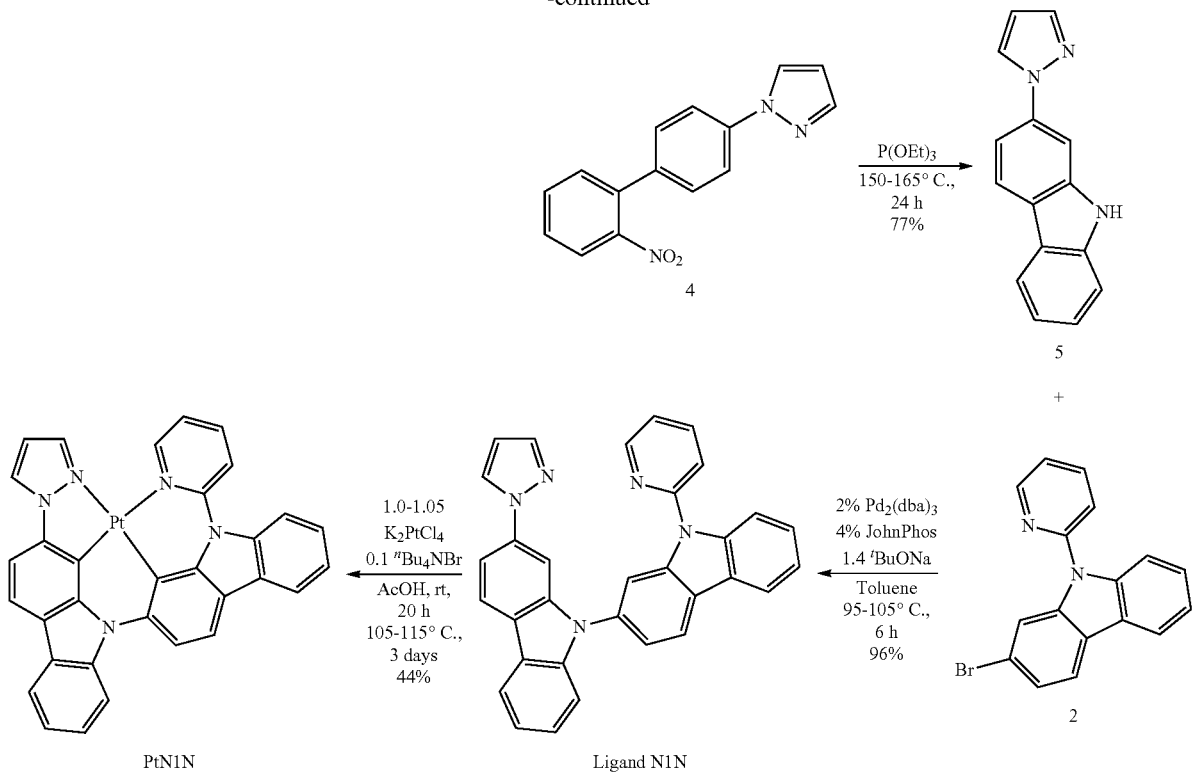

Synthesis of 2-bromo-9H-carbazole 1

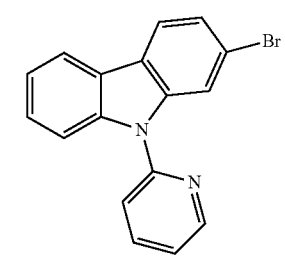 [SMILES: Brc1ccc2c3ccccc3n(-c3ccccn3)c2c1]

4'-bromo-2-nitrobiphenyl (22.40 g, 80.55 mmol) and P(OEt)₃ (150 mL) were added under nitrogen to a three-necked round bottom flask equipped with a magnetic stir bar and a condenser. The mixture was heated to 150-160° C. in an oil bath for 30 hours, cooled to ambient temperature, and the excess P(OEt)₃ was removed by distillation under high vacuum. The residue was recrystallized in toluene to afford the desired product, 2-bromo-9H-carbazole, (8.30 g) as a white crystal. The filtrate was concentrated and the residue was purified through column chromatography on silica gel using hexane and ethyl acetate (10:1-5:1) as eluent to obtain the desired product, 2-bromo-9H-carbazole 1 (2.00 g in 52% yield). $^1$H NMR (DMSO-$d_6$, 400 MHz): δ 7.17 (t, J=7.6 Hz, 1H), 7.28 (dd, J=8.0, 1.6 Hz, 1H), 7.41 (t, J=7.6 Hz, 1H), 7.49 (d, J=8.4 Hz, 1H), 7.65 (d, J=1.6 Hz, 1H), 8.06 (d, J=8.4 Hz, 1H), 8.11 (d, J=7.6 Hz, 1H), 11.38 (s, 1H). $^{13}$C NMR (DMSO-$d_6$, 100 MHz): δ 111.22, 113.50, 118.11, 119.09, 120.36, 121.29, 121.58, 121.79, 121.90, 126.09, 139.89, 140.62. The spectroscopic data is consistent with that previously reported (Pan, J.; Wang, X.; Zhang, Y.; Buchwald, S. L. *Org. Lett.* 2011, 13, 4974-4976).

Synthesis of 2-bromo-9-(pyridin-2-yl)-9H-carbazole 2

2-bromo-9H-carbazole 1 (8.33 g, 34 mmol, 1.0 eq), 2-bromopyridine (10.61 g, 68 mmol, 2.0 eq), L-proline (0.78 g, 6.8 mmol, 0.2 eq) and K₂CO₃ (11.75 g, 85 mmol, 2.5 eq) were added to a dry pressure tube equipped with a magnetic stir bar. Then the tube was taken into a glove box where CuI (0.44 g, 3.4 mmol, 0.1 eq) and DMSO (68 mL) were added. The mixture was bubbled with nitrogen for 10 minutes and then the tube was sealed. The tube was taken out of the glove box and heated to 90° C. in an oil bath. After stirring at 90° C. for 3 days, the mixture was cooled to ambient temperature and quenched with water (250 mL). The mixture was then extracted with ethyl acetate three times and the combined organic layer was washed with water three times, dried over magnesium sulfate, then filtered and washed with ethyl acetate. The filtrate was concentrated and the residue was purified through column chromatography on silica gel using hexane and ethyl acetate (20:1-10:1) as eluent to obtain the desired product, 2-bromo-9-(pyridin-2-yl)-9H-carbazole 2, as an off-white solid (8.53 g in 78% yield). $^1$H NMR (DMSO-d$_6$, 400 MHz): δ 7.33 (t, J=7.6 Hz, 1H), 7.45-7.50 (m, 3H), 7.74 (d, J=8.4 Hz, 1H), 7.78 (d, J=8.0 Hz, 1H), 7.95 (d, J=2.0 Hz, 1H), 8.11 (td, J=8.0, 2.0 Hz, 1H), 8.19 (d, J=8.4 Hz, 1H), 8.24 (d, J=7.6 Hz, 1H), 8.72 (dd, J=4.8, 1.6 Hz, 1H). $^1$H NMR (CDCl$_3$, 400 MHz): δ 7.32 (t, J=7.6 Hz, 2H), 7.41-7.47 (m, 2H), 7.60 (d, J=8.0 Hz, 1H), 7.77 (d, J=8.4 Hz, 1H), 7.91-7.95 (m, 2H), 8.01 (d, J=2.0 Hz, 1H), 8.07 (d, J=8.0 Hz, 1H), 8.72-8.73 (m, 1H). $^{13}$C NMR (CDCl$_3$, 100 MHz): δ 111.10, 114.35, 119.01, 119.78, 120.21, 121.26, 121.30, 121.61, 123.16, 123.64, 124.06, 126.58, 138.65, 139.60, 140.29, 149.78, 151.26. The spectroscopic data is consistent with that previously reported (Chu, J.-H.; Lin, P.-S.; Lee, Y-M.; Shen, W.-T., Wu, M.-J. *Chem. Eur. J.* 2011, 17, 13613-13620).

Synthesis of 4'-iodo-2-nitrobiphenyl 3

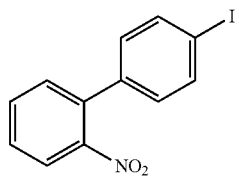 [SMILES: O=[N+]([O-])c1ccccc1-c1ccc(I)cc1]

2-nitrobiphenyl (39.84 g, 200 mmol) and HIO$_4$.2H$_2$O (9.71 g, 42.6 mmol, 0.213 eq) were added to a single-necked flask equipped with a magnetic stir bar. Then a mixture of HOAc/H$_2$O/H$_2$SO$_4$ (200 mL/40 mL/6 mL) and I$_2$ (20.20 g, 79.6 mmol, 0.398 eq) was added independently, after which a condenser was utilized and the mixture was heated to 65-70° C. in an oil bath for 90 hours until the color of I$_2$ nearly disappeared. Then the mixture was cooled to ambient temperature. Water (500 mL) was added dropwise with the mixture, and the mixture was stirred vigorously. The brown solid was then filtered off and washed with water three times. The collected solid was then dissolved in boiling ethanol (200 mL). The mixture was cooled to 45-50° C. slowly and stirred at that temperature for 3 hours. Then the mixture was cooled to ambient temperature slowly with stirring. The precipitate was then filtered off and washed with a small quantity of ethanol. The solid was dried under reduced pressure to obtain the desired product, 4'-iodo-2-nitrobiphenyl 3, as a gray-white solid (30.52 g in 47% yield). $^1$H NMR (CDCl$_3$, 400 MHz): δ 7.04-7.08 (m, 2H), 7.40 (dd, J=8.0, 1.6 Hz, 1H), 7.51 (td, J=8.0, 1.6 Hz, 1H), 7.63 (td, J=7.6, 1.2 Hz, 1H), 7.75-7.78 (m, 2H), 7.89 (dd, J=8.2, 1.6 Hz, 1H). $^{13}$C NMR (CDCl$_3$, 100 MHz): δ 94.26, 124.28, 128.56, 129.69, 131.71, 132.49, 135.33, 136.99, 137.78, 148.91. The spectroscopic data is consistent with that previously reported (Kuethe, J. T.; Childers, K. G. *Adv. Synth. Catal.* 2008, 350, 1577-1586).

Synthesis of 1-(2'-nitrobiphenyl-4-yl)-1H-pyrazole 4

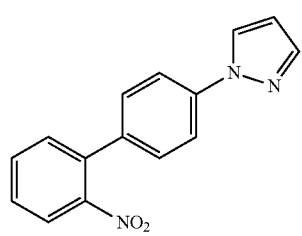 [SMILES: O=[N+]([O-])c1ccccc1-c1ccc(-n2cccn2)cc1]

4'-iodo-2-nitrobiphenyl 3 (9.75 g, 30 mmol, 1.0 eq), 1H-pyrazole (2.45 g, 36 mmol, 1.2 eq) and K$_2$CO$_3$ (8.71 g, 63 mmol, 3.1 eq) were added to a dry pressure tube equipped with a magnetic stir bar. Then the tube was taken into a glove box, wherein CuI (0.11 g, 0.6 mmol, 0.02 eq), trans-1,2-cyclohexanediamine (0.34 g, 3 mmol, 0.1 eq) and dioxane (30 mL) were added. The mixture was bubbled with nitrogen for 5 minutes and then the tube was sealed. The tube was taken out of the glove box and heated to 105-115° C. in an oil bath. The reaction was monitored by TLC and about 68 hours later the starting material 5 was consumed completely. Then the mixture was cooled to ambient temperature, diluted with ethyl acetate, then filtered and washed with ethyl acetate. The filtrate was concentrated and the residue was purified through column chromatography on silica gel using hexane and ethyl acetate (10:1-3:1) as eluent to obtain the desired product, 1-(2'-nitrobiphenyl-4-yl)-1H-pyrazole 4, as a off-white solid (7.5 g in 94% yield). $^1$H NMR (DMSO-d$_6$, 400 MHz): δ 6.57 (t, J=2.0 Hz, 1H), 7.46 (d, J=8.4 Hz, 2H), 7.59-7.65 (m, 2H), 7.75-7.79 (m, 2H), 7.92 (d, J=8.4 Hz, 2H), 7.99-8.01 (m, 1H), 8.56 (d, J=2.4 Hz, 1H). $^{13}$C NMR (DMSO-d$_6$, 100 MHz): δ 108.14, 118.56, 124.20, 127.88, 128.99, 129.06, 131.83, 133.01, 134.26, 134.62, 139.51, 141.33, 148.82.

Synthesis of 2-(1H-pyrazol-1-yl)-9H-carbazole 5

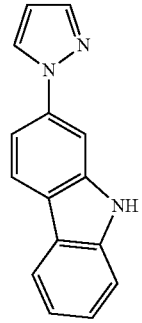 [SMILES: c1ccc2c(c1)[nH]c1cc(-n3cccn3)ccc12]

1-(2'-nitrobiphenyl-4-yl)-1H-pyrazole 4 (7.23 g, 27.26 mmol) was added to a three-necked flask equipped with a magnetic stir bar and a condenser. The flask was evacuated and backfilled with nitrogen. The evacuation and backfill procedure was repeated twice, and then P(OEt)$_3$ (150 mL) was added under nitrogen. The mixture was stirred in an oil bath at a temperature of 150-165° C. for 24 hours. The mixture was then cooled and the excess P(OEt)$_3$ was removed by distillation under high vacuum. The residue was recrystallized in ethyl acetate to yield the desired product as a white solid (3.60 g). The filtrate was concentrated and the residue was purified through column chromatography on silica gel using hexane and ethyl acetate (10:1-5:1-3:1-2:1) as eluent to obtain an additional crop of the desired product, 2-(1H-pyrazol-1-yl)-9H-carbazole 5 (1.30 g in 77% yield). $^1$H NMR (DMSO-d$_6$, 400 MHz): δ 6.55-6056 (m, 1H), 7.17 (t, J=7.6 Hz, 1H), 7.36-7.40 (m, 1H), 7.48-7.50 (m, 1H), 7.64 (dt, J=8.0, 0.8 Hz, 1H), 7.76 (s, 1H), 7.90 (d, J=2.0 Hz, 1H), 8.11 (d, J=7.6 Hz, 1H), 8.18 (d, J=8.8 Hz, 1H), 8.55 (d, J=2.8 Hz, 1H), 11.40 (s, 1H). $^{13}$C NMR (DMSO-d$_6$, 100 MHz): δ 100.97, 107.65, 109.96, 111.01, 118.94, 120.16, 120.74, 120.99, 122.11, 125.55, 127.96, 137.87, 140.11, 140.42, 140.71.

Synthesis of 2'-(1H-pyrazol-1-yl)-9-(pyridin-2-yl)-9H-2,9'-bicarbazole Ligand N1N

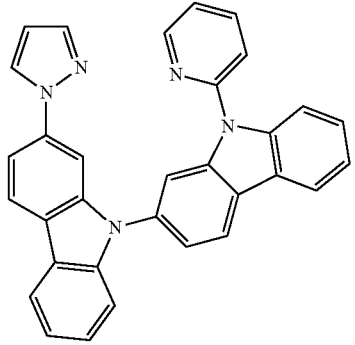 [SMILES: c1ccc(-n2c3ccccc3c3ccc(-n4c5ccccc5c5ccc(-n6cccn6)cc54)cc32)nc1]

2-(1H-pyrazol-1-yl)-9H-carbazole 5 (3.50 g, 15.0 mmol, 1.0 eq), 2-bromo-9-(pyridin-2-yl)-9H-carbazole 2 (5.82 g, 18 mmol, 1.2 eq), Pd$_2$(dba)$_3$ (0.28 g, 0.3 mmol, 0.02 eq), and JohnPhos (2-biphenyl)di-tert-butylphosphine) (0.18 g, 0.6 mmol, 0.04 eq) was added to a dry pressure tube equipped with a magnetic stir bar. The tube was then taken into a glove box. $^t$BuONa (2.02 g, 21 mmol, 1.4 eq) and dry toluene (60 mL) were added. The mixture was bubbled with nitrogen for 10 minutes and then the tube was sealed. The tube was taken out of the glove box and heated to 95-105° C. in an oil bath. The reaction was monitored by TLC and about 6 hours later the starting material 5 was consumed completely. Then the mixture was cooled to ambient temperature and diluted with ethyl acetate. The mixture was concentrated and the residue was purified through column chromatography on silica gel using hexane and ethyl acetate (10:1-5:1-3:1) as eluent to obtain the desired product, 2'-(1H-pyrazol-1-yl)-9-(pyridin-2-yl)-9H-2,9'-bicarbazole Ligand N1N, as a brown solid (6829 mg in 96% yield). $^1$H NMR (DMSO-d$_6$, 400 MHz): δ 6.53 (t, J=1.6 Hz, 1H), 7.31-7.35 (m, 1H), 7.42-7.47 (m, 4H), 7.57 (t, J=8.4 Hz, 1H), 7.61 (dd, J=8.0, 1.6 Hz, 1H), 7.70 (d, J=1.6 Hz, 1H), 7.81 (dd, J=8.8, 1.6 Hz, 1H), 7.86 (d, J=1.2 Hz, 1H), 7.90 (d, J=8.4 Hz, 2H), 8.05 (d, J=1.6 Hz, 1H), 8.09 (td, J=8.0, 1.6 Hz, 1H), 8.30 (d, J=7.6 Hz, 1H), 8.38 (d, J=8.4 Hz, 1H), 8.41 (d, J=8.0 Hz, 1H), 8.57-8.60 (m, 2H), 8.67-8.68 (m, 1H). $^1$H NMR (CDCl$_3$, 400 MHz): δ 6.42 (t, J=2.0 Hz, 1H), 7.22-7.26 (m, 1H), 7.28-7.32 (m, 1H), 7.37-7.43 (m, 3H), 7.48-7.52 (m, 2H), 7.61 (dd, J=8.0, 1.6 Hz, 1H), 7.66 (d, J=8.0 Hz, 1H), 7.68 (d, J=1.6 Hz, 1H), 7.76 (d, J=2.0 Hz, 1H), 7.84-7.89 (m, 2H), 7.94 (d, J=2.4 Hz, 1H), 8.04 (d, J=2.0 Hz, 1H), 8.13 (d, J=7.2 Hz, 1H), 8.16-8.20 (m, 2H), 8.31 (d, J=8.0 Hz, 1H), 8.63 (dd, J=4.8, 0.8 Hz, 1H). $^{13}$C NMR (CDCl$_3$, 100 MHz): δ 101.22, 107.40, 110.12, 110.64, 111.21, 111.81, 119.00, 120.16, 120.20, 120.24, 120.42, 120.99, 121.40, 121.43, 121.56, 121.72, 122.77, 123.78, 123.97, 126.01, 126.70, 127.21, 135.08, 138.69, 138.70, 140.29, 140.31, 140.88, 141.94, 142.22, 149.77, 151.36.

Synthesis of 2'-(1H-pyrazol-1-yl)-9-(pyridin-2-yl)-9H-2,9'-bicarbazole platinum complex PtN1N

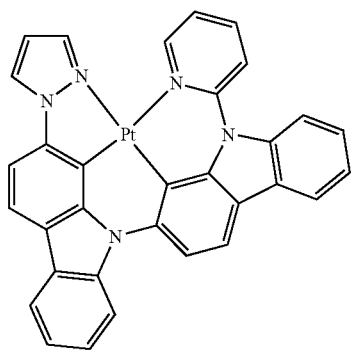

2'-(1H-pyrazol-1-yl)-9-(pyridin-2-yl)-9H-2,9'-bicarbazole Ligand N1N (1427 mg, 3.0 mmol, 1.0 eq), K$_2$PtCl$_4$ (1308 mg, 3.15 mmol, 1.05 eq) and $^n$Bu$_4$NBr (97 mg, 0.3 mmol, 0.1 eq) were added to a dry pressure tube equipped with a magnetic stir bar. The tube was then taken into a glove box and acetic acid (180 mL) was added. The mixture was bubbled with nitrogen for 30 minutes and then the tube was sealed. The tube was taken out of the glove box and the mixture was stirred at room temperature for 20 hours. Then the mixture was heated to 105-115° C. in an oil bath and stirred at that temperature for three days, cooled to ambient temperature and water (180 mL) was added slowly. After stirring at room temperature for 10 minutes, the precipitate was filtered off and washed with water three times. Then the solid was dried in air under reduced pressure. The collected solid was purified through column chromatography on silica gel using dichloromethane as eluent to obtain the desired product, 2'-(1H-pyrazol-1-yl)-9-(pyridin-2-yl)-9H-2,9'-bicarbazole platinum complex PtN1N, as a yellow solid 872 mg in 44% yield. The product (546 mg) was further purified by sublimation in a sublimator with four zone controllers under high vacuum. The sublimation conditions were: 180° C., 180° C., 140° C., 100° C., 4.6×10$^{-6}$ Pa for 0.5 hour; then 200° C., 200° C., 170° C., 140° C., 4.1×10$^{-6}$ Pa, 19 hours; then 255° C., 255° C., 210° C., 180° C., 4.1×10$^{-6}$ Pa, 1 hour; then 265° C., 260° C., 210° C., 180° C., 4.1×10$^{-6}$ Pa, 1.5 hours; then 270° C., 265° C., 210° C., 180° C., 4.1×10-6 Pa, 93 hours; then 275° C., 265° C., 210° C., 180° C., 4.1×10$^{-6}$ Pa, 48 hours. The sublimator was then cooled to ambient temperature and the desired product PtN1N was obtained as yellow solid (295 mg in 54% yield). FIG. 1 shows an emission spectrum of PtN1N in CH$_2$Cl$_2$ at room temperature. $^1$H NMR (DMSO-d$_6$, 400 MHz): δ 6.86 (t, J=2.0 Hz, 1H), 7.30 (t, J=7.6 Hz, 1H), 7.40-7.44 (m, 2H), 7.48-7.52 (m, 2H), 7.70 (d, J=8.4 Hz, 1H), 7.95 (d, J=8.0 Hz, 1H), 8.00 (d, J=8.0 Hz, 1H), 8.07 (d, J=8.0 Hz, 1H), 8.10 (d, J=2.0 Hz, 1H), 8.14 (d, J=8.0 Hz, 1H), 8.20-8.27 (m, 5H), 8.90 (d, J=2.8 Hz, 1H), 9.20 (d, J=5.6 Hz, 1H). $^{13}$C NMR (DMSO-d$_6$, 100 MHz): δ 106.00, 107.65, 108.24, 11.58, 113.00, 113.54, 114.40, 115.31, 115.35, 116.47, 116.93, 118.27, 120.19, 120.45, 120.59, 120.91, 122.89, 125.09, 125.59, 126.09, 127.48, 128.87, 137.97, 138.21, 138.27, 139.28, 139.91, 140.23, 143.32, 143.35, 147.26, 151.84. Anal. Calcd. for C$_{32}$H$_{19}$N$_5$Pt: C, 57.48, H, 2.86, N, 10.47; Found: C, 57.29, H, 3.06, N, 10.39.

Example 2

Platinum complex PtN1NMe can be prepared according to the following scheme:

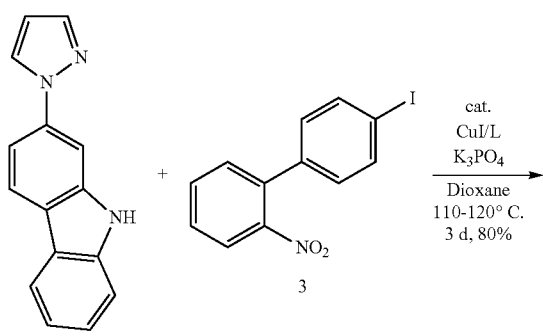
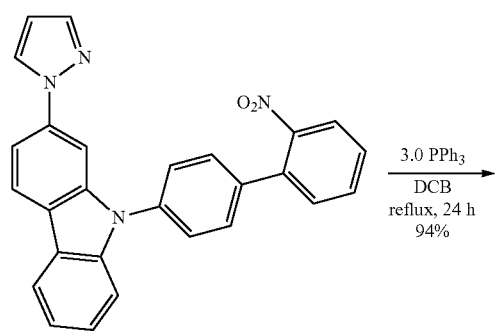
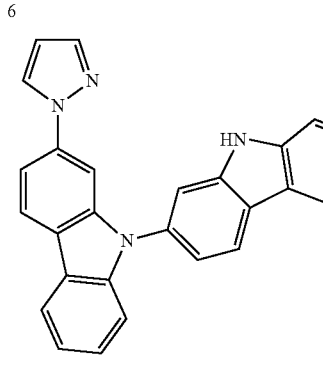
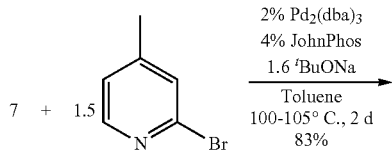
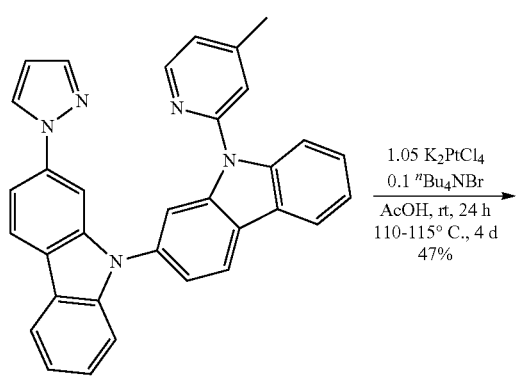

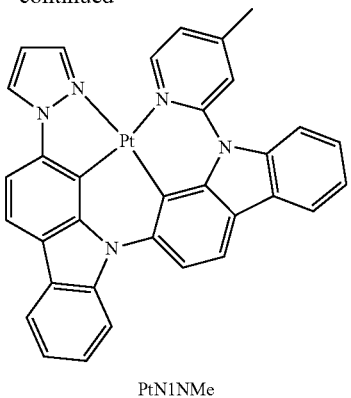

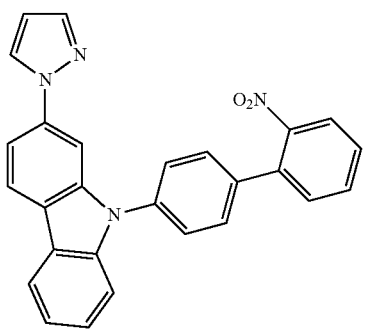 [SMILES: O=[N+]([O-])c1ccccc1-c1ccc(-n2c3ccccc3c3ccc(-n4cccn4)cc32)cc1]

Synthesis of 9-(2'-nitrobiphenyl-4-yl)-2-(1H-pyrazol-1-yl)-9H-carbazole 6

2-(1H-pyrazol-1-yl)-9H-carbazole 5 (1.35 g, 5.78 mmol, 1.0 eq), 4'-iodo-2-nitrobiphenyl 3 (2.26 g, 6.94 mmol, 1.2 eq), $K_3PO_4$ (2.58 g, 12.14 mmol, 2.1 eq) and CuI (55 mg, 0.29 mmol, 0.05 eq) were added to a dry pressure tube equipped with a magnetic stir bar. The tube was evacuated and backfilled with nitrogen. The evacuation and backfill procedure was repeated twice, and then 1,2-cyclohexanediamine (0.33 g, 290 uL, 2.89 mmol, 0.5 eq) and dioxane (20 mL) were added. The mixture was bubbled with nitrogen for 30 minutes and then the tube was sealed. The mixture was stirred in an oil bath at a temperature of 110-120° C. for three days and then cooled to ambient temperature. The solvent was removed under reduced pressure and the residue was purified through column chromatography on silica gel using hexane and ethyl acetate (10:1-3:1), then dichloromethane and methanol (20:1) as eluent to obtain the desired product, 9-(2'-nitrobiphenyl-4-yl)-2-(1H-pyrazol-1-yl)-9H-carbazole 6, as a brown solid (1.98 g in 80% yield). $^1$H NMR (DMSO-$d_6$, 400 MHz): δ 6.55 (t, J=1.6 Hz, 1H), 7.32-7.36 (m, 1H), 7.42 (d, J=8.0 Hz, 1H), 7.45-7.49 (m, 1H), 7.67-7.76 (m, 5H), 7.78-7.81 (m, 3H), 7.84 (dd, J=8.0, 1.6 Hz, 1H), 7.87 (d, J=1.6 Hz, 1H), 8.08 (dd, J=8.4, 1.2 Hz, 1H), 8.29 (d, J=8.0 Hz, 1H), 8.37 (d, J=8.4 Hz, 1H), 8.59 (d, J=1.6 Hz, 1H).

Synthesis of 2'-(1H-pyrazol-1-yl)-9H-2,9'-bicarbazole 7

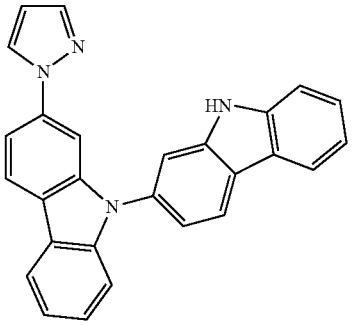 [SMILES: c1ccc2c(c1)[nH]c1cc(-n3c4ccccc4c4ccc(-n5cccn5)cc43)ccc12]

9-(2'-nitrobiphenyl-4-yl)-2-(1H-pyrazol-1-yl)-9H-carbazole 6 (1.95 g, 4.53 mmol, 1.0 eq) and PPh₃ (3.57 g, 13.59 mmol, 3.0 eq) were added to a three-necked flask equipped with a magnetic stir bar and a condenser. The flask was evacuated and backfilled with nitrogen. The evacuation and backfill procedure was repeated twice, and then 1,2-dichlorobenzene (25 mL) was added under nitrogen. The mixture was refluxed (175-185° C.) in an oil bath for 24 hours, then cooled, and the solvent was removed by distillation under high vacuum. The residue was purified through column chromatography on silica gel using hexane and ethyl acetate (10:1-5:1-3:1) as eluent to obtain the desired product, 2'-(1H-pyrazol-1-yl)-9H-2,9'-bicarbazole 7, as a white solid (1.69 g in 94% yield). $^1$H NMR (DMSO-d$_6$, 400 MHz): δ 6.51 (t, J=1.6 Hz, 1H), 7.24 (t, J=7.2 Hz, 1H), 7.30-7.34 (m, 1H), 7.39 (dd, J=8.4, 1.2 Hz, 1H), 7.41-7.47 (m, 3H), 7.57 (d, J=8.0 Hz, 1H), 7.67 (d, J=1.6 Hz, 1H), 7.72 (d, J=1.6 Hz, 1H), 7.79 (dd, J=8.0, 1.6 Hz, 1H), 7.85 (d, J=1.6 Hz, 1H), 8.24 (d, J=7.6 Hz, 1H), 8.29 (d, J=8.0 Hz, 1H), 8.37 (d, J=8.8 Hz, 1H), 8.41 (d, J=8.0 Hz, 1H), 8.56 (d, J=2.0 Hz, 1H), 11.51 (s, 1H).

Synthesis of 9-(4-methylpyridin-2-yl)-2'-(1H-pyrazol-1-yl)-9H-2,9'-bicarbazole Ligand N1NMe

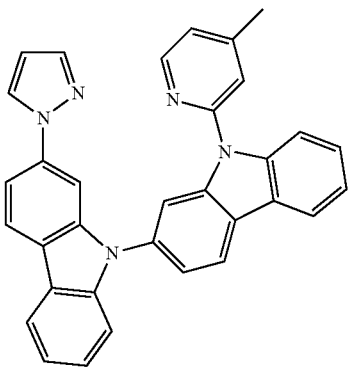 [SMILES: Cc1ccnc(-n2c3ccccc3c3ccc(-n4c5ccccc5c5ccc(-n6cccn6)cc54)cc32)c1]

2'-(1H-pyrazol-1-yl)-9H-2,9'-bicarbazole 7 (398 mg, 1.0 mmol, 1.0 eq), Pd₂(dba)₃ (18 mg, 0.02 mmol, 0.02 eq), JohnPhos (12 mg, 0.4 mmol, 0.4 eq) and $^t$BuONa (154 mg, 1.6 mmol, 1.6 eq) were added to a dry pressure Schlenk tube equipped with a magnetic stir bar. The tube was then evacuated and backfilled with nitrogen. The evacuation and backfill procedure was repeated twice, and then dry toluene (3 mL) and 2-bromo-4-methyl-butylpyridine (258 mg, 1.5 mmol, 1.5 eq) were added under nitrogen. The tube was sealed and the mixture was stirred in an oil bath at a temperature of 100-105° C. for 2 days. Then the mixture was cooled to ambient temperature. The solvent was removed under reduced pressure and the residue was purified through column chromatography on silica gel using hexane and ethyl acetate (10:1-5:1) as eluent to obtain the desired product, 9-(4-methylpyridin-2-yl)-2'-(1H-pyrazol-1-yl)-9H-2,9'-bicarbazole Ligand N1NMe, as a white solid (415 mg in 83% yield). $^1$H NMR (DMSO-d$_6$, 400 MHz): δ 2.39 (s, 3H), 6.50 (t, J=2.4 Hz, 1H), 7.25 (d, J=5.2 Hz, 1H), 7.28-7.32 (m, 1H), 7.39-7.43 (m, 3H), 7.52-7.56 (m, 1H), 7.58 (dd, J=8.1, 1.6 Hz, 1H), 7.67 (d, J=1.6 Hz, 1H), 7.69 (s, 1H), 7.78 (dd, J=8.0, 1.6 Hz, 1H), 7.85 (s, 1H), 7.86 (d, J=8.8 Hz, 1H), 8.00 (d, J=2.0 Hz, 1H), 8.27 (d, J=7.6 Hz, 1H), 8.36 (t, J=8.8 Hz, 2H), 8.48 (d, J=5.2 Hz, 1H), 8.55 (d, J=5.6 Hz, 1H), 8.56 (s, 1H).

Synthesis of 9-(4-methylpyridin-2-yl)-2'-(1H-pyrazol-1-yl)-9H-2,9'-bicarbazole platinum complex PtN1Nme

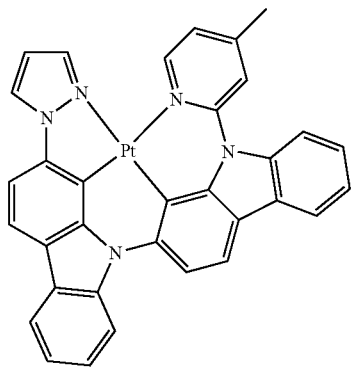

9-(4-methylpyridin-2-yl)-2'-(1H-pyrazol-1-yl)-9H-2,9'-bicarbazole Ligand N1NMe (405 mg, 0.81 mmol, 1.0 eq), K₂PtCl₄ (353 mg, 0.85 mmol, 1.05 eq), "Bu₄NBr (26 mg, 0.081 mmol, 0.1 eq) and acetic acid (49 mL) were added to a dry pressure tube equipped with a magnetic stir bar. The mixture was bubbled with nitrogen for 30 minutes and then the tube was sealed. The mixture was then stirred at room temperature for 24 hours. Then the mixture was heated to 110-115° C. in an oil bath and stirred at that temperature for 4 days, cooled to ambient temperature, and water (60 mL) was added. After stirring at room temperature for 5 minutes, the precipitate was filtered off and washed with water three times. Then the solid was dried in air under reduced pressure. The collected solid was purified through column chromatography on silica gel using dichloromethane as eluent to obtain the desired product, 9-(4-methylpyridin-2-yl)-2'-(1H-pyrazol-1-yl)-9H-2,9'-bicarbazole platinum complex PtN1NMe, as a yellow solid (260 mg in 47% yield). FIG. 1 shows an emission spectrum of PtN1NMe in CH₂Cl₂ at room temperature. $^1$H NMR (DMSO-d$_6$, 400 MHz): δ 2.46 (s, 3H), 6.85 (t, J=2.4 Hz, 1H), 7.28-7.31 (m, 2H), 7.42 (t, J=7.6 Hz, 1H), 7.48 (d, J=7.6 Hz, 1H), 7.52 (d, J=7.6 Hz, 1H), 7.68 (d, J=8.4 Hz, 1H), 7.94 (d, J=8.0 Hz, 1H), 7.99 (d, J=8.4 Hz, 1H), 8.06 (s, 1H), 8.08 (d, J=1.6 Hz, 1H), 8.10 (d, J=7.6 Hz, 1H), 8.12 (d, J=8.8 Hz, 1H), 8.20 (d, J=4.0 Hz, 1H), 8.21 (d, J=4.0 Hz, 1H), 8.25 (d, J=8.0 Hz, 1H), 8.88 (d, J=2.4 Hz, 1H), 9.05 (d, J=6.4 Hz, 1H). $^{13}$C NMR (DMSO-d$_6$, 100 MHz): δ 21.03, 105.99, 107.64, 108.36, 111.91, 113.01, 113.50, 114.50, 115.23, 115.24, 116.27, 116.93, 118.25, 120.13, 120.42, 120.92, 121.86, 122.73, 125.12, 125.58, 126.09, 127.43, 128.84, 137.92, 138.25, 138.28, 139.29, 140.15, 143.30, 143.50, 147.03, 151.11, 151.53.

Example 3

Platinum complex PtN1N-tBu can be prepared according to the following scheme:

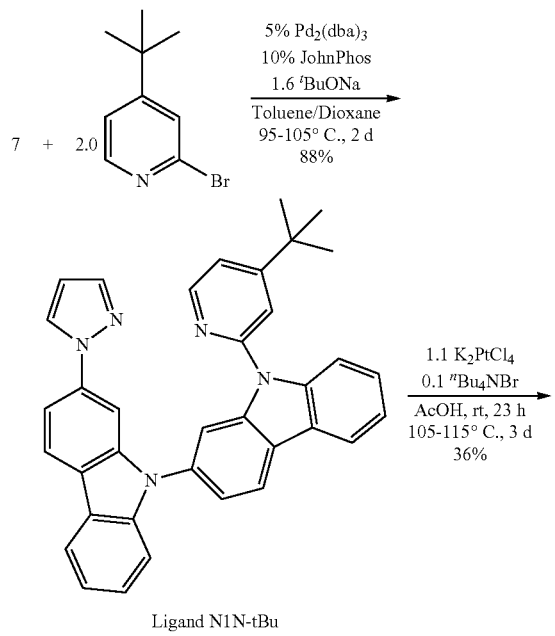

Synthesis of 9-(4-tert-butylpyridin-2-yl)-2'-(1H-pyrazol-1-yl)-9H-2,9'-bicarbazole Ligand N1N-tBu

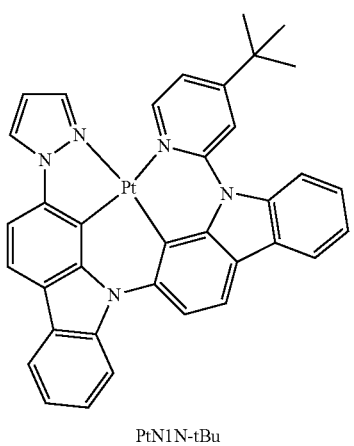

2'-(1H-pyrazol-1-yl)-9H-2,9'-bicarbazole 7 (398 mg, 1.0 mmol, 1.0 eq), Pd$_2$(dba)$_3$ (46 mg, 0.05 mmol, 0.05 eq), JohnPhos (30 mg, 0.1 mmol, 0.1 eq) and $^t$BuONa (154 mg, 1.6 mmol, 1.6 eq) were added to a dry pressure Schlenk tube equipped with a magnetic stir bar. The tube was then evacuated and backfilled with nitrogen. The evacuation and backfill procedure was repeated twice, then dry toluene (4 mL), dioxane (4 mL), and 2-bromo-4-tert-butylpyridine (418 mg, 2.0 mmol, 2.0 eq) were added under nitrogen. The tube was sealed and the mixture was stirred in an oil bath at a temperature of 95-105° C. for 2 days. Then the mixture was cooled to ambient temperature. The solvent was removed under reduced pressure and the residue was purified through column chromatography on silica gel using hexane and ethyl acetate (10:1-5:1) as eluent to obtain the desired product, 9-(4-tert-butylpyridin-2-yl)-2'-(1H-pyrazol-1-yl)-9H-2,9'-bicarbazole Ligand N1N-tBu, as a brown solid (470 mg in 88% yield). $^1$H NMR (DMSO-d$_6$, 400 MHz): δ 1.28 (s, 9H), 6.52 (t, J=1.6 Hz, 1H), 7.33 (t, J=8.0 Hz, 1H), 7.42-7.45 (m, 3H), 7.50 (d, J=8.4 Hz, 1H), 7.55-7.59 (m, 1H), 7.61 (dd, J=8.0, 2.0 Hz, 1H), 7.69 (d, J=1.6 Hz, 1H), 7.82 (dd, J=8.4, 2.0 Hz, 1H), 7.86-7.88 (m, 2H), 7.91 (d, J=2.0 Hz, 1H), 7.94 (d, J=1.6 Hz, 1H), 8.28 (d, J=8.0 Hz, 1H), 8.36 (d, J=8.8 Hz, 1H), 8.40 (d, J=8.0 Hz, 1H), 8.56 (d, J=5.2 Hz, 1H), 8.59 (d, J=8.4 Hz, 1H), 8.60 (s, 1H). $^{13}$C NMR (CDCl$_3$, 100 MHz): δ 30.05, 34.86, 99.67, 104.57, 107.74, 109.80, 111.17, 111.42, 116.16, 119.42, 119.69, 120.44, 120.53, 120.77, 120.82, 121.34, 121.53, 122.07, 122.38, 123.01, 123.03, 126.25, 126.91, 128.12, 134.57, 138.43, 139.76, 139.82, 140.80, 141.16, 141.36, 149.44, 150.58, 163.20.

Synthesis of 9-(4-tert-butylpyridin-2-yl)-2'-(1H-pyrazol-1-yl)-9H-2,9'-bicarbazole platinum complex PtN1N-tBu

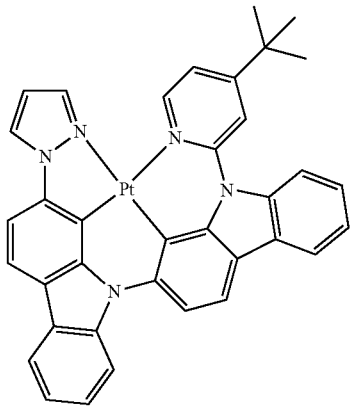

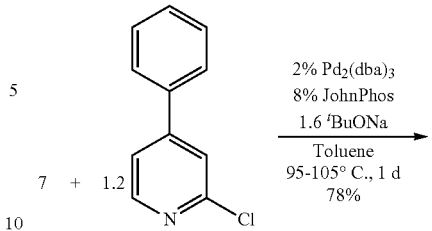

9-(4-tert-butylpyridin-2-yl)-2'-(1H-pyrazol-1-yl)-9H-2,9'-bicarbazole Ligand N1N-tBu (460 mg, 0.87 mmol, 1.0 eq), $K_2PtCl_4$ (395 mg, 0.95 mmol, 1.1 eq), $^nBu_4NBr$ (28 mg, 0.087 mmol, 0.1 eq) and acetic acid (52 mL) were added to a dry pressure tube equipped with a magnetic stir bar. The mixture was bubbled with nitrogen for 30 minutes and then the tube was sealed. The mixture was stirred at room temperature for 23 hours. Then the mixture was heated to 105-115° C. in an oil bath and stirred at that temperature for 3 days. The mixture was then cooled to ambient temperature and water (52 mL) was added slowly. After stirring at room temperature for 5 minutes, the precipitate was filtered off and washed with water three times. Then the solid was dried in air under reduced pressure. The collected solid was purified through column chromatography on silica gel using dichloromethane as eluent to obtain the desired product, 9-(4-tert-butylpyridin-2-yl)-2'-(1H-pyrazol-1-yl)-9H-2,9'-bicarbazole platinum complex PtN1N-tBu, as a yellow solid (226 mg in 36% yield). FIG. 1 shows an emision spectrum of PtN1N-tBu in $CH_2Cl_2$ at room temperature. $^1H$ NMR (DMSO-$d_6$, 400 MHz): δ 1.38 (s, 9H), 6.83 (t, J=2.4 Hz, 1H), 7.30 (t, J=7.6 Hz, 1H), 7.42 (t, J=7.6 Hz, 1H), 7.48-7.53 (m, 3H), 7.69 (d, J=8.0 Hz, 1H), 7.94 (d, J=8.0 Hz, 1H), 8.00 (d, J=8.8 Hz, 1H), 8.06 (d, J=8.0 Hz, 1H), 8.10-8.12 (m, 2H), 8.14 (d, J=8.8 Hz, 1H), 8.22 (d, J=7.6 Hz, 2H), 8.26 (d, J=8.0 Hz, 1H), 8.88 (d, J=2.8 Hz, 1H), 9.08 (d, J=6.4 Hz, 1H). $^{13}C$ NMR (DMSO-$d_6$, 100 MHz): δ 29.64, 35.45, 106.00, 107.63, 108.29, 111.88, 112.71, 112.99, 113.51, 114.07, 115.26, 115.27, 116.90, 118.26, 118.38, 120.34, 120.43, 120.92, 122.81, 125.19, 125.59, 126.10, 127.53, 128.85, 137.98, 138.24, 138.39, 139.29, 140.19, 143.32, 143.50, 147.19, 151.33, 163.22.

Example 4

Platinum complex PtN1NPh can be prepared according to the following scheme:

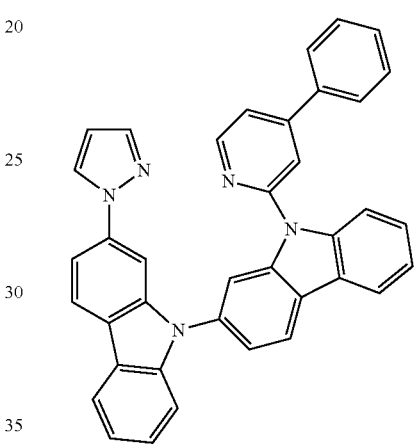

Ligand N1NPh

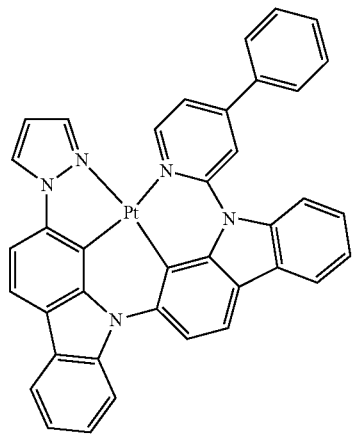

PtN1NPh

Synthesis of 9-(4-phenylpyridin-2-yl)-2'-(1H-pyrazol-1-yl)-9H-2,9'-bicarbazole Ligand N1NPh Synthesis of 9-(4-phenylpyridin-2-yl)-2'-(1H-pyrazol-1-yl)-9H-2,9'-bicarbazole platinum complex PtN1NPh

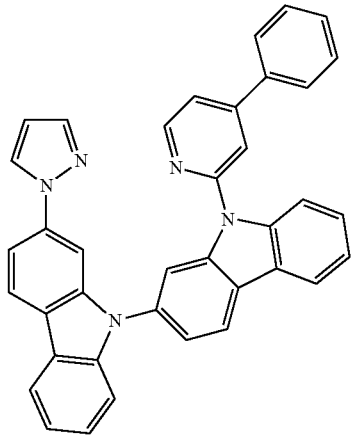 [SMILES: c1ccc(-c2ccnc(-n3c4ccccc4c4ccc(-n5c6ccccc6c6ccc(-n7cccn7)cc65)cc43)c2)cc1]

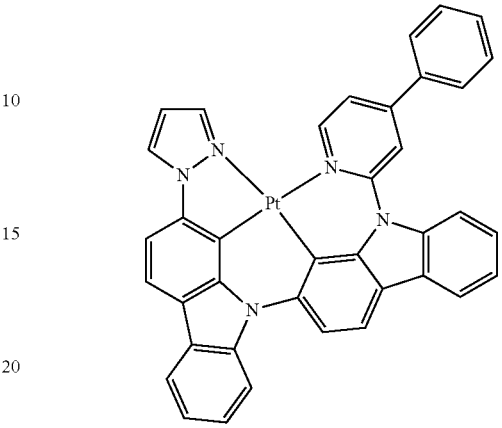

2'-(1H-pyrazol-1-yl)-9H-2,9'-bicarbazole 7 (398 mg, 1.0 mmol, 1.0 eq), 2-chloro-4-phenylpyridine (228 mg, 1.2 mmol, 1.2 eq), Pd$_2$(dba)$_3$ (18 mg, 0.02 mmol, 0.02 eq), JohnPhos (24 mg, 0.8 mmol, 0.8 eq) and $^t$BuONa (154 mg, 1.6 mmol, 1.6 eq) were added to a dry pressure Schlenk tube equipped with a magnetic stir bar. The tube was then evacuated and backfilled with nitrogen. The evacuation and backfill procedure was repeated twice, and then dry toluene (4 mL) was added under nitrogen. The tube was sealed and the mixture was stirred in an oil bath at a temperature of 95-105° C. for 1 day. Then the mixture was cooled to ambient temperature. The solvent was removed under reduced pressure and the residue was purified through column chromatography on silica gel using hexane and ethyl acetate (10:1-5:1-3:1) as eluent to obtain the desired product, 9-(4-phenylpyridin-2-yl)-2'-(1H-pyrazol-1-yl)-9H-2,9'-bicarbazole Ligand N1NPh, as a white solid (431 mg in 78% yield). $^1$H NMR (DMSO-d$_6$, 400 MHz): δ 6.50 (t, J=1.2 Hz, 1H), 7.13 (t, J=8.0 Hz, 1H), 7.41-7.46 (m, 5H), 7.51 (d, J=8.0 Hz, 1H), 7.57 (t, J=8.0 Hz, 1H), 7.61 (dd, J=8.4, 0.8 Hz, 1H), 7.68 (t, J=0.8 Hz, 1H), 7.76 (d, J=5.2 Hz, 1H), 7.81 (dd, J=8.4, 1.2 Hz, 1H), 7.87-7.88 (m, 2H), 7.91 (d, J=1.6 Hz, 1H), 7.96 (d, J=8.4 Hz, 1H), 8.08 (s, 1H), 8.21 (s, 1H), 8.27 (d, J=8.0 Hz, 1H), 8.35 (d, J=8.4 Hz, 1H), 8.40 (d, J=7.6 Hz, 1H), 8.58 (d, J=5.6 Hz, 1H), 8.59 (s, 1H), 8.70 (d, J=5.6 Hz, 1H).

9-(4-phenylpyridin-2-yl)-2'-(1H-pyrazol-1-yl)-9H-2,9'-bicarbazole Ligand N1NPh (420 mg, 0.76 mmol, 1.0 eq), K$_2$PtCl$_4$ (332 mg, 0.80 mmol, 1.05 eq), $^n$Bu$_4$NBr (25 mg, 0.076 mmol, 0.1 eq) and acetic acid (46 mL) were added to a dry pressure tube equipped with a magnetic stir bar. The mixture was bubbled with nitrogen for 30 minutes and then the tube was sealed. The mixture was stirred at room temperature for 24 hours. Then the mixture was heated to 110-115° C. in an oil bath and stirred at that temperature for 4 days. The mixture was then cooled to ambient temperature and water (60 mL) was added slowly. After stirring at room temperature for 5 minutes, the precipitate was filtered off and washed with water three times. Then the solid was dried in air under reduced pressure. The collected solid was purified through column chromatography on silica gel using dichloromethane as eluent to obtain the desired product, 9-(4-phenylpyridin-2-yl)-2'-(1H-pyrazol-1-yl)-9H-2,9'-bicarbazole platinum complex PtN1NPh, as a yellow solid (137 mg in 24% yield). FIG. 1 shows an emission spectrum of PtN1NPh in CH$_2$Cl$_2$ at room temperature. $^1$H NMR (DMSO-d$_6$, 400 MHz): δ 6.83 (t, J=2.4 Hz, 1H), 7.28 (t, J=7.6 Hz, 1H), 7.41 (t, J=7.6 Hz, 1H), 7.46-7.58 (m, 5H), 7.66-7.70 (m, 2H), 7.87-7.89 (m, 2H), 7.93 (d, J=8.0 Hz, 1H), 7.99 (d, J=8.0 Hz, 1H), 8.10 (d, J=2.0 Hz, 1H), 8.13 (d, J=8.0 Hz, 1H), 8.18 (d, J=8.0 Hz, 1H), 8.20 (d, J=8.0 Hz, 2H), 8.24 (d, J=8.4 Hz, 1H), 8.32 (d, J=1.6 Hz, 1H), 8.86 (d, J=2.8 Hz, 1H), 9.18 (d, J=6.4 Hz, 1H). $^{13}$C NMR (DMSO-d$_6$, 100 MHz): δ 106.03, 107.68, 108.32, 111.79, 113.04, 113.23, 113.58, 114.35, 115.33, 115.38, 117.04, 118.26, 118.31, 120.31, 120.48, 120.94, 122.95, 125.39, 125.62, 126.13, 127.08, 127.58, 128.89, 129.55, 130.23, 136.21, 138.00, 138.34, 138.46, 139.32, 140.19, 143.34, 143.58, 147.65, 150.01, 152.17.

Example 5

Platinum complex PtN1NCF$_3$ can be prepared according to the following scheme:

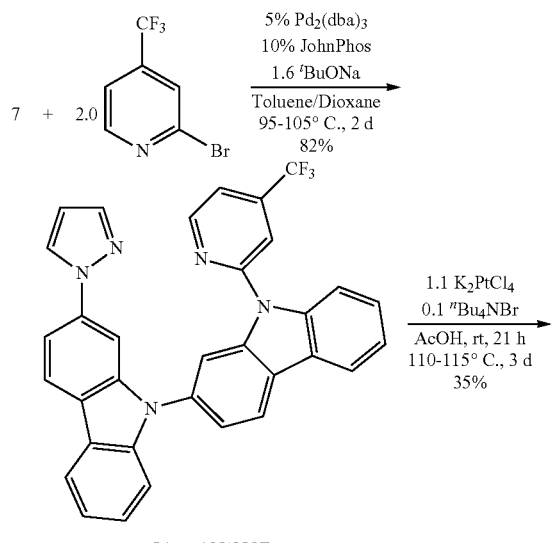

Ligand N1NCF3

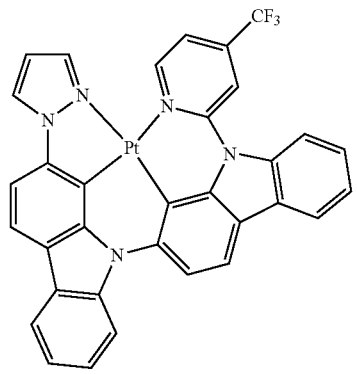

PtN1NCF3

Synthesis of 2'-(1H-pyrazol-1-yl)-9-(4-(trifluoromethyl)pyridin-2-yl)-9H-2,9'-bicarbazole Ligand N1NCF3

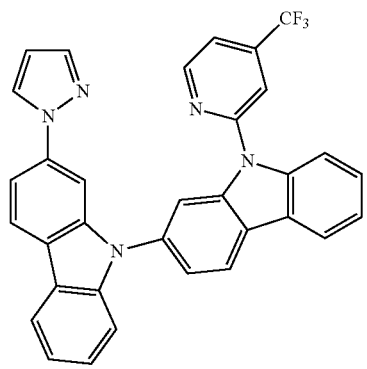 [SMILES: FC(F)(F)c1ccnc(-n2c3ccccc3c3ccc(-n4c5ccccc5c5ccc(-n6cccn6)cc54)cc32)c1]

2'-(1H-pyrazol-1-yl)-9H-2,9'-bicarbazole 7 (420 mg, 1.05 mmol, 1.0 eq), 2-bromo-4-(trifluoromethyl)pyridine (475 mg, 2.10 mmol, 2.0 eq), Pd$_2$(dba)$_3$ (48 mg, 0.05 mmol, 0.05 eq), JohnPhos (31 mg, 0.11 mmol, 0.10 eq) and $^t$BuONa (161 mg, 1.68 mmol, 1.6 eq) were added to a dry pressure Schlenk tube equipped with a magnetic stir bar. The tube was then evacuated and backfilled with nitrogen. The evacuation and backfill procedure was repeated twice, and then dry toluene (4 mL) and dioxane (4 mL) were added under nitrogen. The tube was sealed and the mixture was stirred in an oil bath at a temperature of 95-105° C. for 2 days. Then the mixture was cooled to ambient temperature. The solvent was removed under reduced pressure and the residue was purified through column chromatography on silica gel using hexane and ethyl acetate (10:1-5:1) as eluent to obtain the desired product, 2'-(1H-pyrazol-1-yl)-9-(4-(trifluoromethyl)pyridin-2-yl)-9H-2,9'-bicarbazole Ligand N1NCF3, as a brown solid (467 mg in 82% yield). $^1$H NMR (DMSO-d$_6$, 400 MHz): δ 6.45 (s, 1H), 7.25 (t, J=7.6 Hz, 1H), 7.34-7.43 (m, 3H), 7.51 (t, J=7.6 Hz, 1H), 7.57 (d, J=8.0 Hz, 1H), 7.64 (s, 1H), 7.70 (d, J=5.2 Hz, 1H), 7.76 (dd, J=8.4, 1.2 Hz, 1H), 7.85 (d, J=8.4 Hz, 1H), 7.87 (s, 1H), 8.06 (s, 1H), 8.19 (s, 1H), 8.21 (d, J=7.2 Hz, 1H), 8.29 (d, J=8.8 Hz, 1H), 8.32 (d, J=7.6 Hz, 1H), 8.49 (d, J=8.4 Hz, 1H), 8.52 (d, J=2.4 Hz, 1H), 8.84 (d, J=5.2 Hz, 1H). $^{13}$C NMR (DMSO-d$_6$, 100 MHz): δ 99.74, 107.71, 109.79, 110.29, 111.17, 111.31, 114.83 (q, J=3.9 Hz), 117.46 (q, J=3.3 Hz), 120.32, 120.43, 120.48, 120.81, 120.84, 121.45, 121.95, 122.01, 122.40, 122.53 (q, J=272.3 Hz), 123.37, 123.41, 126.19, 127.07, 128.01, 134.78, 138.45, 139.46, 139.56, 139.59 (q, J=33.5 Hz), 140.78, 141.14, 141.34, 151.32, 151.52. $^{19}$F NMR (DMSO-d$_6$, 376 MHz): δ-63.39.

Synthesis of 2'-(1H-pyrazol-1-yl)-9-(4-(trifluoromethyl)pyridin-2-yl)-9H-2,9'-bicarbazole platinum complex PtN1NCF3

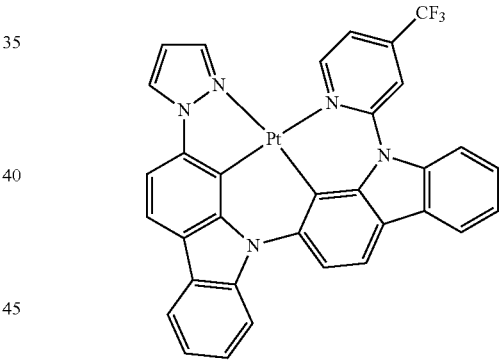

2'-(1H-pyrazol-1-yl)-9-(4-(trifluoromethyl)pyridin-2-yl)-9H-2,9'-bicarbazole Ligand N1NCF3 (405 mg, 0.745 mmol, 1.0 eq), K$_2$PtCl$_4$ (340 mg, 0.82 mmol, 1.1 eq), $^n$Bu$_4$NBr (24 mg, 0.0745 mmol, 0.1 eq) and acetic acid (45 mL) were added to a dry pressure tube equipped with a magnetic stir bar. The mixture was bubbled with nitrogen for 30 minutes and then the tube was sealed. The mixture was stirred at room temperature for 21 hours. Then the mixture was heated to 110-115° C. in an oil bath and stirred at that temperature for 3 days. The mixture was then cooled to ambient temperature and water (45 mL) was added slowly. After stirring at room temperature for 5 minutes, the precipitate was filtered off and washed with water three times. Then the solid was dried in air under reduced pressure. The collected solid was purified through column chromatography on silica gel using dichloromethane/hexane as eluent to obtain the desired product, 2'-(1H-pyrazol-1-yl)-9-(4-(trifluoromethyl)pyridin-2-yl)-9H-2,9'-bicarbazole platinum complex PtN1NCF3, as a yellow solid (190 mg in 35% yield). FIG.

1 shows an emisison spectrum of PtN1NCF₃ in CH₂Cl₂ at room temperature. ¹H NMR (DMSO-d₆, 500 MHz): δ 6.84 (t, J=2.5 Hz, 1H), 7.31 (t, J=7.5 Hz, 1H), 7.45 (t, J=7.5 Hz, 1H), 7.49-7.55 (m, 2H), 7.64 (d, J=6.5 Hz, 1H), 7.70 (d, J=8.5 Hz, 1H), 7.96 (d, J=8.0 Hz, 1H), 8.00 (d, J=8.5 Hz, 1H), 8.08-8.09 (m, 2H), 8.16 (d, J=8.5 Hz, 1H), 8.22 (t, J=8.0 Hz, 2H), 8.26 (d, J=8.5 Hz, 1H), 8.37 (s, 1H), 8.88 (d, J=2.0 Hz, 1H), 9.39 (d, J=6.5 Hz, 1H). ¹³C NMR (DMSO-d₆, 100 MHz): δ 106.03, 107.66, 108.03, 110.77, 112.70 (q, J=4.1 Hz), 113.07, 113.81, 114.12, 115.53, 115.64, 117.08, 118.34, 120.40, 120.56, 120.92, 122.51 (q, J=272.4 Hz), 123.58, 125.43, 125.64, 126.12, 127.88, 128.93, 138.00, 138.12, 138.15, 138.19 (q, J=34.4 Hz), 139.27, 140.27, 143.07, 143.31, 147.65, 153.83. ¹⁹F NMR (DMSO-d₆, 376 MHz): δ-64.04.

Example 6

Platinum complex PtON6-tBu can be prepared according to the following scheme:

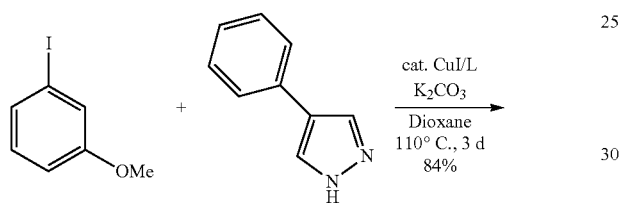

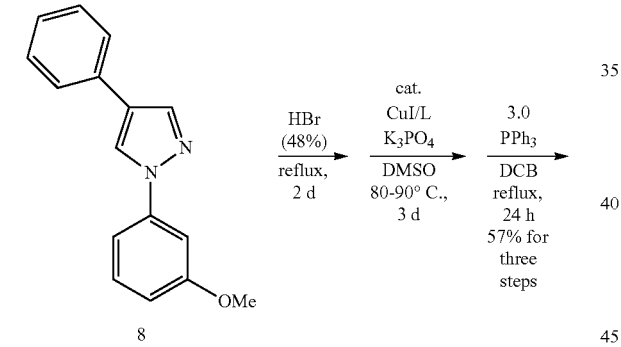

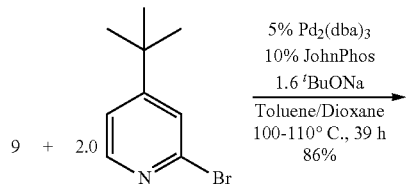

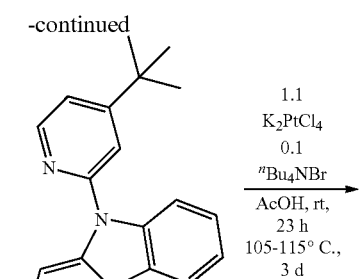

Ligand ON6-tBu

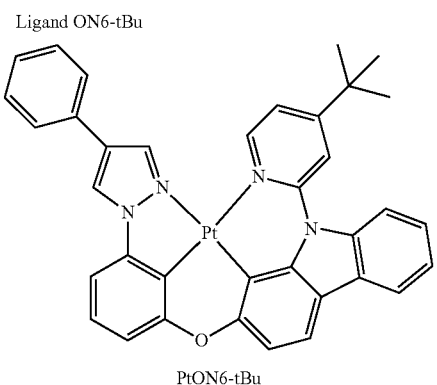

PtON6-tBu

Synthesis of 1-(3-methoxyphenyl)-4-phenyl-1H-pyrazole 8

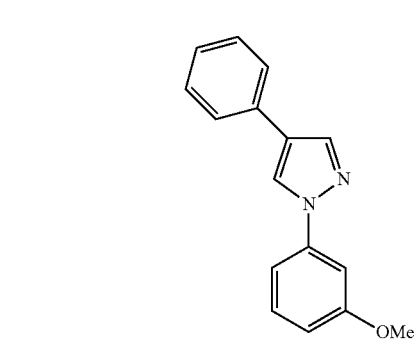 [SMILES: COc1cccc(-n2cc(-c3ccccc3)cn2)c1]

4-phenyl-1H-pyrazole (775 mg, 5.38 mmol, 1.0 eq), 1-iodo-3-methoxybenzene (1510 mg, 768 μL, 6.45 mmol, 1.2 eq), CuI (21 mg, 0.11 mmol, 0.02 eq) and K₂CO₃ (1561 mg, 11.30 mmol, 2.1 eq) were added to a dry pressure tube equipped with a magnetic stir bar. Then trans-1,2-cyclohexanediamine (123 mg, 1.08 mmol, 0.20 eq) and dioxane (12 mL) were added. The mixture was bubbled with nitrogen for 30 minutes and then the tube was sealed. The mixture was stirred in an oil bath at a temperature of 110° C. for three days and then cooled to ambient temperature. The solvent was removed under reduced pressure and the residue was purified through column chromatography on silica gel using hexane and ethyl acetate (10:1-5:1-3:1) as eluent to obtain the desired product, 1-(3-methoxyphenyl)-4-phenyl-1H-pyrazole 8, as a colorless liquid (1.13 g in 84% yield). ¹H NMR (DMSO-d₆, 400 MHz): δ 3.84 (s, 3H), 6.87-6.90 (m, 1H), 7.25 (t, J=7.2 Hz, 1H), 7.38-7.48 (m, 5H), 7.71 (d, J=7.2 Hz, 2H), 8.20 (s, 1H), 9.01 (s, 1H).

Synthesis of 2-(3-(4-phenyl-1H-pyrazol-1-yl)phenoxy)-9H-carbazole 9

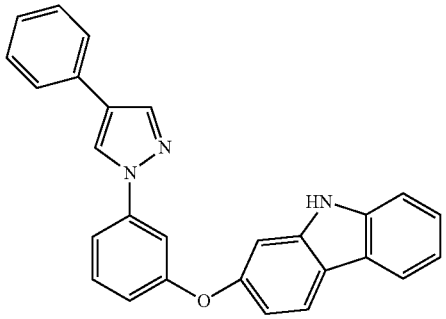 [SMILES: c1ccc(-c2cnn(-c3cccc(Oc4ccc5c(c4)[nH]c4ccccc45)c3)c2)cc1]

A solution of 1-(3-methoxyphenyl)-4-phenyl-1H-pyrazole 8 (1100 mg, 4.39 mmol) in hydrobromic acid (6 mL, 48%) was refluxed (110-120° C.) for 2 days under a nitrogen atmosphere. Then the mixture was cooled to ambient temperature and neutralized with an aqueous solution of $K_2CO_3$ until gas formation ceased. Then the precipitate was filtered off and washed with water several times and then was dried in air under reduced pressure to afford the product as a brown solid as a mixture of starting material and product (100:31 from the $^1$H NMR spectrum), which was used directly for the next steps. The brown solid, 4'-iodo-2-nitrobiphenyl (1209 mg, 3.72 mmol), CuI (30 mg, 0.16 mmol), picolinic acid (38 mg, 0.31 mmol) and $K_3PO_4$ (1316 mg, 6.20 mmol) were added to a dry Schlenk pressure tube equipped with a magnetic stir bar. The tube was evacuated and backfilled with nitrogen. The evacuation and backfill procedure was repeated twice, then DMSO (10 mL) was added and the mixture was bubbled with nitrogen for 30 minutes and the tube was sealed. The mixture was heated to 80-90° C. in an oil bath for 3 days. Then the mixture was cooled to ambient temperature, diluted with water, and extracted with ethyl acetate three times. The combined organic layer was washed with water three times, dried over sodium sulfate, then filtered and washed with ethyl acetate. The filtrate was concentrated and the residue was purified through column chromatography on silica gel using hexane and ethyl acetate (10:1-5:1-3:1) as eluent to obtain the desired product as a sticky liquid (1.13 g), which was used directly for the next step. $PPh_3$ (1997 mg, 7.61 mmol, 3.0 eq) was added to a solution of the sticky liquid (1100 mg, 2.54 mmol, 1.0 eq) in 1,2-dichlorobenzene (15 mL) under the protection of nitrogen. The mixture was heated to reflux in an oil bath and stirred at that temperature for 24 hours. The mixture was then cooled and the solvent was removed by distillation under high vacuum. The residue was purified through column chromatography on silica gel using hexane and ethyl acetate (10:1-5:1-3:1) as eluent to obtain the desired product, 2-(3-(4-phenyl-1H-pyrazol-1-yl)phenoxy)-9H-carbazole 9, as a white solid (1000 mg, 57% total yield for the three steps). $^1$H NMR (DMSO-$d_6$, 400 MHz): δ 6.96 (dd, J=8.4, 2.4 Hz, 1H), 7.01 (dd, J=8.0, 2.4 Hz, 1H), 7.16-7.19 (m, 2H), 7.25 (d, J=7.6 Hz, 1H), 7.35-7.42 (m, 3H), 7.48 (d, J=8.0 Hz, 1H), 7.54 (t, J=8.0 Hz, 1H), 7.63 (t, J=2.4 Hz, 1H), 7.68-7.72 (m, 3H), 8.10 (d, J=8.0 Hz, 1H), 8.16 (d, J=7.2 Hz, 1H), 8.19 (s, 1H), 9.05 (s, 1H), 11.26 (s, 1H).

Synthesis of 9-(4-tert-butylpyridin-2-yl)-2-(3-(4-phenyl-1H-pyrazol-1-yl)phenoxy)-9H-carbazole Ligand ON6-tBu

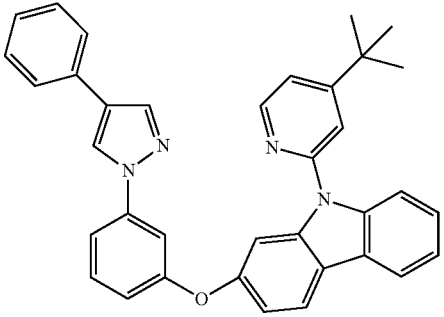 [SMILES: CC(C)(C)c1ccnc(-n2c3ccccc3c3ccc(Oc4cccc(-n5cc(-c6ccccc6)cn5)c4)cc32)c1]

2-(3-(4-phenyl-1H-pyrazol-1-yl)phenoxy)-9H-carbazole 9 (401 mg, 1.0 mmol, 1.0 eq), $Pd_2(dba)_3$ (46 mg, 0.05 mmol, 0.05 eq), JohnPhos (30 mg, 0.1 mmol, 0.1 eq) and $^t$BuONa (154 mg, 1.6 mmol, 1.6 eq) were added to a dry pressure Schlenk tube equipped with a magnetic stir bar. The tube was then evacuated and backfilled with nitrogen. The evacuation and backfill procedure was repeated twice, then dry toluene (4 mL), dioxane (4 mL) and 2-bromo-4-tert-butylpyridine (418 mg, 2.0 mmol, 2.0 eq) were added under nitrogen. The tube was sealed and the mixture was stirred in an oil bath at a temperature of 100-110° C for 39 hours. Then the mixture was cooled to ambient temperature. The solvent was removed under reduced pressure and the residue was purified through column chromatography on silica gel using hexane and ethyl acetate (20:1-15:1-10:1-5:1) as eluent to obtain the desired product, 9-(4-tert-butylpyridin-2-yl)-2-(3-(4-phenyl-1H-pyrazol-1-yl)phenoxy)-9H-carbazole Ligand ON6-tBu, as a brown solid (460 mg, 86% yield). $^1$H NMR (DMSO-$d_6$, 400 MHz): δ 1.24 (s, 9H), 7.04 (dd, J=8.0, 2.6 Hz, 1H), 7.16 (dd, J=8.4, 2.4 Hz, 1H), 7.24 (t, J=7.6 Hz, 1H), 7.32-7.47 (m, 6H), 7.53 (t, J=8.4 Hz, 1H), 7.62 (d, J=1.2 Hz, 1H), 7.66 (t, J=2.0 Hz, 1H), 7.69-7.72 (m, 3H), 7.78 (d, J=8.4 Hz, 1H), 8.19 (s, 1H), 8.24 (d, J=7.6 Hz, 1H), 8.31 (d, J=8.8 Hz, 1H), 8.57 (d, J=5.6 Hz, 1H), 9.05 (s, 1H).

Synthesis of 9-(4-tert-butylpyridin-2-yl)-2-(3-(4-phenyl-1H-pyrazol-1-yl)phenoxy)-9H-carbazole platinum complex PtON6-tBu

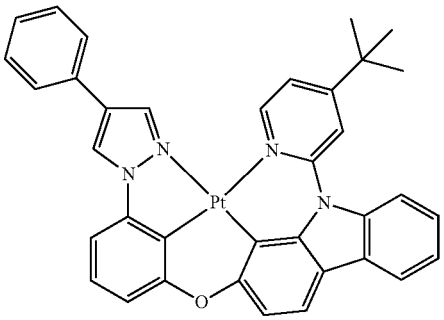

9-(4-tert-butylpyridin-2-yl)-2-(3-(4-phenyl-1H-pyrazol-1-yl)phenoxy)-9H-carbazole Ligand ON6-tBu (450 mg, 0.84 mmol, 1.0 eq), $K_2PtCl_4$ (383 mg, 0.92 mmol, 1.1 eq), "Bu₄NBr (27 mg, 0.084 mmol, 0.1 eq) and acetic acid (50 mL) were added to a dry pressure tube equipped with a magnetic stir bar. The mixture was bubbled with nitrogen for 30 minutes and then the tube was sealed. The mixture was stirred at room temperature for 23 hours. Then the mixture was heated to 105-115° C. in an oil bath and stirred at that temperature for 3 days, cooled to ambient temperature and water (50 mL) was added. After stirring at room temperature for 5 minutes, the precipitate was filtered off and washed with water three times. Then the solid was dried in air under reduced pressure. The collected solid was purified through column chromatography on silica gel using dichloromethane as eluent to obtain the desired product, 9-(4-tert-butylpyridin-2-yl)-2-(3-(4-phenyl-1H-pyrazol-1-yl)phenoxy)-9H-carbazole platinum complex PtON6-tBu, as a yellow solid (525 mg, 86% yield). FIG. 2 shows an emisison spectrum of PtON6-tBu in CH₂Cl₂ at room temperature. ¹H NMR (DMSO-d₆, 400 MHz): δ 1.40 (s, 9H), 6.99 (d, J=7.6 Hz, 1H), 7.22 (d, J=8.0 Hz, 1H), 7.27 (t, J=8.0 Hz, 1H), 7.36 (t, J=8.0 Hz, 1H), 7.42 (t, J=7.6 Hz, 1H), 7.48-7.56 (m, 5H), 7.91 (t, J=8.0 Hz, 3H), 8.10 (d, J=8.4 Hz, 1H), 8.17-8.19 (m, 2H), 8.67 (s, 1H), 9.25 (d, J=2.4 Hz, 1H), 9.42 (s, 1H). ¹³C NMR (DMSO-d₆, 100 MHz): δ 29.64, 35.46, 98.77, 106.04, 111.18, 112.39, 112.51, 113.26, 114.57, 115.60, 115.72, 118.35, 120.13, 122.88, 123.82, 124.62, 124.73, 125.41, 125.37, 127.33, 127.90, 128.99, 130.80, 136.95, 138.10, 142.01, 146.00, 147.45, 151.96, 152.29, 152.55, 163.03.

Example 7

Platinum complex PtON6Ph can be prepared according to the following scheme:

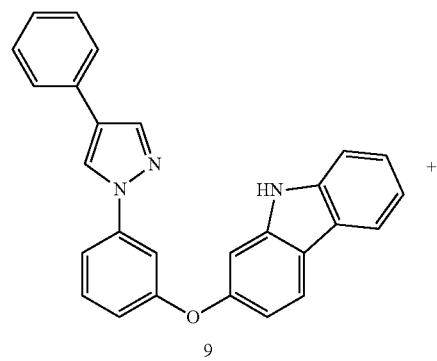

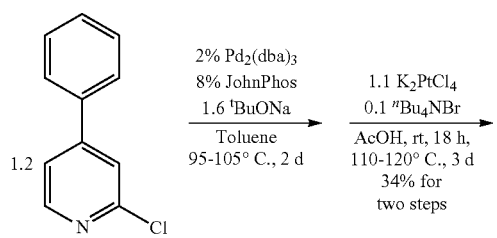

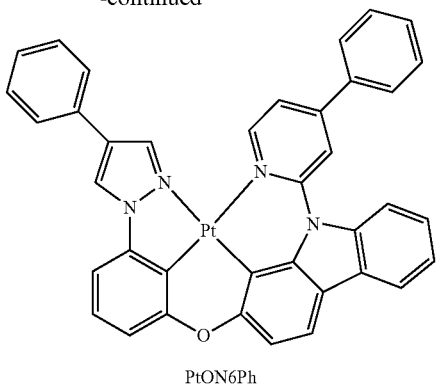

PtON6Ph

Synthesis of 2-(3-(4-phenyl-1H-pyrazol-1-yl)phenoxy)-9-(4-phenylpyridin-2-yl)-9H-carbazole platinum complex PtON6Ph

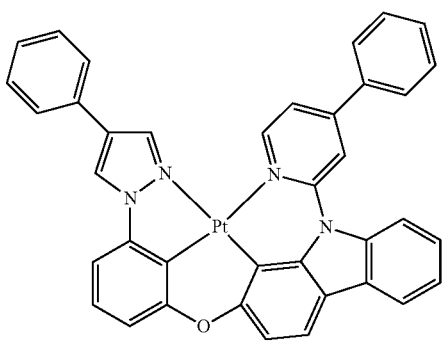

2-(3-(4-phenyl-1H-pyrazol-1-yl)phenoxy)-9H-carbazole 9 (201 mg, 0.5 mmol, 1.0 eq), 2-chloro-4-phenylpyridine (114 mg, 0.6 mmol, 1.2 eq), Pd₂(dba)₃ (9 mg, 0.02 mmol, 0.02 eq), JohnPhos (12 mg, 0.8 mmol, 0.8 eq) and ᵗBuONa (77 mg, 1.6 mmol, 1.6 eq) were added to a dry pressure Schlenk tube equipped with a magnetic stir bar. The tube was then evacuated and backfilled with nitrogen. The evacuation and backfill procedure was repeated twice, then dry toluene (2 mL) was added under nitrogen. The tube was sealed and the mixture was stirred in an oil bath at a temperature of 95-105° C. for 2 days. Then the mixture was cooled to ambient temperature. The solvent was removed under reduced pressure and the residue was purified through column chromatography on silica gel using hexane and ethyl acetate as eluent to obtain the product as a sticky liquid (209 mg) as a mixture of the starting material, 2-(3-(4-phenyl-1H-pyrazol-1-yl)phenoxy)-9H-carbazole 9, and the desired product, which was used directly for the next step. The sticky liquid (200 mg), K₂PtCl₄ (183 mg, 0.44 mmol), "Bu₄NBr (13 mg, 0.04 mmol) and acetic acid (24 mL) were added to a dry pressure tube equipped with a magnetic stir bar. The mixture was bubbled with nitrogen for 30 minutes and then the tube was sealed. The mixture was stirred at room temperature for 18 hours. Then the mixture was heated to 110-120° C. in an oil bath and stirred at that temperature for another 3 days. The mixture was then cooled to ambient temperature and water (25 mL) was added. After stirring at room temperature for 5 minutes, the precipitate was filtered off and washed with water three times. Then the solid was dried in air under reduced pressure. The collected solid was purified through column chromatography on silica gel using hexane and dichloromethane (2:3) as eluent to obtain the desired product, 2-(3-(4-phenyl-1H-pyrazol-1-yl)phenoxy)-9-(4-phenylpyridin-2-yl)-9H-carbazole platinum complex PtON6Ph, as a yellow solid (127 mg, 34% total yield for the two steps). FIG. 2 shows an emisison spectrum of PtON6Ph in $CH_2Cl_2$ at room temperature. $^1$H NMR (DMSO-$d_6$, 400 MHz): δ 7.02 (d, J=8.0 Hz, 1H), 7.24 (d, J=8.4 Hz, 1H), 7.29 (t, J=8.0 Hz, 1H), 7.37 (t, J=7.2 Hz, 1H), 7.44 (t, J=7.2 Hz, 1H), 7.49-7.64 (m, 7H), 7.80 (dd, J=6.4, 1.6 Hz, 1H), 7.91-7.97 (m, 5H), 8.19 (d, J=7.6 Hz, 1H), 8.26 (d, J=8.0 Hz, 1H), 8.44 (d, J=2.0 Hz, 1H), 8.72 (s, 1H) 9.40 (d, J=6.4 Hz, 1H), 9.44 (s, 1H).

Example 8

Platinum complex PtON1 can be prepared according to the following scheme:

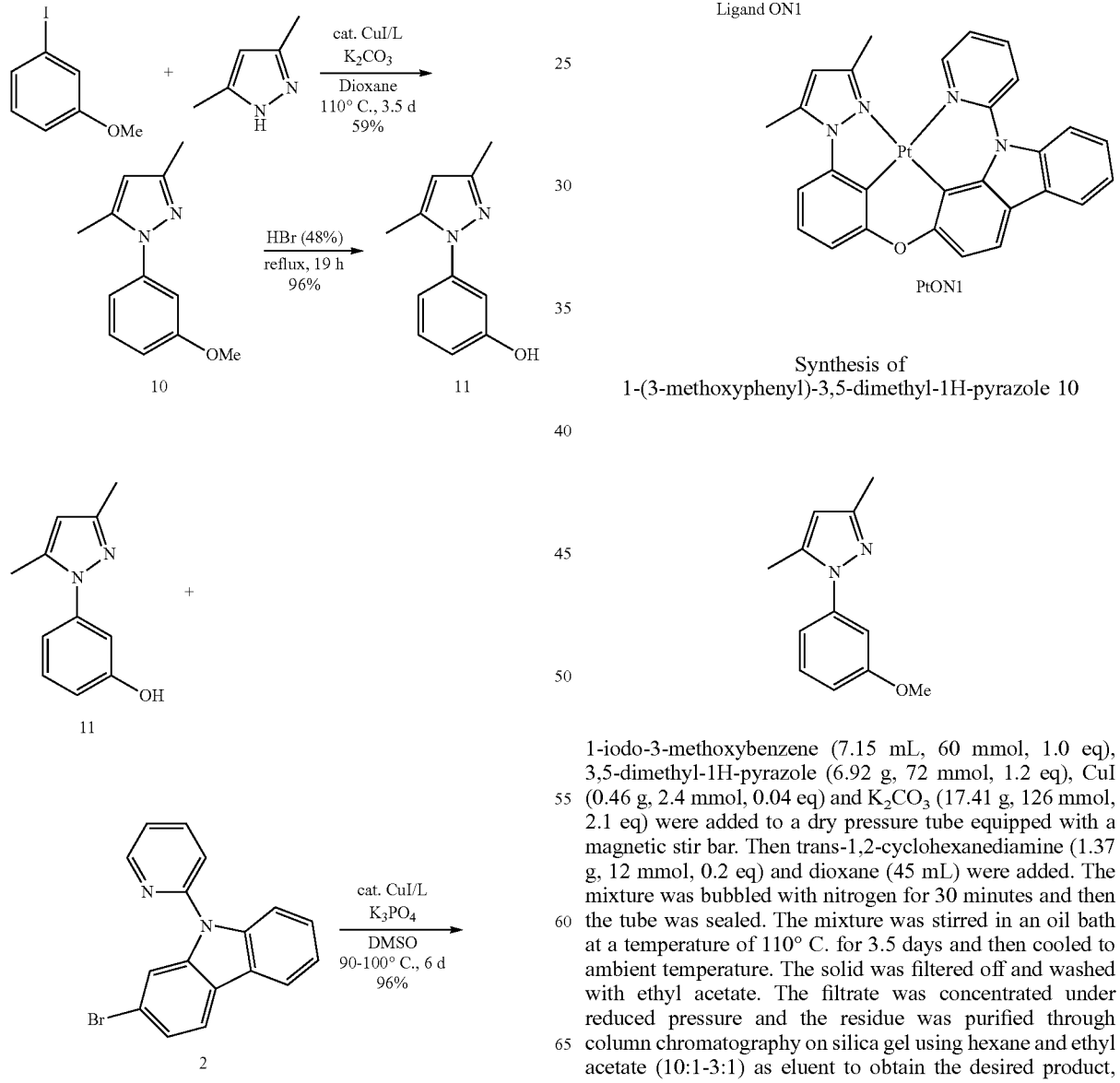

Synthesis of 1-(3-methoxyphenyl)-3,5-dimethyl-1H-pyrazole 10

1-iodo-3-methoxybenzene (7.15 mL, 60 mmol, 1.0 eq), 3,5-dimethyl-1H-pyrazole (6.92 g, 72 mmol, 1.2 eq), CuI (0.46 g, 2.4 mmol, 0.04 eq) and $K_2CO_3$ (17.41 g, 126 mmol, 2.1 eq) were added to a dry pressure tube equipped with a magnetic stir bar. Then trans-1,2-cyclohexanediamine (1.37 g, 12 mmol, 0.2 eq) and dioxane (45 mL) were added. The mixture was bubbled with nitrogen for 30 minutes and then the tube was sealed. The mixture was stirred in an oil bath at a temperature of 110° C. for 3.5 days and then cooled to ambient temperature. The solid was filtered off and washed with ethyl acetate. The filtrate was concentrated under reduced pressure and the residue was purified through column chromatography on silica gel using hexane and ethyl acetate (10:1-3:1) as eluent to obtain the desired product, 1-(3-methoxyphenyl)-3,5-dimethyl-1H-pyrazole 10, as a brown liquid (7.12 g, 59% yield). $^1$H NMR (DMSO-d$_6$, 400 MHz): δ 2.18 (s, 3H), 2.30 (s, 3H), 3.80 (s, 3H), 6.06 (s, 1H), 6.95 (dd, J=8.0, 2.4 Hz, 1H), 7.02-7.06 (m, 2H), 7.39 (t, J=8.0 Hz, 1H).

Synthesis of 3-(3,5-dimethyl-1H-pyrazol-1-yl)phenol 11

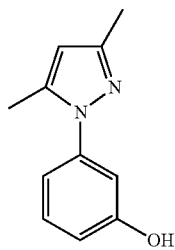

A solution of 1-(3-methoxyphenyl)-3,5-dimethyl-1H-pyrazole 10 (7.10 g, 35.11 mmol) in hydrobromic acid (45 mL, 48%) was refluxed (110-120° C.) for 19 hours a nitrogen atmosphere. Then the mixture was cooled to ambient temperature and neutralized with an aqueous solution of K$_2$CO$_3$ until gas formation ceased. Then the precipitate was filtered off and washed with water several times. The collected solid was dried in air to afford the product as a brown solid (6.33 g in 96% yield). $^1$H NMR (DMSO-d$_6$, 400 MHz): δ 2.16 (s, 3H), 2.28 (s, 3H), 6.04 (s, 1H), 6.75-6.77 (m, 1H), 6.86-6.89 (m, 2H), 7.26 (t, J=8.0 Hz, 1H), 9.73 (s, 1H). $^{13}$C NMR (DMSO-d$_6$, 100 MHz): δ 12.29, 13.30, 107.07, 111.10, 113.94, 114.43, 129.71, 138.95, 140.70, 147.57, 157.84.

Synthesis of 2-(3-(3,5-dimethyl-1H-pyrazol-1-yl)phenoxy)-9-(pyridin-2-yl)-9H-carbazole Ligand ON1

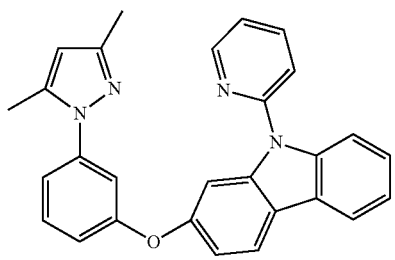 [SMILES: Cc1cc(C)n(-c2cccc(Oc3ccc4c5ccccc5n(-c5ccccn5)c4c3)c2)n1]

3-(3,5-dimethyl-1H-pyrazol-1-yl)phenol 11 (1.27 g, 6.75 mmol, 1.0 eq), 2-bromo-9-(pyridin-2-yl)-9H-carbazole 2 (2.62 g, 8.10 mmol, 1.2 eq), CuI (0.13 g, 0.675 mmol, 0.1 eq), picolinic acid (0.17 g, 1.35 mmol, 0.2 eq), K$_3$PO$_4$ (2.87 g, 13.50 mmol, 2.0 eq) and DMSO (20 mL) were added to a dry pressure vessel equipped with a magnetic stir bar. The mixture was bubbled with nitrogen for 30 minutes and then vessel was sealed. The mixture was stirred in an oil bath at a temperature of 90-100° C. for 6 days and then cooled to ambient temperature and diluted with ethyl acetate. The solid was filtered off and washed with ethyl acetate. The filtrate was then washed with water three times, dried over sodium sulfate, filtered, and the solvent was removed under reduced pressure. The residue was purified through column chromatography on silica gel using hexane/ethyl acetate (10:1-3:1-2:1) as eluent to obtain the desired product as a colorless sticky liquid (2.80 g in 96% yield). $^1$H NMR (DMSO-d$_6$, 400 MHz): δ 2.11 (s, 3H), 2.24 (s, 3H), 6.01 (s, 1H), 7.02-7.04 (m, 1H), 7.07-7.11 (m, 2H), 7.21-7.24 (m, 1H), 7.33 (t, J=7.6 Hz, 1H), 7.41-7.48 (m, 3H), 7.53 (d, J=2.4 Hz, 1H), 7.76 (d, J=8.8 Hz, 2H), 8.07 (td, J=7.6, 2.0 Hz, 1H), 8.21 (d, J=8.0 Hz, 1H), 8.27 (d, J=8.4 Hz, 1H), 8.66-8.68 (m, 1H). $^{13}$C NMR (DMSO-d$_6$, 100 MHz): δ 12.21, 13.23, 102.42, 107.48, 111.10, 113.25, 113.32, 116.26, 118.25, 119.04, 120.03, 120.19, 121.25, 121.79, 122.13, 123.24, 125.98, 130.41, 139.24, 139.34, 139.51, 139.92, 140.93, 148.08, 149.52, 150.45, 154.77, 157.93.

Synthesis of 2-(3-(3,5-dimethyl-1H-pyrazol-1-yl)phenoxy)-9-(pyridin-2-yl)-9H-carbazole platinum complex PtON1

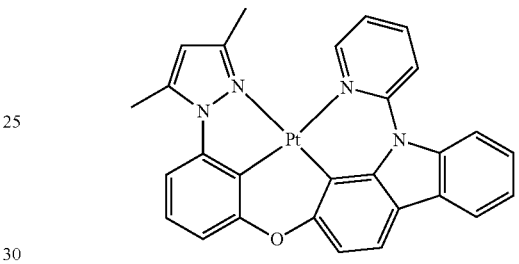

2-(3-(3,5-dimethyl-1H-pyrazol-1-yl)phenoxy)-9-(pyridin-2-yl)-9H-carbazole Ligand ON1 (1340 mg, 3.11 mmol, 1.0 eq), K$_2$PtCl$_4$ (1356 mg, 3.27 mmol, 1.05 eq), $^n$Bu$_4$NBr (100 mg, 0.31 mmol, 0.1 eq) and acetic acid (187 mL, 60 mL/mmol ligand) were added to a dry pressure tube equipped with a magnetic stir bar. The mixture was bubbled with nitrogen for 30 minutes and then the tube was sealed. The mixture was stirred at room temperature for 48 hours and then in an oil bath at a temperature of 105-115° C. for an additional 3 days. Then mixture was cooled to ambient temperature and water (373 mL, 120 mL/mmol ligand) was added. The mixture was stirred at room temperature for 5 minutes, then the precipitate was filtered off and washed with water three times. Then the solid was dried in air under reduced pressure. The collected solid was purified through column chromatography on silica gel using dichloromethane as eluent to obtain the title compound as a yellow solid (1057 mg in 55% yield). FIG. 3 shows an emisison spectrum of PtON1 in CH$_2$Cl$_2$ at room temperature. $^1$H NMR (DMSO-d$_6$, 400 MHz): δ 2.40 (s, 3H), 2.73 (s, 3H), 6.42 (s, 1H), 6.96 (d, J=8.0, 1H), 7.18 (d, J=8.4, 1H), 7.22 (d, J=8.0, 1H), 7.26-7.30 (m, 2H), 7.39 (t, J=7.6, 1H), 7.47 (t, J=7.6 Hz, 1H), 7.85 (d, J=7.6 Hz, 1H), 8.08 (d, J=8.0, 1H), 8.11-8.19 (m, 3H), 9.24 (d, J=4.8 Hz, 1H). $^{13}$C NMR (DMSO-d$_6$, 100 MHz): δ 14.31, 14.36, 100.17, 107.12, 110.29, 110.97, 112.18, 112.40, 115.07, 115.29, 115.68, 115.71, 119.02, 119.93, 122.85, 124.46, 124.70, 127.95, 137.84, 140.14, 141.87, 141.93, 147.40, 147.98, 149.66, 151.61, 151.99, 153.78.

Example 9

Platinum complex PtON1Me[4] can be prepared according to the following scheme:

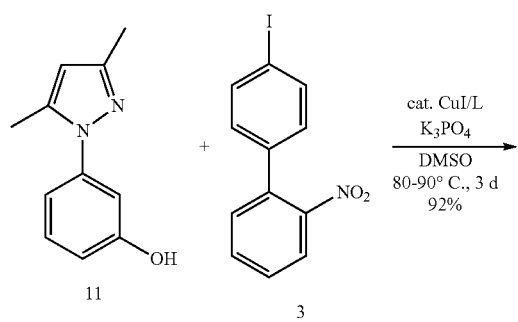

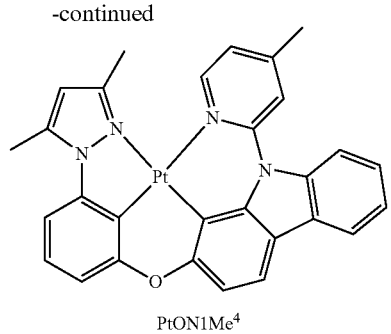

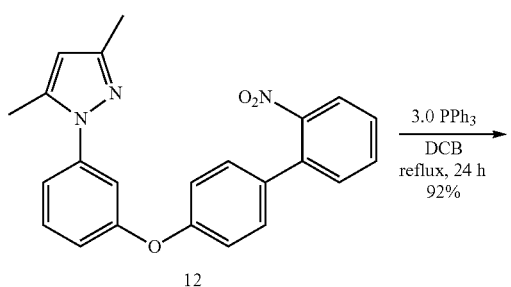

Synthesis of 3,5-dimethyl-1-(3-(2'-nitrobiphenyl-4-yloxy)phenyl)-1H-pyrazole 12

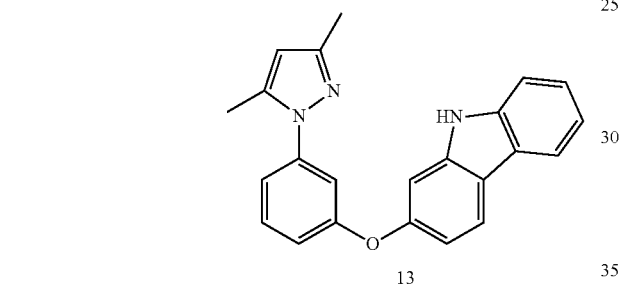

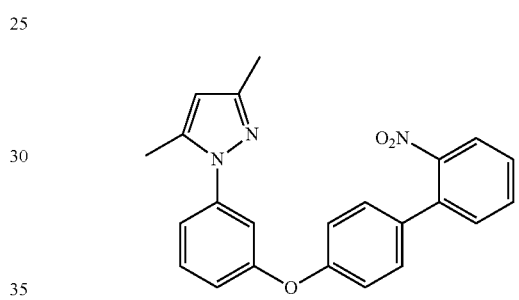

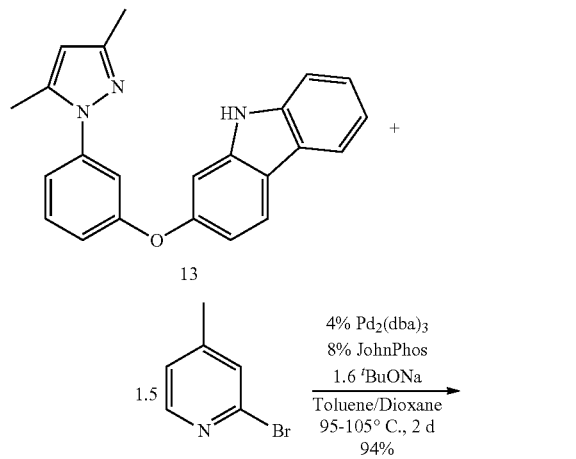

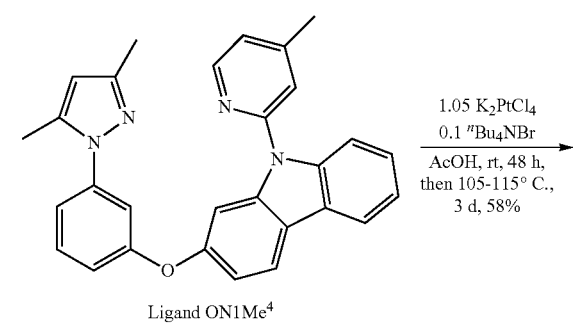

3-(3,5-dimethyl-1H-pyrazol-1-yl)phenol 11 (5.00 g, 26.56 mmol, 1.0 eq), 4'-iodo-2-nitrobiphenyl 3 (10.38 g, 31.92 mmol, 1.2 eq), CuI (0.25 g, 1.33 mmol, 0.05 eq), picolinic acid (0.33 g, 2.66 mmol, 0.1 eq), $K_3PO_4$ (11.28 g, 53.12 mmol, 2.0 eq) and DMSO (60 mL) were added to a dry pressure tube equipped with a magnetic stir bar. The mixture was bubbled with nitrogen for 30 minutes and then the tube was sealed. The mixture was stirred in an oil bath at a temperature of 80-90° C. for three days and then cooled to ambient temperature. The solid was filtered off and washed with ethyl acetate (250 mL). The filtrate was then washed with water three times, dried over sodium sulfate, filtered, and the solvent was removed under reduced pressure. The residue was purified through column chromatography on silica gel using hexane/ethyl acetate (10:1-5:1-3:1 as eluent to obtain the desired product as a sticky liquid (9.38 g in 92% yield). $^1$H NMR (DMSO-$d_6$, 400 MHz): δ 2.15 (s, 3H), 2.30 (s, 3H), 6.06 (s, 1H), 7.07 (dd, J=8.0, 2.4 Hz, 1H), 7.13-7.16 (m, 3H), 7.30-7.32 (m, 1H), 7.36-7.40 (m, 2H), 7.52 (t, J=8.0, 1H), 7.57 (dd, J=7.6, 1.2 Hz, 1H), 7.59-7.64 (m, 1H), 7.75 (td, J=7.6, 1.2 Hz, 1H), 7.97 (dd, J=8.0, 1.2 Hz, 1H). $^{13}$C NMR (DMSO-$d_6$, 100 MHz): δ 12.30, 13.27, 107.63, 114.22, 117.18, 118.91, 118.97, 124.10, 128.81, 129.73, 130.61, 131.84, 132.28, 132.92, 134.33, 139.35, 141.11, 148.20, 148.92, 156.52, 156.67.

Synthesis of 2-(3-(3,5-dimethyl-1H-pyrazol-1-yl)phenoxy)-9H-carbazole 13

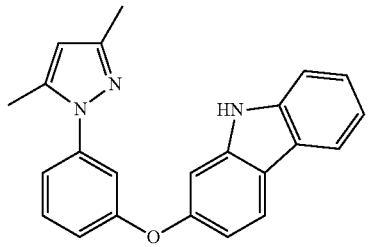 [SMILES: Cc1cc(C)n(-c2cccc(Oc3ccc4c(c3)[nH]c3ccccc34)c2)n1]

A solution of 3,5-dimethyl-1-(3-(2'-nitrobiphenyl-4-yloxy)phenyl)-1H-pyrazole 12 (2.19 g, 5.68 mmol, 1.0 eq) and PPh$_3$ (4.47 g, 17.04 mmol, 3.0 eq) in 1,2-dichlorobenzene (30 mL) was refluxed (175-185° C.) in an oil bath for 24 hours. The mixture was then cooled down and the solvent was removed by distillation under high vacuum. The residue was purified through column chromatography on silica gel using hexane/ethyl acetate (10:1-5:1) as eluent to obtain the desired product, 2-(3-(3,5-dimethyl-1H-pyrazol-1-yl)phenoxy)-9H-carbazole 13, as a white solid (1.83 g in 92% yield). $^1$H NMR (DMSO-d$_6$, 400 MHz): δ 2.11 (s, 3H), 2.28 (s, 3H), 6.02 (s, 1H), 6.92 (dd, J=8.4, 2.0 Hz, 1H), 7.05 (dd, J=8.4, 2.4 Hz, 1H), 7.10 (t, J=2.0 Hz, 1H), 7.13-7.16 (m, 2H), 7.22-7.25 (m, 1H), 7.32-7.36 (m, 1H), 7.46 (d, J=8.0, 1H), 7.47 (t, J=8.4 Hz, 1H), 8.07 (d, J=7.2 Hz, 1H), 8.12 (d, J=8.4 Hz, 1H), 11.25 (s, 1H). $^{13}$C NMR (DMSO-d$_6$, 100 MHz): δ 12.30, 13.24, 101.46, 107.52, 110.92, 111.10, 113.37, 116.43, 118.09, 118.87, 119.12, 119.88, 121.50, 122.23, 125.23, 130.36, 139.24, 140.17, 140.68, 140.99, 148.10, 154.44, 158.21.

Synthesis of 2-(3-(3,5-dimethyl-1H-pyrazol-1-yl)phenoxy)-9-(4-methylpyridin-2-yl)-9H-carbazole Ligand ON1Me$^4$

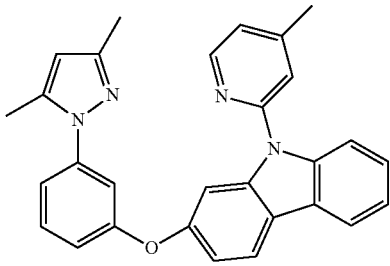 [SMILES: Cc1ccnc(-n2c3ccccc3c3ccc(Oc4cccc(-n5nc(C)cc5C)c4)cc32)c1]

2-(3-(3,5-dimethyl-1H-pyrazol-1-yl)phenoxy)-9H-carbazole 13 (530 mg, 1.5 mmol, 1.0 eq), Pd$_2$(dba)$_3$ (55 mg, 0.06 mmol, 0.04 eq), JohnPhos (36 mg, 0.12 mmol, 0.08 eq) and $^t$BuONa (231 mg, 2.4 mmol, 1.6 eq) were added to a dry pressure Schlenk tube equipped with a magnetic stir bar. The tube was evacuated and back-filled with nitrogen. The evacuation/back-fill procedure was repeated twice then toluene (6 mL, 4 mL/mmol 13), dioxane (6 mL, 4 mL/mmol 13) and 2-bromo-4-methylpyridine (387 mg, 2.25 mmol, 1.5 eq) were added under nitrogen. The tube was sealed and the mixture was stirred in an oil bath at a temperature of 95-105° C. for 2 days. Then the mixture was cooled to ambient temperature. The solvent was removed under reduced pressure and the residue was purified through column chromatography on silica gel using hexane/ethyl acetate (10:1-4:1) as eluent to obtain the title compound as a colorless solid (628 mg in 94% yield). $^1$H NMR (DMSO-d$_6$, 400 MHz): δ 2.14 (s, 3H), 2.28 (s, 3H), 2.46 (s, 3H), 6.05 (s, 1H), 7.06 (dd, J=8.0, 2.4 Hz, 1H), 7.09-7.13 (m, 2H), 7.26 (dt, J=8.0, 1.2 Hz, 1H), 7.31 (d, J=5.2 Hz, 1H), 7.35 (t, J=7.2 Hz, 1H), 7.44-7.52 (m, 3H), 7.61 (s, 1H), 7.78 (d, J=8.0, 1H), 8.24 (d, J=8.0 Hz, 1H), 8.29 (d, J=8.8 Hz, 1H), 8.53 (d, J=4.8 Hz, 1H). $^{13}$C NMR (DMSO-d$_6$, 100 MHz): δ 12.22, 13.22, 20.58, 102.38, 107.48, 111.18, 113.15, 113.29, 116.34, 118.25, 119.48, 119.91, 120.15, 121.12, 121.76, 123.14, 123.16, 125.92, 130.39, 139.24, 139.38, 139.98, 140.93, 148.07, 149.07, 150.47, 150.70, 154.79, 157.90.

Synthesis of 2-(3-(3,5-dimethyl-1H-pyrazol-1-yl)phenoxy)-9-(4-methylpyridin-2-yl)-9H-carbazole platinum complex PtON1Me$^4$

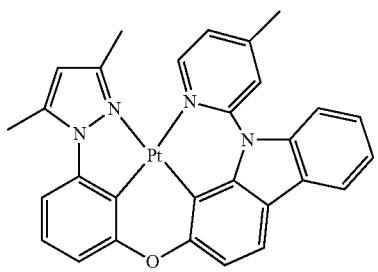

Figure 5:
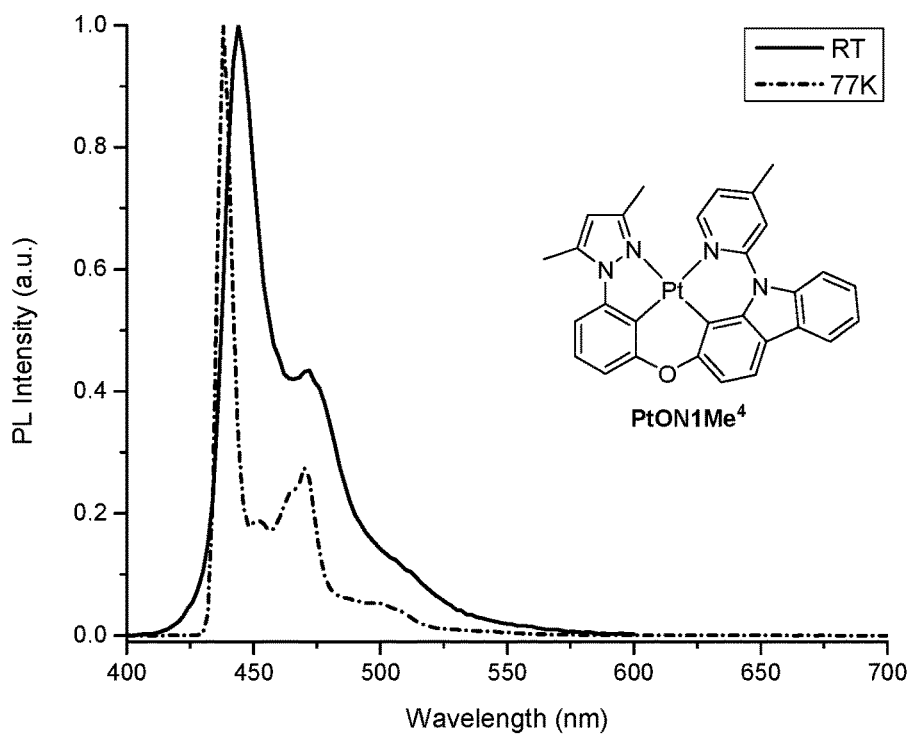
FIG. 5 shows emission spectra of PtON1Me$^4$ in CH$_2$Cl$_2$ at room temperature and in 2-methyl-THF at 77 K.

PtON1Me$^4$ was synthesized according to the procedure of synthesis of PtON1. 2-(3-(3,5-Dimethyl-1H-pyrazol-1-yl)phenoxy)-9-(4-methylpyridin-2-yl)-9H-carbazole Ligand ON1Me$^4$ (595 mg, 1.34 mmol, 1.0 eq) was reacted with K$_2$PtCl$_2$ (583 mg, 1.41 mmol, 1.05 eq) in the presence of $^n$Bu$_4$NBr (42 mg, 0.13 mmol, 0.1 eq) at room temperature for 19 hours and then at 105-115° C. for an additional 3 days. Purification of the crude product by flash chromatography on silica gel (eluent: dichloromethane) afforded the title compound as a yellow solid (496 mg in 58% yield). FIG. 3 shows an emisison spectrum of PtOMe$^4$ in CH$_2$Cl$_2$ at room temperature. Emission spectra of PtON1Me$^4$ at room temperature in CH$_2$Cl$_2$ and at 77 K in 2-methyl-THF are shown in FIG. 5. $^1$H NMR (DMSO-d$_6$, 400 MHz): δ 2.36 (s, 3H), 2.37 (s, 3H), 2.70 (s, 3H), 6.38 (s, 1H), 6.91 (d, J=7.6, 1H), 7.10 (d, J=7.0, 1H), 7.13 (d, J=8.0, 1H), 7.17 (t, J=8.0, 1H), 7.23 (d, J=7.2, 1H), 7.36 (t, J=7.6, 1H), 7.45 (t, J=7.6, 1H), 7.80 (d, J=8.0 Hz, 1H), 7.94 (s, 1H), 8.09 (t, J=8.4 Hz, 2H), 9.03 (d, J=6.0 Hz, 1H). $^1$H NMR (CD$_2$Cl$_2$, 400 MHz): δ 2.28 (s, 3H), 2.38 (s, 3H), 2.67 (s, 3H), 6.09 (s, 1H), 6.76 (d, J=6.4, 1H), 7.05 (d, J=8.0, 1H), 7.17 (d, J=7.6, 1H), 7.22 (t, J=7.6, 1H), 7.29 (d, J=8.0, 1H), 7.38 (t, J=7.2 Hz, 1H), 7.44 (d, J=7.6 Hz, 1H), 7.81 (d, J=8.0, 1H), 7.88 (s, 1H), 7.96 (d, J=8.0, 1H), 8.06 (d, J=7.6, 1H), 8.96 (d, J=6.4, 1H). $^{13}$C NMR (CD$_2$Cl$_2$, 100 MHz): δ 14.85, 15.08, 21.59, 100.57, 107.22, 110.31, 111.81, 112.82, 113.15, 115.15, 115.35, 115.95, 116.37, 119.99, 120.19, 122.99, 124.32, 124.67, 129.27, 138.89, 141.95, 143.16, 148.40, 149.13, 149.89, 151.37, 152.76, 153.18, 153.21.

Example 10

Platinum complex PtON1Me$^5$ can be prepared according to the following scheme:

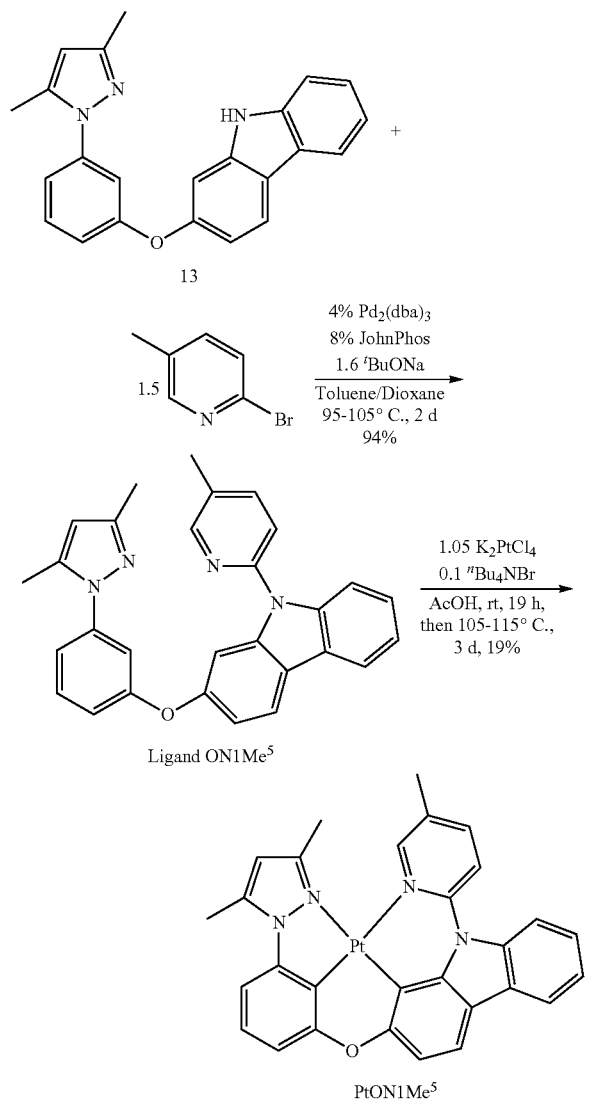

Synthesis of 2-(3-(3,5-dimethyl-1H-pyrazol-1-yl)phenoxy)-9-(5-methylpyridin-2-yl)-9H-carbazole Ligand ON1Me⁵

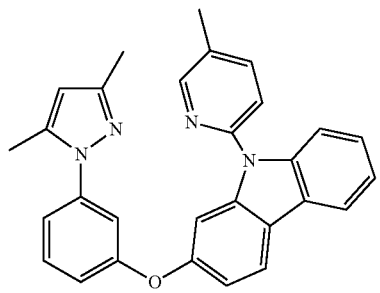 [SMILES: Cc1ccc(-n2c3ccccc3c3ccc(Oc4cccc(-n5nc(C)cc5C)c4)cc32)nc1]

Ligand ON1Me⁵ was synthesized according to the procedure of synthesis of Ligand ON1Me⁴ using 2-(3-(3,5-Dimethyl-1H-pyrazol-1-yl)phenoxy)-9H-carbazole 13 (353 mg, 1.0 mmol, 1.0 eq) and 2-bromo-5-methylpyridine (258 mg, 1.5 mmol, 1.5 eq). Purification of the crude product by flash chromatography on silica gel (eluent: hexane/ethyl acetate=10:1-5:1) afforded the title compound as a colorless solid (420 mg in 94% yield). ¹H NMR (DMSO-$d_6$, 400 MHz): δ 2.12 (s, 3H), 2.25 (s, 3H), 2.39 (s, 3H), 6.03 (s, 1H), 7.04 (dd, J=8.0, 2.4 Hz, 1H), 7.07-7.11 (m, 2H), 7.23 (dd, J=8.0, 2.0 Hz, 1H), 7.32 (t, J=7.6 Hz, 1H), 7.41-7.49 (m, 3H), 7.66 (d, J=8.4 Hz, 1H), 7.71 (d, J=8.0, 1H), 7.89 (dd, J=8.0, 2.0 Hz, 1H), 8.22 (d, J=7.2 Hz, 1H), 8.27 (d, J=8.0 Hz, 1H), 8.50 (d, J=2.0 Hz, 1H). ¹³C NMR (DMSO-$d_6$, 125 MHz): δ 12.21, 13.23, 17.48, 102.16, 107.49, 110.95, 113.14, 113.26, 116.28, 118.26, 118.64, 119.87, 120.19, 121.04, 121.80, 123.07, 125.92, 130.42, 131.64, 139.25, 139.49, 139.79, 140.05, 140.92, 148.09, 148.10, 149.50, 154.74, 157.95.

Synthesis of 2-(3-(3,5-dimethyl-1H-pyrazol-1-yl)phenoxy)-9-(5-methylpyridin-2-yl)-9H-carbazole platinum complex PtON1Me⁵

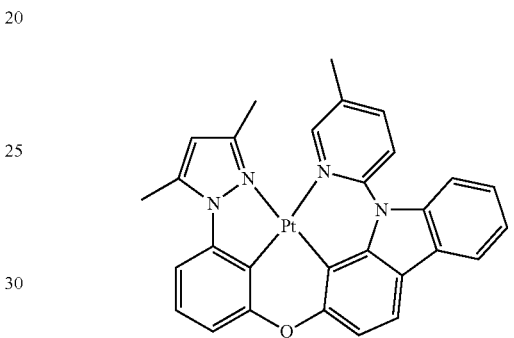

Figure 6:
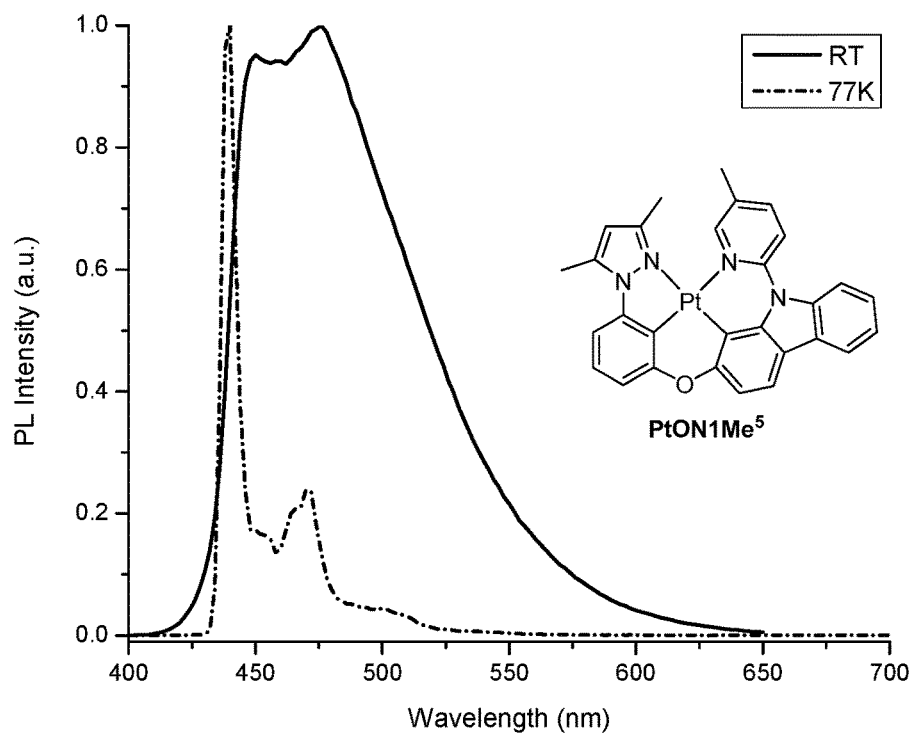
FIG. 6 shows emission spectra of PtON1Me$^5$ in CH$_2$Cl$_2$ at room temperature and in 2-methyl-THF at 77 K.
Figure 7:
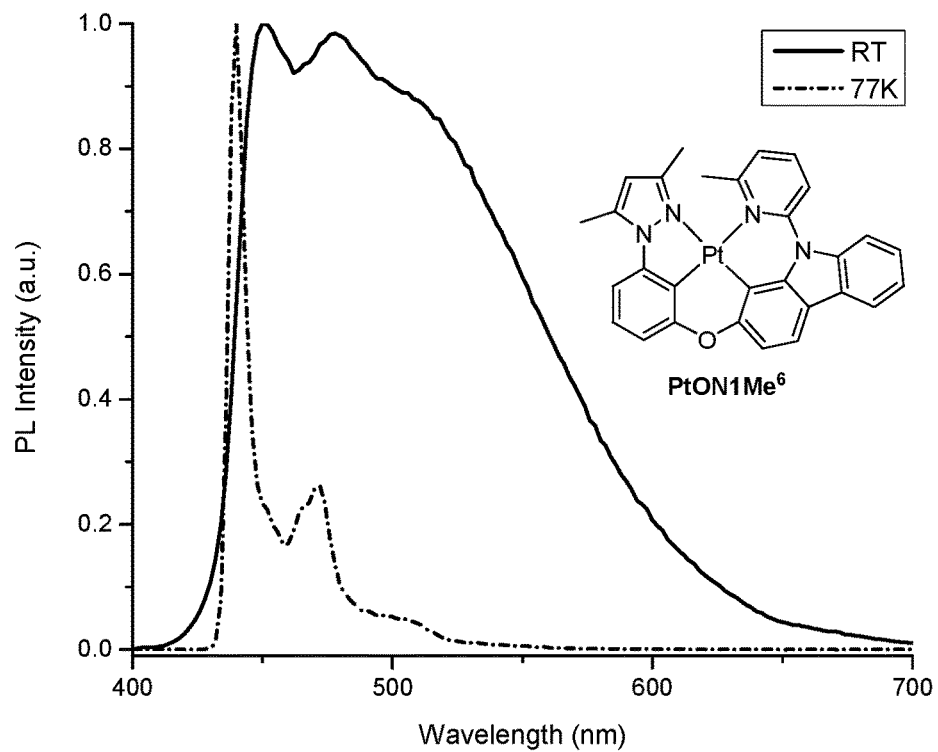
FIG. 7 shows emission spectra of PtON1Me$^6$ in CH$_2$Cl$_2$ at room temperature and in 2-methyl-THF at 77 K.
Figure 8:
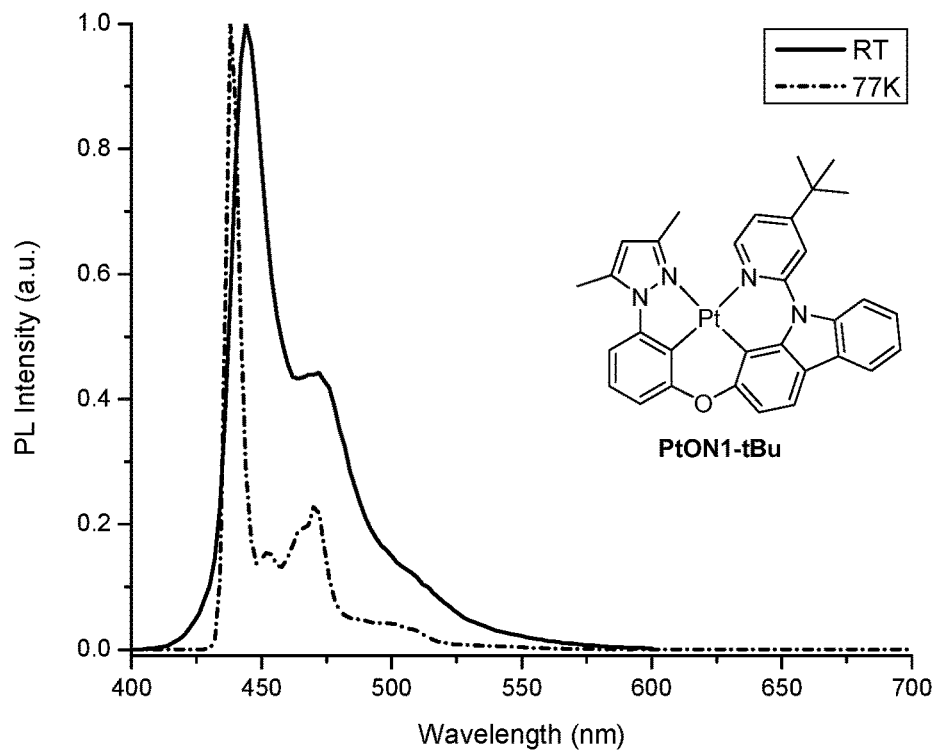
FIG. 8 shows emission spectra of PtON1-tBu in CH$_2$Cl$_2$ at room temperature and in 2-methyl-THF at 77 K.

PtON1Me⁵ was synthesized according to the procedure of synthesis of PtON1. 2-(3-(3,5-Dimethyl-1H-pyrazol-1-yl)phenoxy)-9-(5-methylpyridin-2-yl)-9H-carbazole Ligand ON1Me⁵ (410 mg, 0.92 mmol, 1.0 eq) was reacted with $K_2PtCl_2$ (402 mg, 0.97 mmol, 1.05 eq) in the presence of ⁿBu₄NBr (30 mg, 0.092 mmol, 0.1 eq) at room temperature for 19 hours and then at 105-115° C. for an additional 3 days. Purification of the crude product by flash chromatography on silica gel (eluent: hexane/dichloromethane=1:1) afforded the title compound as a yellow solid (111 mg in 19% yield). FIG. 3 shows an emission spectrum of PtON1M⁵ at room temperature. Emission spectra of PtON1Me⁵ at room temperature in $CH_2Cl_2$ and at 77 K in 2-methyl-THF are shown in FIG. 6. ¹H NMR ($CD_2Cl_2$, 400 MHz): δ 2.34 (s, 3H), 2.47 (s, 3H), 2.74 (s, 3H), 6.20 (s, 1H), 7.00-7.03 (m, 1H), 7.20-7.26 (m, 3H), 7.35-7.39 (m, 1H), 7.41-7.46 (m, 1H), 7.74 (d, J=9.2 Hz, 1H), 7.77 (dd, J=8.0, 1.6 Hz, 1H), 7.94 (d, J=8.4 Hz, 1H), 8.05 (d, J=8.4 Hz, 2H), 9.09 (s, 1H). ¹H NMR (DMSO-$d_6$, 400 MHz): δ 2.40 (s, 3H), 2.43 (s, 3H), 2.77 (s, 3H), 6.47 (s, 1H), 6.96 (d, J=8.0 Hz, 1H), 7.17 (d, J=8.4 Hz, 1H), 7.23 (t, J=8.0 Hz, 1H), 7.29 (d, J=8.0 Hz, 1H), 7.40 (d, J=8.4 Hz, 1H), 7.47-7.51 (m, 1H), 7.85 (d, J=8.0 Hz, 1H), 8.02 (dd, J=8.4, 2.0 Hz, 1H), 8.08 (d, J=7.6 Hz, 1H), 8.13 (d, J=8.4 Hz, 1H), 8.15 (d, J=8.4 Hz, 1H), 9.09 (d, J=1.6 Hz, 1H). ¹³C NMR ($CD_2Cl_2$, 100 MHz): δ 14.72, 15.16, 17.67, 100.21, 107.25, 110.41, 111.44, 112.78, 113.27, 114.93, 115.44, 115.58, 116.30, 120.23, 122.93, 124.33, 124.79, 128.05, 129.20, 138.97, 140.30, 142.11, 143.10, 147.68, 148.41, 149.93, 152.76, 153.20, 153.43.

Example 11

Platinum complex PtON1Me⁶ can be prepared according to the following scheme:

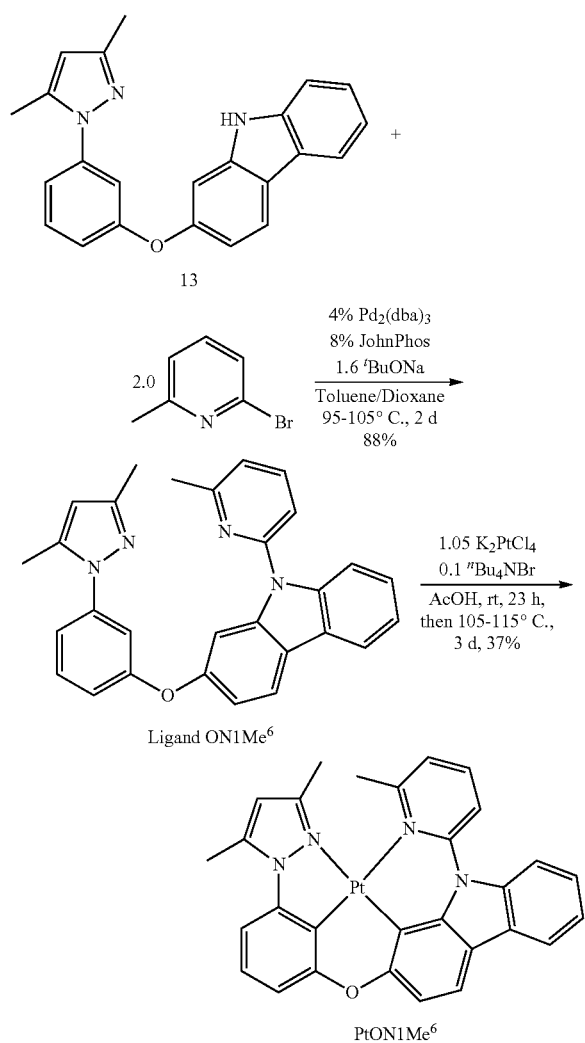

Synthesis of 2-(3-(3,5-dimethyl-1H-pyrazol-1-yl)phenoxy)-9-(6-methylpyridin-2-yl)-9H-carbazole Ligand ON1Me⁶

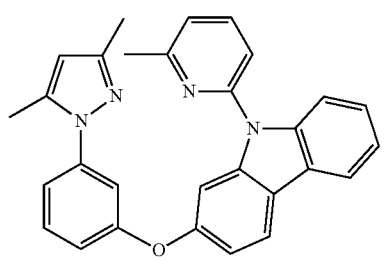 [SMILES: Cc1cccc(-n2c3ccccc3c3ccc(Oc4cccc(-n5nc(C)cc5C)c4)cc32)n1]

Ligand ON1Me⁶ was synthesized according to the procedure of synthesis of Ligand ON1Me⁴ using 2-(3-(3,5-Dimethyl-1H-pyrazol-1-yl)phenoxy)-9H-carbazole 13 (475 mg, 1.34 mmol, 1.0 eq) and 2-bromo-6-methylpyridine (461 mg, 2.68 mmol, 2.0 eq). Purification of the crude product by flash chromatography on silica gel (eluent: hexane/ethyl acetate=10:1-5:1) afforded the title compound as a brown solid (526 mg in 88% yield). ¹H NMR (DMSO-d₆, 400 MHz): δ 2.11 (s, 3H), 2.24 (s, 3H), 2.48 (s, 3H), 6.02 (s, 1H), 7.07 (td, J=8.0, 2.4 Hz, 2H), 7.14 (t, J=2.0 Hz, 1H), 7.24-7.29 (m, 2H), 7.32 (t, J=7.2 Hz, 1H), 7.43 (t, J=7.2 Hz, 1H), 7.48 (t, J=8.0 Hz, 1H), 7.51 (d, J=2.0 Hz, 1H), 7.54 (d, J=8.0 Hz, 1H), 7.76 (d, J=8.0 Hz, 1H), 7.93 (d, J=8.0 Hz, 1H), 8.20 (d, J=7.6 Hz, 1H), 8.25 (d, J=8.0 Hz, 1H). ¹³C NMR (DMSO-d₆, 100 MHz): δ 12.23, 13.23, 23.82, 102.00, 107.51, 111.15, 112.98, 113.68, 115.74, 116.72, 118.42, 119.75, 120.14, 121.13, 121.28, 121.71, 123.23, 125.88, 130.42, 139.23, 139.30, 139.60, 139.93, 140.97, 148.10, 149.75, 155.13, 157.62, 158.34.

Synthesis of 2-(3-(3,5-dimethyl-1H-pyrazol-1-yl)phenoxy)-9-(6-methylpyridin-2-yl)-9H-carbazole platinum complex PtON1Me⁶

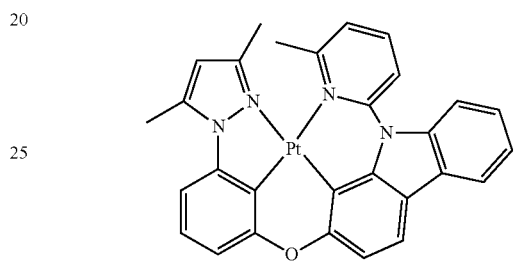

PtON1Me⁶ was synthesized according to the procedure of synthesis of PtON1. 2-(3-(3,5-Dimethyl-1H-pyrazol-1-yl)phenoxy)-9-(6-methylpyridin-2-yl)-9H-carbazole Ligand ON1Me⁶ (510 mg, 1.15 mmol, 1.0 eq) was reacted with K₂PtCl₂ (500 mg, 1.20 mmol, 1.05 eq) in the presence of ⁿBu₄NBr (37 mg, 0.115 mmol, 0.1 eq) at room temperature for 23 hours and then at 105-115° C. for an additional 3 days. Purification of the crude product by flash chromatography on silica gel (eluent: dichloromethane) afforded the title compound as a yellow solid (271 mg in 37% yield). FIG. 3 shows an emission spectrum of PtON1Me⁶ at room temperature. Emission spectra of PtON1Me⁶ at room temperature in CH₂Cl₂ and at 77 K in 2-methyl-THF are shown in FIG. 6. ¹H NMR (CD₂Cl₂, 400 MHz): δ 2.19 (s, 3H), 2.68 (s, 3H), 3.05 (s, 3H), 6.11 (s, 1H), 7.01 (dd, J=7.6, 2.0 Hz, 1H), 7.08 (d, J=7.6 Hz, 1H), 7.16-7.22 (m, 3H), 7.34 (t, J=8.4 Hz, 1H), 7.42 (t, J=8.4 Hz, 1H), 7.64 (t, J=8.4 Hz, 1H), 7.75 (t, J=8.4 Hz, 1H), 7.96-7.99 (m, 2H), 8.09 (d, J=8.4 Hz, 1H). ¹H NMR (DMSO-d₆, 400 MHz): δ 2.14 (s, 3H), 2.69 (s, 3H), 2.98 (s, 3H), 6.35 (s, 1H), 6.96 (dd, J=8.0, 0.8 Hz, 1H), 7.12 (d, J=8.0 Hz, 1H), 7.20 (t, J=8.0 Hz, 1H), 7.25 (dd, J=7.6, 0.8 Hz, 1H), 7.33 (d, J=7.6 Hz, 1H), 7.37 (t, J=7.6 Hz, 1H), 7.45-7.49 (m, 1H), 7.72 (d, J=8.4 Hz, 1H), 8.00 (t, J=8.0 Hz, 1H), 8.08-8.13 (m, 3H). ¹³C NMR (DMSO-d₆, 100 MHz): δ 12.84, 13.99, 27.35, 102.71, 107.70, 109.58, 111.71, 112.80, 112.82, 113.41, 114.61, 115.98, 116.51, 120.09, 121.23, 122.89, 124.55, 124.60, 128.77, 138.72, 140.13, 141.31, 142.58, 147.18, 149.46, 149.53, 151.85, 153.31, 161.27.

Example 12

Platinum complex PtON1-tBu can be prepared according to the following scheme:

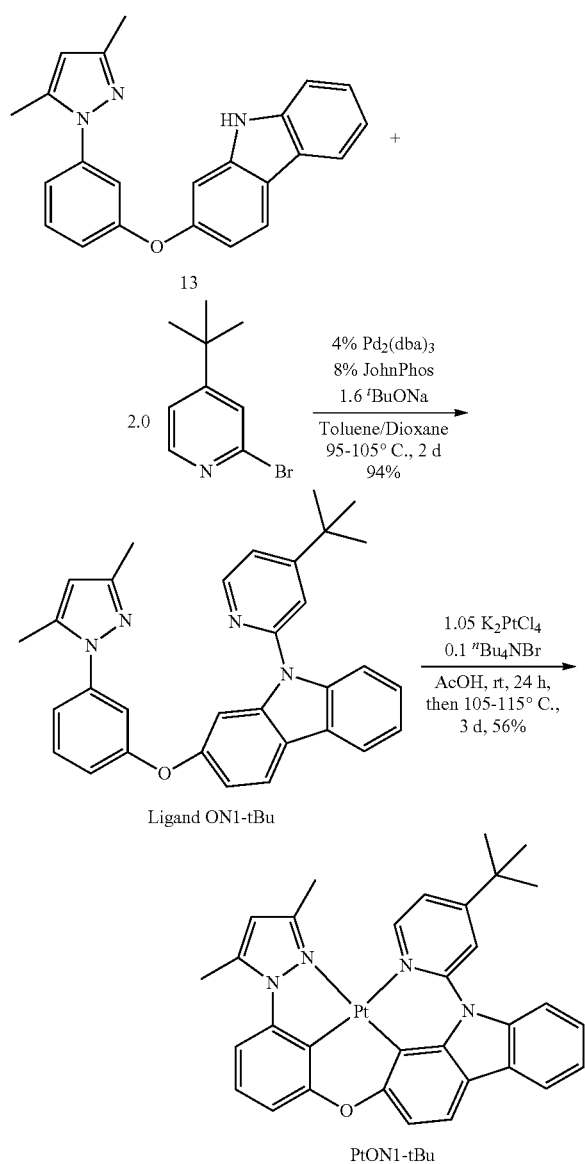

Synthesis of 2-(3-(3,5-dimethyl-1H-pyrazol-1-yl)phenoxy)-9-(4-tert-butylpyridin-2-yl)-9H-carbazole Ligand ON1-tBu Ligand ON1-tBu was synthesized according to the procedure of synthesis of Ligand ON1Me[4] using 2-(3-(3,5-Dimethyl-1H-pyrazol-1-yl)phenoxy)-9H-carbazole 13 (530 mg, 1.5 mmol, 1.0 eq) and 2-bromo-4-tert-butylpyridine (642 mg, 3.0 mmol, 2.0 eq). Purification of the crude product by flash chromatography on silica gel (eluent: hexane/ethyl acetate=10:1-5:1) afforded the title compound as a brown solid (685 mg in 94% yield). $^1$H NMR (DMSO-$d_6$, 400 MHz): δ 1.26 (s, 9H), 2.11 (s, 3H), 2.23 (s, 3H), 6.00 (s, 1H), 7.06-7.08 (m, 1H), 7.10 (dd, J=8.0, 2.4 Hz, 1H), 7.14 (t, J=2.4 Hz, 1H), 7.24-7.26 (m, 1H), 7.31 (t, J=7.2 Hz, 1H), 7.38 (d, J=2.0 Hz, 1H), 7.41-7.48 (m, 3H), 7.61 (d, J=1.6, 1H), 7.74 (d, J=8.4 Hz, 1H), 8.20 (d, J=8.0 Hz, 1H), 8.26 (d, J=8.8 Hz, 1H), 8.55 (d, J=4.8 Hz, 1H). $^{13}$C NMR (DMSO-$d_6$, 100 MHz): δ 12.21, 13.22, 30.01, 34.81, 101.37, 107.50, 111.11, 113.01, 113.81, 115.78, 116.80, 118.49, 119.27, 119.72, 120.13, 121.11, 121.83, 123.20, 125.90, 130.45, 139.19, 139.43, 139.94, 141.01, 148.07, 149.37, 150.60, 155.32, 157.50, 163.03.

Synthesis of 2-(3-(3,5-dimethyl-1H-pyrazol-1-yl)phenoxy)-9-(4-tert-butylpyridin-2-yl)-9H-carbazole platinum complex PtON1-tBu

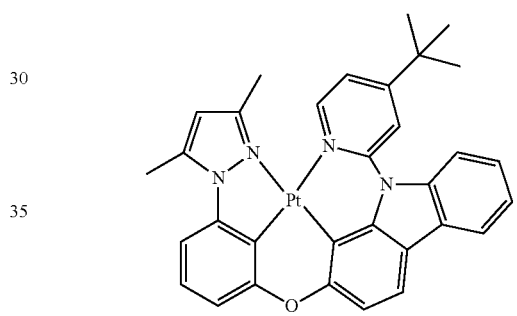

Figure 9:
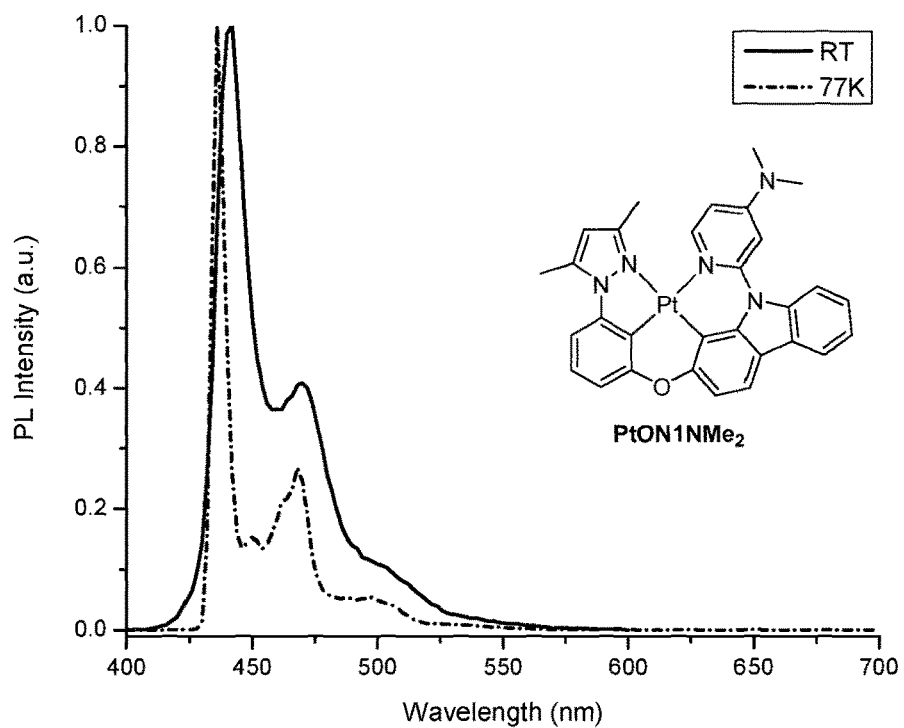
FIG. 9 shows emission spectra of PtON1NMe$_2$ in CH$_2$Cl$_2$ at room temperature and in 2-methyl-THF at 77 K.

PtON1-tBu was synthesized according to the procedure of synthesis of PtON1. 9-(4-Tert-butylpyridin-2-yl)-2-(3-(3,5-dimethyl-1H-pyrazol-1-yl)phenoxy)-9H-carbazole Ligand ON1-tBu (635 mg, 1.30 mmol, 1.0 eq) was reacted with $K_2PtCl_2$ (567 mg, 1.37 mmol, 1.05 eq) in the presence of $^n$Bu$_4$NBr (42 mg, 0.13 mmol, 0.1 eq) at room temperature for 24 hours and then at 105-115° C. for an additional 3 days. Purification of the crude product by flash chromatography on silica gel (eluent: hexane/dichloromethane=1:1) afforded the title compound as a yellow solid (495 mg in 56% yield). FIG. 3 shows an emission spectrum of PtON1-tBu at room temperature. Emission spectra of PtON1-tBu at room temperature in $CH_2Cl_2$ and at 77 K in 2-methyl-THF are shown in FIG. 9. $^1$H NMR ($CD_2Cl_2$, 400 MHz): δ 1.32 (s, 9H), 2.46 (s, 3H), 2.73 (s, 3H), 6.18 (s, 1H), 6.99-7.03 (m, 2H), 7.20-7.26 (m, 3H), 7.38 (t, J=7.6 Hz, 1H), 7.48 (t, J=8.0 Hz, 1H), 7.79 (d, J=7.6 Hz, 1H), 7.94 (d, J=8.0 Hz, 1H), 8.07 (d, J=8.0 Hz, 1H), 8.09 (d, J=1.2 Hz, 1H), 9.08 (d, J=7.2 Hz, 1H). $^1$H NMR (DMSO-$d_6$, 400 MHz): δ 1.32 (s, 9H), 2.43 (s, 3H), 2.75 (s, 3H), 6.44 (s, 1H), 6.95 (d, J=8.0 Hz, 1H), 7.17 (d, J=8.4 Hz, 1H), 7.22 (t, J=8.0 Hz, 1H), 7.28 (d, J=7.6 Hz, 1H), 7.34 (dd, J=6.0, 1.6 Hz, 1H), 7.40 (t, J=7.6 Hz, 1H), 7.50 (t, J=7.6 Hz, 1H), 7.86 (d, J=8.4 Hz, 1H), 8.05 (d, J=1.2 Hz, 1H), 8.11 (d, J=8.0 Hz, 1H), 8.16 (d, J=7.6 Hz, 1H), 9.11 (d, J=6.4 Hz, 1H). $^{13}$C NMR ($CD_2Cl_2$, 100 MHz): δ 14.99, 15.15, 30.24, 35.89, 100.32, 107.22, 110.29, 111.78, 112.79, 113.07, 113.21, 114.78, 115.40, 116.33, 116.36, 120.32, 122.94, 124.45, 124.71, 129.28, 139.07, 142.06, 143.23, 148.44, 149.35, 150.01, 152.80, 153.22, 153.41, 163.97.

Example 13

Platinum complex PtON1NMe$_2$ can be prepared according to the following scheme:

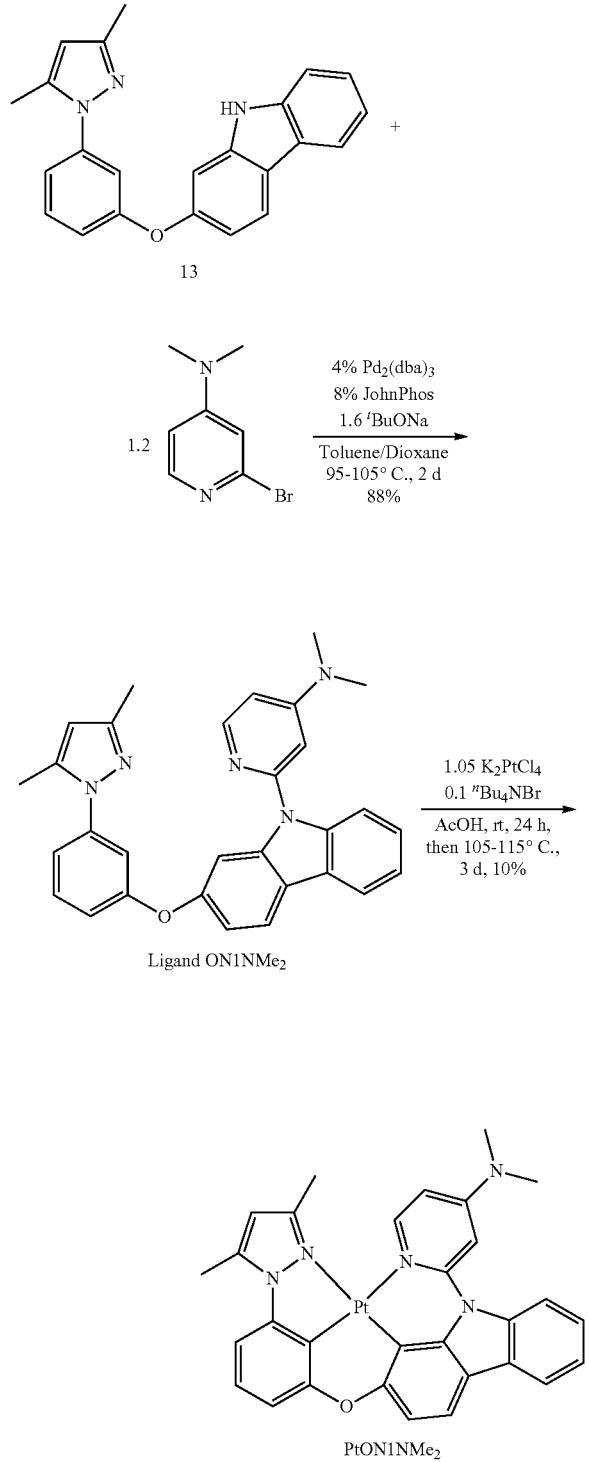

Ligand ON1NMe$_2$

PtON1NMe$_2$

Synthesis of 2-(2-(3-(3,5-Dimethyl-1H-pyrazol-1-yl)phenoxy)-9H-carbazol-9-yl)-N,N-dimethylpyridin-4-amine Ligand ON1NMe$_2$ Ligand ON1NMe$_2$ was synthesized according to the procedure of synthesis of Ligand ON1Me[4] using 2-(3-(3,5-dimethyl-1H-pyrazol-1-yl)phenoxy)-9H-carbazole 13 (530 mg, 1.5 mmol, 1.0 eq) and 2-bromo-4-N,N-dimethylaminopyridine (362 mg, 1.8 mmol, 1.2 eq). Purification of the crude product by flash chromatography on silica gel (eluent: hexane/ethyl acetate=3:1-2:1-1:1) afforded the title compound as a colorless solid (624 mg in 88% yield). $^1$H NMR (DMSO-d$_6$, 400 MHz): δ 2.10 (s, 3H), 2.23 (s, 3H), 2.94 (s, 6H), 5.99 (s, 1H), 6.63 (dd, J=6.0, 1.6 Hz, 1H), 6.74 (d, J=1.6 Hz, 1H), 7.02-7.07 (m, 2H), 7.12 (s, 1H), 7.22 (d, J=8.0 Hz, 1H), 7.27 (t, J=7.6 Hz, 1H), 7.37-7.46 (m, 3H), 7.74 (d, J=8.4 Hz, 1H), 8.15-8.17 (m, 2H), 8.22 (d, J=2.0 Hz, 1H). $^{13}$C NMR (DMSO-d$_6$, 100 MHz): δ 12.23, 13.22, 38.89, 101.14, 102.07, 105.77, 107.49, 111.33, 112.71, 113.49, 116.46, 118.27, 119.63, 119.99, 120.64, 121.63, 122.92, 125.70, 130.38, 139.21, 139.73, 140.24, 140.97, 148.07, 148.90, 151.08, 154.84, 156.09, 157.86.

Synthesis of 2-(2-(3-(3,5-Dimethyl-1H-pyrazol-1-yl)phenoxy)-9H-carbazol-9-yl)-N,N-dimethylpyridin-4-amine platinum complex PtON1NMe$_2$ PtON1NMe$_2$ was synthesized according to the procedure of synthesis of PtON1. 2-(2-(3-(3,5-Dimethyl-1H-pyrazol-1-yl)phenoxy)-9H-carbazol-9-yl)-N,N-dimethylpyridin-4-amine Ligand ON1NMe$_2$ (560 mg, 1.18 mmol, 1.0 eq) was reacted with K$_2$PtCl$_2$ (514 mg, 1.24 mmol, 1.05 eq) in the presence of $^n$Bu$_4$NBr (38 mg, 0.118 mmol, 0.1 eq) at room temperature for 24 hours and then at 105-115° C. for an additional 3 days. Purification of the crude product by flash chromatography on silica gel (eluent: hexane/dichloromethane=1:2) afforded the title compound as a yellow solid (81 mg in 10% yield). FIG. 3 shows an emission spectrum of PtON1NMe$_2$ at room temperature. Emission spectra of PtON1NMe$_2$ at room temperature in CH$_2$Cl$_2$ and at 77 K in 2-methyl-THF are shown in FIG. 9. $^1$H NMR (DMSO-d$_6$, 400 MHz): δ 2.45 (s, 3H), 2.74 (s, 3H), 3.08 (s, 6H), 6.42 (s, 1H), 6.66 (dd, J=7.2, 2.0 1H), 6.92 (d, J=8.0 Hz, 1H), 7.10 (d, J=2.0 Hz, 1H), 7.12 (dd, J=8.4, 1.2 Hz, 1H), 7.19 (t, J=8.0 Hz, 1H), 7.25 (d, J=8.0 Hz, 1H), 7.35 (t, J=8.0 Hz, 1H), 7.45 (t, J=8.4 Hz, 1H), 7.81 (dd, J=8.4, 0.8 Hz, 1H), 8.12 (d, J=8.0 Hz, 1H), 8.20 (d, J=7.6 Hz, 1H), 8.67 (d, J=6.4 Hz, 1H). $^1$H NMR (CD$_2$Cl$_2$, 400 MHz): δ 2.47 (s, 3H), 2.71 (s, 3H), 3.02 (s, 6H), 6.14 (s, 1H), 6.32 (dd, J=7.2, 2.4 1H), 6.97-6.99 (m, 1H), 7.13-7.21 (m, 4H), 7.32 (t, J=7.6 Hz, 1H), 7.40 (t, J=8.0 Hz, 1H), 7.75 (dd, J=8.0, 2.0 Hz, 1H), 8.02 (d, J=8.0 Hz, 2H), 8.69 (dd, J=7.2, 2.0 Hz, 1H). $^{13}$C NMR (CD$_2$Cl$_2$, 100 MHz): δ 14.81, 15.14, 39.69, 96.01, 100.83, 103.58, 107.16, 110.14, 112.51, 112.94, 113.09, 115.00, 115.04, 116.24, 120.12, 122.39, 124.13, 124.25, 129.18, 139.41, 141.85, 143.99, 148.41, 149.53, 149.82, 152.65, 153.16, 153.32, 155.98.

Example 14

Platinum complex PtON1Ph can be prepared according to the following scheme:

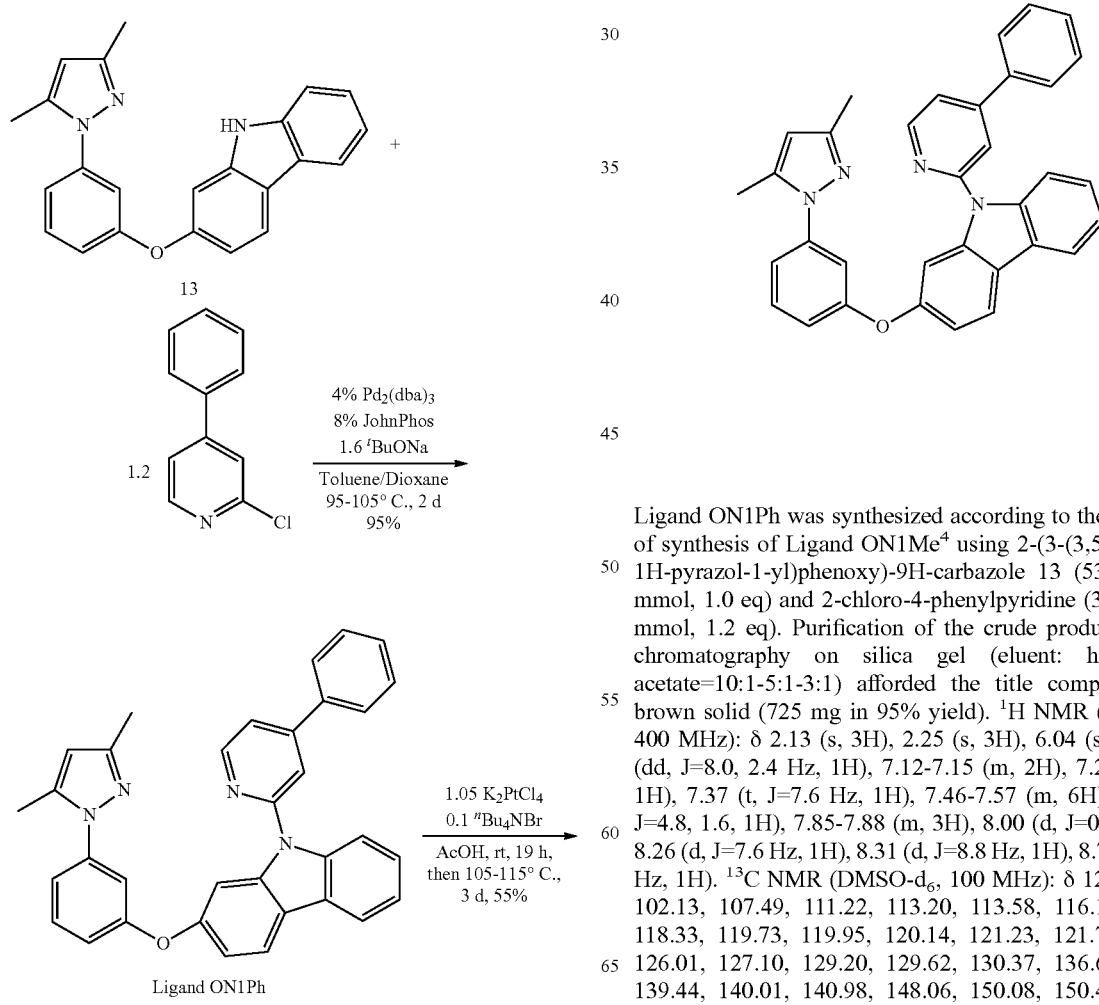

Ligand ON1Ph

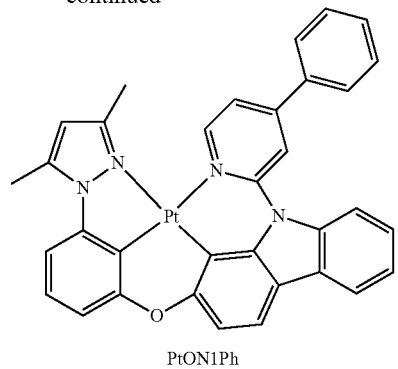

PtON1Ph

Synthesis of 2-(3-(3,5-dimethyl-1H-pyrazol-1-yl) phenoxy)-9-(4-phenylpyridin-2-yl)-9H-carbazole Ligand ON1Ph Ligand ON1Ph was synthesized according to the procedure of synthesis of Ligand ON1Me[4] using 2-(3-(3,5-Dimethyl-1H-pyrazol-1-yl)phenoxy)-9H-carbazole 13 (530 mg, 1.5 mmol, 1.0 eq) and 2-chloro-4-phenylpyridine (342 mg, 1.8 mmol, 1.2 eq). Purification of the crude product by flash chromatography on silica gel (eluent: hexane/ethyl acetate=10:1-5:1-3:1) afforded the title compound as a brown solid (725 mg in 95% yield). $^1$H NMR (DMSO-d$_6$, 400 MHz): δ 2.13 (s, 3H), 2.25 (s, 3H), 6.04 (s, 1H), 7.10 (dd, J=8.0, 2.4 Hz, 1H), 7.12-7.15 (m, 2H), 7.25-7.27 (m, 1H), 7.37 (t, J=7.6 Hz, 1H), 7.46-7.57 (m, 6H), 7.79 (dd, J=4.8, 1.6, 1H), 7.85-7.88 (m, 3H), 8.00 (d, J=0.4 Hz, 1H), 8.26 (d, J=7.6 Hz, 1H), 8.31 (d, J=8.8 Hz, 1H), 8.74 (d, J=5.2 Hz, 1H). $^{13}$C NMR (DMSO-d$_6$, 100 MHz): δ 12.19, 13.21, 102.13, 107.49, 111.22, 113.20, 113.58, 116.14, 116.49, 118.33, 119.73, 119.95, 120.14, 121.23, 121.77, 123.29, 126.01, 127.10, 129.20, 129.62, 130.37, 136.62, 139.19, 139.44, 140.01, 140.98, 148.06, 150.08, 150.46, 151.29, 155.08, 157.76.

Synthesis of 2-(3-(3,5-dimethyl-1H-pyrazol-1-yl)phenoxy)-9-(4-phenylpyridin-2-yl)-9H-carbazole platinum complex PtON1Ph

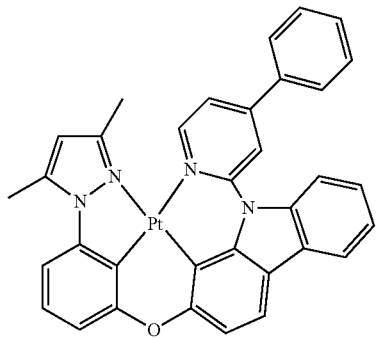

Figure 10:
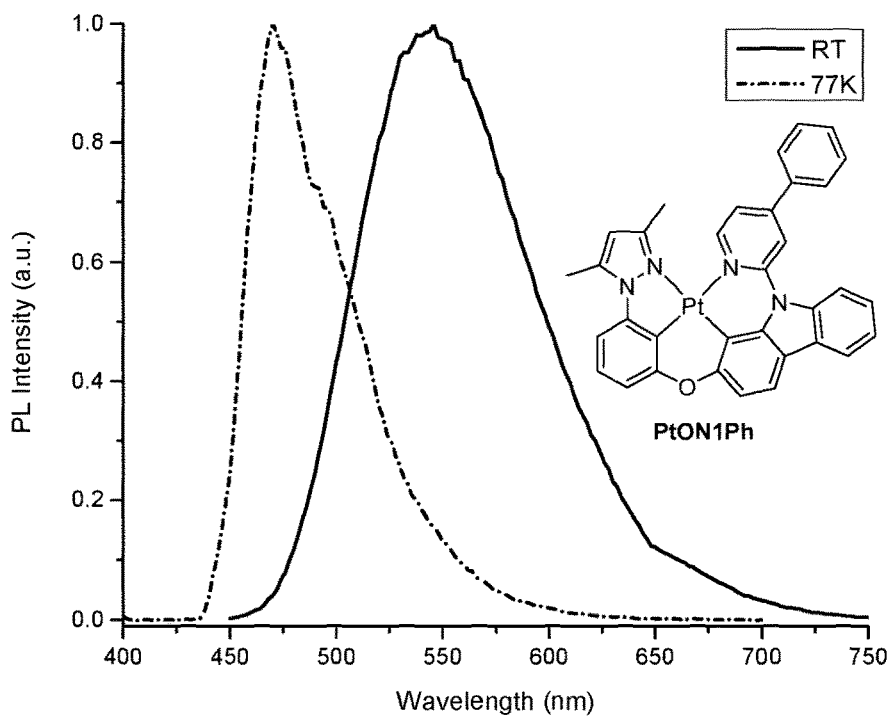
FIG. 10 shows emission spectra of PtON1Ph in CH$_2$Cl$_2$ at room temperature and in 2-methyl-THF at 77.

PtON1Ph was synthesized according to the procedure of synthesis of PtON1. 2-(3-(3,5-Dimethyl-1H-pyrazol-1-yl)phenoxy)-9-(4-phenylpyridin-2-yl)-9H-carbazole Ligand ON1Ph (679 mg, 1.34 mmol, 1.0 eq) was reacted with $K_2PtCl_2$ (584 mg, 1.41 mmol, 1.05 eq) in the presence of $^nBu_4NBr$ (43 mg, 0.134 mmol, 0.1 eq) at room temperature for 19 hours and then at 105-115° C. for an additional 3 days. Purification of the crude product by flash chromatography on silica gel (eluent: hexane/dichloromethane=1:1) afforded the title compound as a yellow solid (517 mg in 55% yield). FIG. 3 shows an emission spectrum of PtON1Ph at room temperature. Emission spectra of PtON1Ph at room temperature in $CH_2Cl_2$ and at 77 K in 2-methyl-THF are shown in FIG. 10. $^1H$ NMR (DMSO-$d_6$, 400 MHz): δ 2.35 (s, 3H), 2.70 (s, 3H), 6.35 (s, 1H), 6.96 (d, J=8.0, 1H), 7.18-7.26 (m, 3H), 7.35-7.37 (m, 2H), 7.45-7.48 (m, 4H), 7.71-7.72 (m, 2H), 7.84 (d, J=8.4 Hz, 1H), 8.12 (d, J=7.2 Hz, 1H), 8.18 (s, 1H), 8.22 (d, J=8.4 Hz, 1H), 9.14 (d, J=6.4 Hz, 1H). $^{13}C$ NMR (DMSO-$d_6$, 100 MHz): δ 14.32, 14.35, 100.17, 107.15, 110.29, 111.18, 112.23, 112.38, 112.42, 115.04, 115.31, 115.69, 116.63, 120.02, 122.90, 124.72, 126.96, 128.01, 129.37, 130.11, 136.08, 137.99, 141.88, 142.09, 147.41, 148.26, 149.61, 150.15, 151.64, 152.01, 153.99.

Example 15

Platinum complex PtON1F can be prepared according to the following scheme:

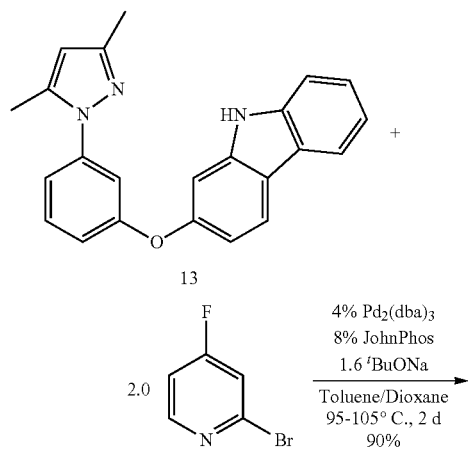

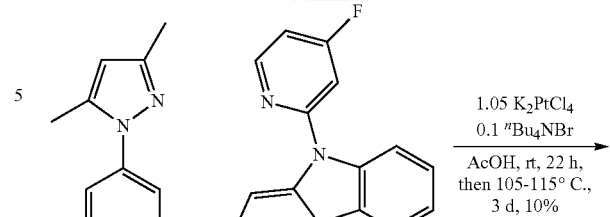

Ligand ON1F

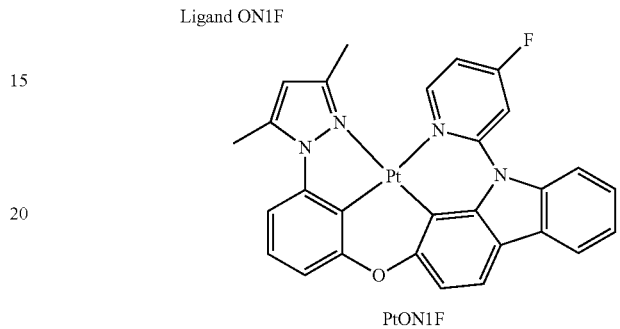

PtON1F

Synthesis of 2-(3-(3,5-dimethyl-1H-pyrazol-1-yl)phenoxy)-9-(4-fluoropyridin-2-yl)-9H-carbazole Ligand ON1F

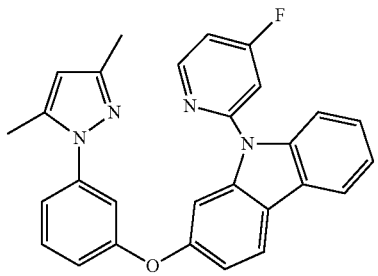 [SMILES: Cc1cc(C)n(-c2cccc(Oc3ccc4c5ccccc5n(-c5cc(F)ccn5)c4c3)c2)n1]

Ligand ON1F was synthesized according to the procedure of synthesis of Ligand ON1Me$^4$ using 2-(3-(3,5-dimethyl-1H-pyrazol-1-yl)phenoxy)-9H-carbazole 13 (565 mg, 1.6 mmol, 1.0 eq) and 2-bromo-4-fluoropyridine (563 mg, 3.2 mmol, 2.0 eq). Purification of the crude product by flash chromatography on silica gel (eluent: hexane/ethyl acetate=10:1-5:1-4:1) afforded the title compound as a brown solid (643 mg in 90% yield). $^1H$ NMR (DMSO-$d_6$, 400 MHz): δ 2.10 (s, 3H), 2.24 (s, 3H), 6.00 (s, 1H), 7.03 (dd, J=8.4, 2.4 Hz, 1H), 7.08-7.10 (m, 2H), 7.22 (d, J=8.0 Hz, 1H), 7.32-7.39 (m, 2H), 7.43 (d, J=7.6 Hz, 1H), 7.46 (d, J=8.4 Hz, 1H), 7.61 (d, J=2.0 Hz, 1H), 7.71 (dd, J=10.0, 1.6 Hz, 1H), 7.82 (d, J=8.4 Hz, 1H), 8.20 (d, J=7.6 Hz, 1H), 8.25 (d, J=8.4 Hz, 1H), 8.68 (dd, J=8.8, 5.6 Hz, 1H). $^{13}C$ NMR (DMSO-$d_6$, 100 MHz): δ 12.20, 13.21, 102.95, 106.76 (d, J=20.3 Hz), 107.47, 110.11 (d, J=16.0 Hz), 111.37, 113.24, 113.67, 116.24, 118.24, 120.18, 120.20, 121.60, 121.74, 123.43, 126.11, 130.37, 139.12, 139.22, 139.77, 140.94, 148.07, 151.98 (d, J=8.8 Hz), 152.69 (d, J=10.6 Hz), 154.83, 157.95, 169.56 (d, J=258.8 Hz). $^{19}F$ NMR (DMSO-$d_6$, 376 MHz): δ −99.56--99.49 (m, 1F).

Synthesis of 2-(3-(3,5-dimethyl-1H-pyrazol-1-yl)phenoxy)-9-(4-fluoropyridin-2-yl)-9H-carbazole platinum complex PtON1F

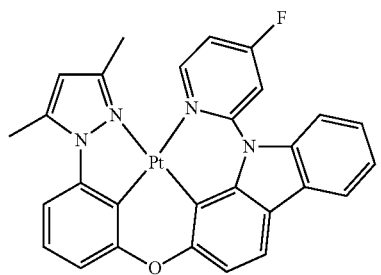

Figure 11:
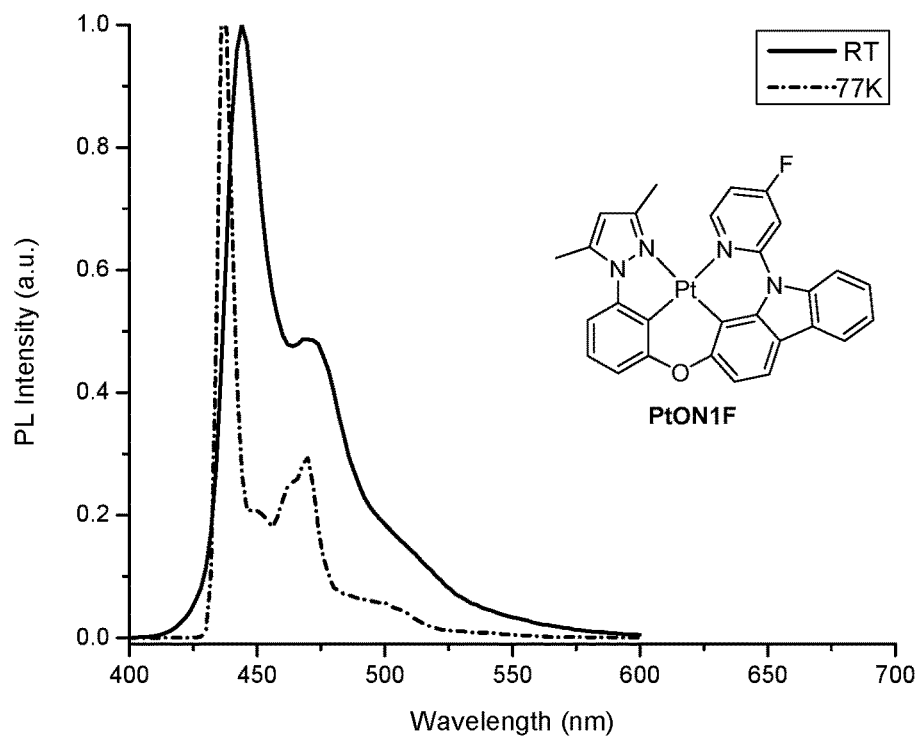
FIG. 11 shows emission spectra of PtON1F in CH$_2$Cl$_2$ at room temperature and in 2-methyl-THF at 77 K.

PtON1F was synthesized according to the procedure of synthesis of PtON1. 2-(3-(3,5-Dimethyl-1H-pyrazol-1-yl)phenoxy)-9-(4-fluoropyridin-2-yl)-9H-carbazole Ligand ON1F (600 mg, 1.34 mmol, 1.0 eq) was reacted with $K_2PtCl_2$ (583 mg, 1.40 mmol, 1.05 eq) in the presence of $^nBu_4NBr$ (43 mg, 0.13 mmol, 0.1 eq) at room temperature for 22 hours and then at 105-115° C. for an additional 3 days. Purification of the crude product by flash chromatography on silica gel (eluent: dichloromethane) afforded the title compound as a yellow solid (81 mg in 10% yield). FIG. 3 shows an emission spectrum of PtON1F at room temperature. Emission spectra of PtON1F at room temperature in $CH_2Cl_2$ and at 77 K in 2-methyl-THF are shown in FIG. 11. $^1H$ NMR (DMSO-$d_6$, 400 MHz): δ 2.43 (s, 3H), 2.76 (s, 3H), 6.46 (s, 1H), 6.96 (d, J=8.0 Hz, 1H), 7.20 (d, J=8.8 Hz, 1H), 7.24 (d, J=8.4 Hz, 1H), 7.28-7.31 (m, 2H), 7.43 (t, J=7.6 Hz, 1H), 7.51 (t, J=8.0 Hz, 1H), 7.87 (d, J=8.4 Hz, 1H), 7.98 (dd, J=10.4, 2.4 Hz, 1H), 8.15 (d, J=8.4 Hz, 2H), 9.30 (t, J=6.8 Hz, 1H). $^{13}C$ NMR (DMSO-$d_6$, 100 MHz): δ 14.32, 100.33, 102.80 (d, J=23.9 Hz), 107.18, 108.09 (d, J=19.8 Hz), 110.34, 110.52, 112.42, 112.45, 115.17, 115.33, 115.77, 119.98, 123.33, 124.76, 128.16, 137.77, 141.80, 142.01, 147.31, 149.70, 150.08 (d, J=11.8 Hz), 151.67, 151.91, 156.71 (d, J=10.1 Hz), 168.86 (d, J=262.5 Hz). $^{19}F$ NMR (DMSO-$d_6$, 376 MHz): δ −96.41--−96.34 (m, 1F).

Example 16

Platinum complex PtON1CF$_3$ can be prepared according to the following scheme:

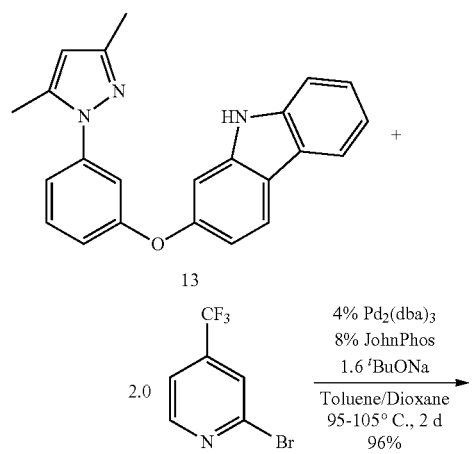

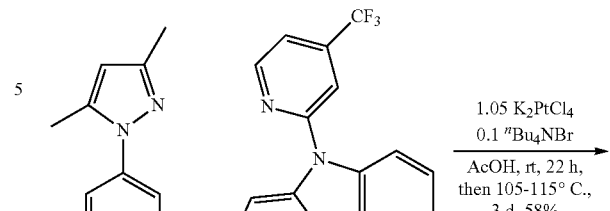

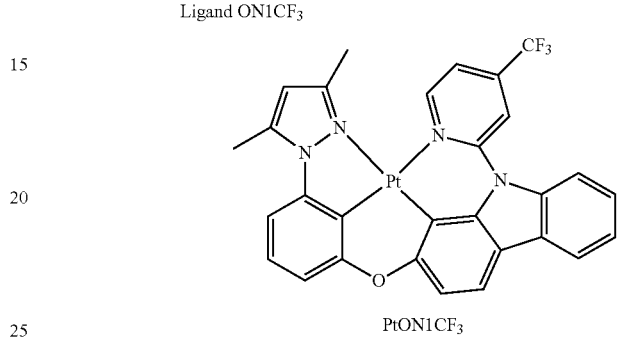

Synthesis of 2-(3-(3,5-dimethyl-1H-pyrazol-1-yl)phenoxy)-9-(4-(trifluoromethyl)pyridin-2-yl)-9H-carbazole Ligand ON1CF$_3$

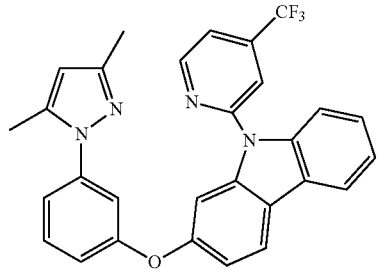 [SMILES: Cc1cc(C)n(-c2cccc(Oc3ccc4c5ccccc5n(-c5cc(C(F)(F)F)ccn5)c4c3)c2)n1]

Ligand ON1CF$_3$ was synthesized according to the procedure of synthesis of Ligand ON1Me$^4$ using 2-(3-(3,5-dimethyl-1H-pyrazol-1-yl)phenoxy)-9H-carbazole 13 (707 mg, 2.0 mmol, 1.0 eq) and 2-bromo-4-(trifluoromethyl)pyridine (904 mg, 4.0 mmol, 2.0 eq). Purification of the crude product by flash chromatography on silica gel (eluent: hexane/ethyl acetate=10:1-5:1) afforded the title compound as a brown solid (962 mg in 96% yield). $^1H$ NMR (DMSO-$d_6$, 400 MHz): δ 2.13 (s, 3H), 2.26 (s, 3H), 6.04 (s, 1H), 7.08 (dd, J=8.0, 2.4 Hz, 1H), 7.12-7.15 (m, 2H), 7.25-7.27 (m, 1H), 7.38 (t, J=7.6 Hz, 1H), 7.48 (t, J=8.0 Hz, 2H), 7.58 (d, J=1.6 Hz, 1H), 7.81-7.83 (m, 2H), 8.10 (s, 1H), 8.25 (d, J=7.6 Hz, 1H), 8.30 (d, J=8.8 Hz, 1H), 8.95 (d, J=4.8 Hz, 1H). $^{13}C$ NMR (DMSO-$d_6$, 100 MHz): δ 12.16, 13.18, 102.47, 107.46, 111.09, 113.43, 113.71, 114.52 (q, J=3.9 Hz), 116.37, 117.37 (q, J=2.7 Hz), 118.32, 120.25, 121.77, 121.81, 122.55 (q, J=272.5 Hz), 123.59, 126.16, 130.35, 139.09, 139.19, 139.56 (q, J=34.7 Hz), 139.73, 140.98, 148.06, 151.32, 151.53, 155.05, 157.75. $^{19}F$ NMR (DMSO-$d_6$, 376 MHz): δ −63.32.

Synthesis of 2-(3-(3,5-dimethyl-1H-pyrazol-1-yl)phenoxy)-9-(4-(trifluoromethyl)pyridin-2-yl)-9H-carbazole platinum complex PtON1CF₃

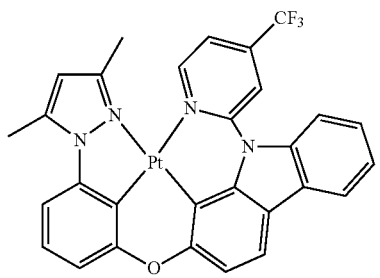

Figure 12:
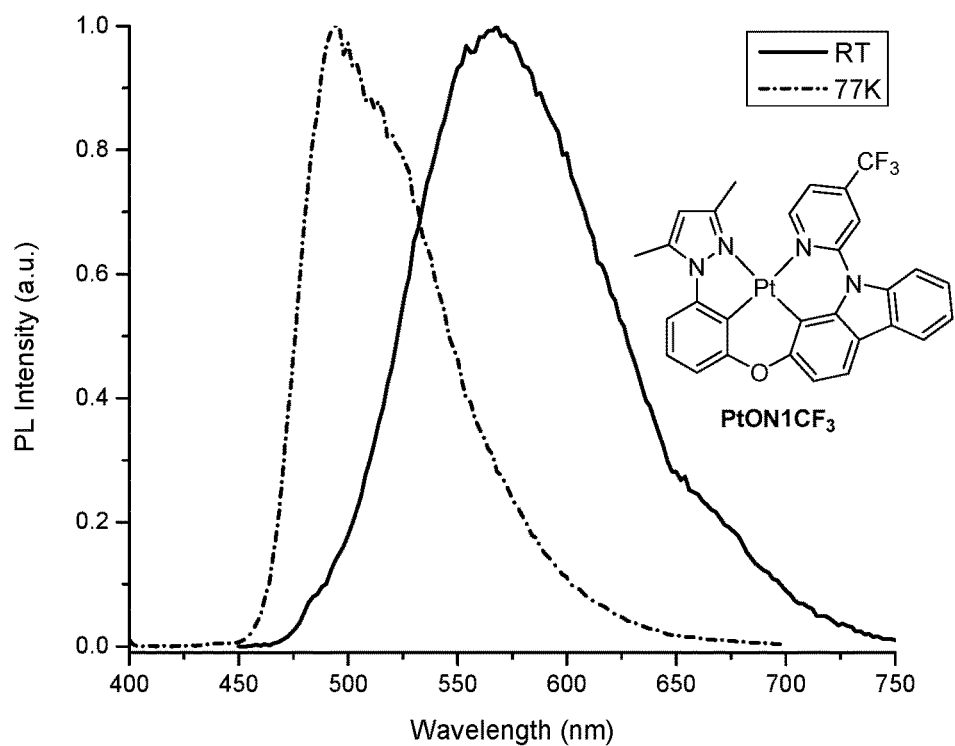
FIG. 12 shows emission spectra of PtON1CF$_3$ in CH$_2$Cl$_2$ at room temperature and in 2-methyl-THF at 77 K.

PtON1CF₃ was synthesized according to the procedure of synthesis of PtON1. 2-(3-(3,5-Dimethyl-1H-pyrazol-1-yl)phenoxy)-9-(4-(trifluoromethyl)pyridin-2-yl)-9H-carbazole Ligand ON1CF₃ (900 mg, 1.81 mmol, 1.0 eq) was reacted with K₂PtCl₂ (787 mg, 1.90 mmol, 1.05 eq) in the presence of ⁿBu₄NBr (58 mg, 0.18 mmol, 0.1 eq) at room temperature for 22 hours and then at 105-115° C. for an additional 3 days. Purification of the crude product by flash chromatography on silica gel (eluent: hexane/dichloromethane=1:1) afforded the title compound as a yellow solid (720 mg in 58% yield). FIG. 3 shows an emission spectrum of PtON1CF₃ at room temperature. Emission spectra of PtON1CF₃ at room temperature in CH₂Cl₂ and at 77 K in 2-methyl-THF are shown in FIG. 12. ¹H NMR (CD₂Cl₂, 400 MHz): δ 2.41 (s, 3H), 2.72 (s, 3H), 6.17 (s, 1H), 7.03-7.06 (m, 1H), 7.11 (d, J=5.6 Hz, 1H), 7.18-7.25 (m, 2H), 7.31 (dd, J=8.0, 1.6 Hz, 1H), 7.41-7.50 (m, 2H), 7.80 (dd, J=8.4, 1.6 Hz, 1H), 7.93 (d, J=8.4 Hz, 1H), 8.07 (d, J=7.6 Hz, 1H), 8.36 (s, 1H), 9.39 (d, J=6.4 Hz, 1H). ¹³C NMR (CD₂Cl₂, 100 MHz): δ 14.97, 15.14, 100.19, 107.38, 110.48, 110.49, 122.74 (q, J=3.7 Hz), 113.36, 113.43, 113.49 (q, J=2.6 Hz), 114.76, 115.79, 116.57, 120.57, 122.90 (q, J=272.4 Hz), 124.03, 124.92, 125.19, 129.77, 138.56, 140.11 (q, J=35.5 Hz), 142.31, 142.56, 148.34, 149.87, 150.00, 152.96, 153.01, 155.49. ¹⁹F NMR (DMSO-d₆, 376 MHz): δ −64.10.

Example 17

Platinum complex PtON1N can be prepared according to the following scheme:

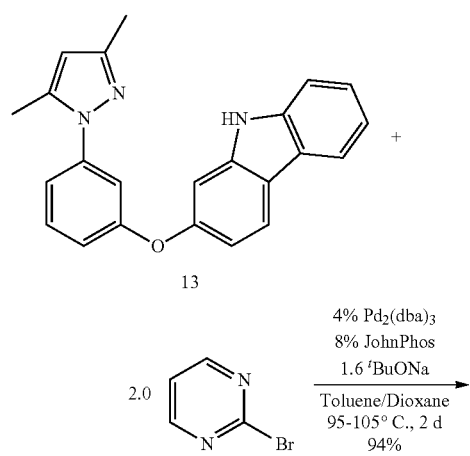

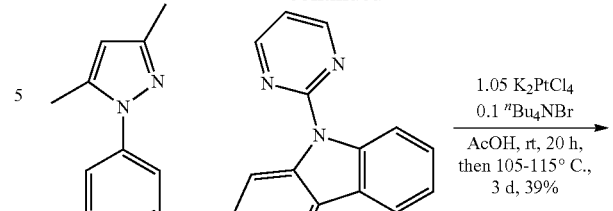

Ligand ON1N

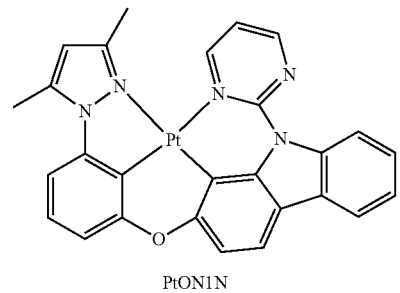

PtON1N

Synthesis of 2-(3-(3,5-dimethyl-1H-pyrazol-1-yl)phenoxy)-9-(pyrimidin-2-yl)-9H-carbazole Ligand ON1N

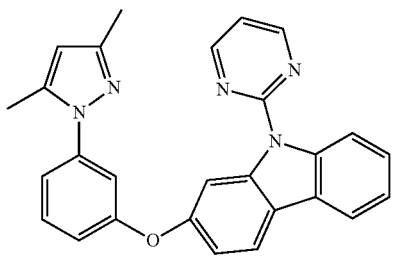 [SMILES: Cc1cc(C)n(-c2cccc(Oc3ccc4c5ccccc5n(-c5ncccn5)c4c3)c2)n1]

Ligand ON1N was synthesized according to the procedure of synthesis of Ligand ON1Me⁴ using 2-(3-(3,5-dimethyl-1H-pyrazol-1-yl)phenoxy)-9H-carbazole 13 (707 mg, 2.0 mmol, 1.0 eq) and 2-bromopyrimidine (636 mg, 4.0 mmol, 2.0 eq). Purification of the crude product by flash chromatography on silica gel (eluent: hexane/ethyl acetate=10:1-5:1-3:1) afforded the title compound as a brown solid (814 mg in 94% yield). ¹H NMR (DMSO-d₆, 400 MHz): δ 2.11 (s, 3H), 2.27 (s, 3H), 6.01 (s, 1H), 7.06 (dd, J=8.0, 2.4 Hz, 1H), 7.12 (t, J=2.0 Hz, 1H), 7.15 (dd, J=8.4, 2.0 Hz, 1H), 7.23-7.26 (m, 1H), 7.37-7.40 (m, 2H), 7.46-7.52 (m, 2H), 8.19 (d, J=8.0 Hz, 1H), 7.25 (d, J=7.6 Hz, 1H), 8.59 (d, J=2.4 Hz, 1H), 8.79 (d, J=8.4 Hz, 1H), 8.93 (d, J=4.4 Hz, 2H). ¹³C NMR (DMSO-d₆, 100 MHz): δ 12.25, 13.22, 107.47, 107.67, 113.10, 114.61, 116.12, 116.16, 117.19, 118.20, 119.69, 121.16, 121.57, 122.60, 124.62, 126.31, 130.43, 138.86, 139.25, 139.33, 140.97, 148.07, 154.68, 158.05, 158.12, 158.63.

Synthesis of 2-(3-(3,5-dimethyl-1H-pyrazol-1-yl)phenoxy)-9-(pyrimidin-2-yl)-9H-carbazole platinum complex PtON1N

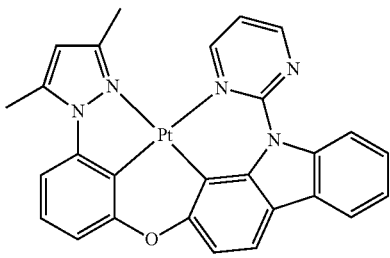

Figure 13:
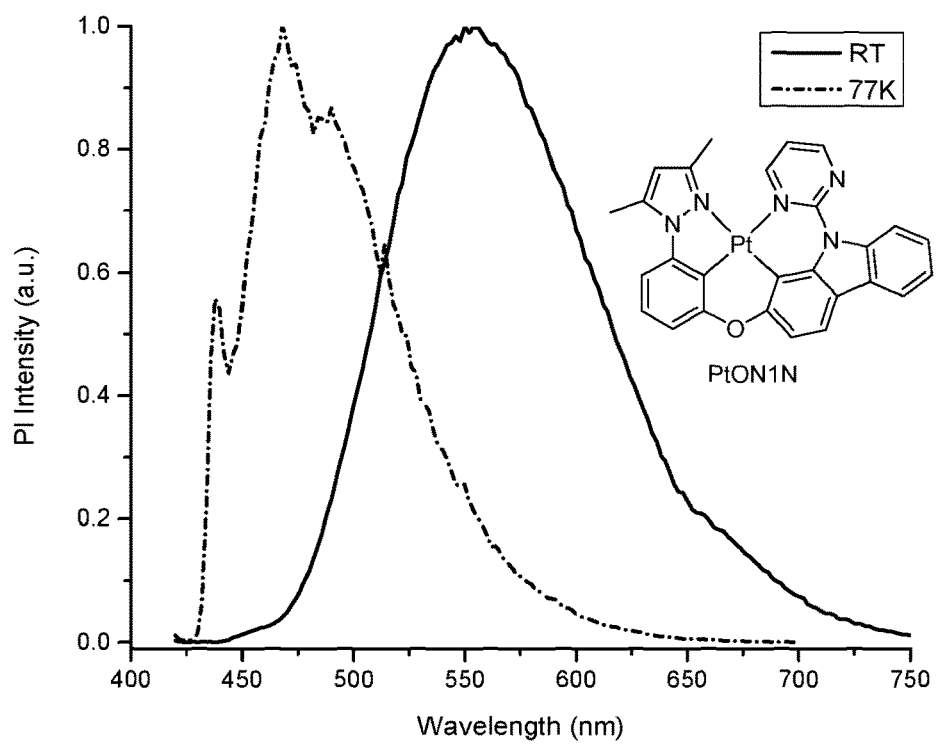
FIG. 13 shows emission spectra of PtON1N in CH$_2$Cl$_2$ at room temperature and in 2-methyl-THF at 77 K.

PtON1N was synthesized according to the procedure of synthesis of PtON1. 2-(3-(3,5-dimethyl-1H-pyrazol-1-yl)phenoxy)-9-(pyrimidin-2-yl)-9H-carbazole Ligand ON1N (770 mg, 1.78 mmol, 1.0 eq) was reacted with $K_2PtCl_2$ (776 mg, 1.87 mmol, 1.05 eq) in the presence of $^nBu_4NBr$ (57 mg, 0.18 mmol, 0.1 eq) at room temperature for 20 hours and then at 105-115° C. for an additional 3 days. Purification of the crude product by flash chromatography on silica gel (eluent: dichloromethane) afforded the title compound as a yellow solid (433 mg in 39% yield). Emission spectra of PtON1N at room temperature in $CH_2Cl_2$ and at 77 K in 2-methyl-THF are shown in FIG. 13. $^1$H NMR ($CD_2Cl_2$, 400 MHz): δ 2.32 (s, 3H), 2.76 (s, 3H), 6.44 (s, 1H), 6.98 (d, J=7.6 Hz, 1H), 7.22-7.26 (m, 2H), 7.30 (d, J=8.0 Hz, 1H), 7.37 (t, J=6.0 Hz, 1H), 7.41 (t, J=7.6 Hz, 1H), 7.49 (d, J=8.0 Hz, 1H), 7.90 (d, J=8.4 Hz, 1H), 8.12 (d, J=7.6 Hz, 1H), 8.80 (d, J=8.0 Hz, 1H), 9.14-9.16 (m, 1H), 9.51-9.52 (m, 1H). $^{13}$C NMR (DMSO-$d_6$, 100 MHz): δ 14.33, 99.67, 107.05, 110.51, 110.89, 112.28, 112.72, 114.92, 115.45, 116.20, 118.99, 119.40, 123.26, 124.63, 124.90, 127.59, 137.90, 140.97, 142.04, 147.40, 149.84, 151.35, 151.51, 151.67, 159.30, 162.97.

Example 18

Platinum complex PtON1Cz can be prepared according to the following scheme:

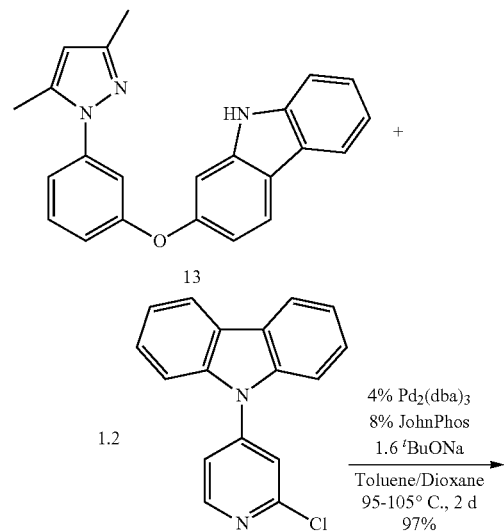

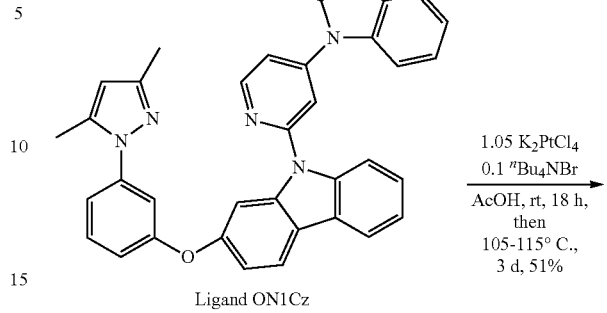

Ligand ON1Cz

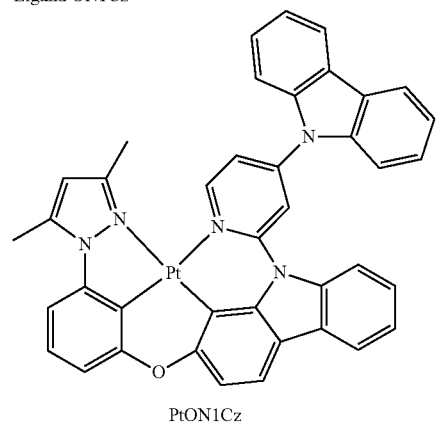

PtON1Cz

Synthesis of 9-(4-(9H-carbazol-9-yl)pyridin-2-yl)-2-(3-(3,5-dimethyl-1H-pyrazol-1-yl)phenoxy)-9H-carbazole Ligand ON1N

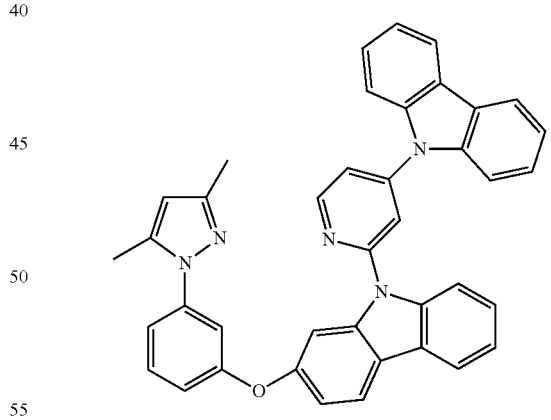

Ligand ON1Cz was synthesized according to the procedure of synthesis of Ligand ON1Me[4] using 2-(3-(3,5-Dimethyl-1H-pyrazol-1-yl)phenoxy)-9H-carbazole 13 (589 mg, 1.66 mmol, 1.0 eq) and 9-(2-chloropyridin-4-yl)-9H-carbazole (560 mg, 2.0 mmol, 1.2 eq). Purification of the crude product by flash chromatography on silica gel (eluent: hexane/ethyl acetate=10:1-3:1) afforded the title compound as a brown solid (958 mg in 97% yield). $^1$H NMR (DMSO-$d_6$, 400 MHz): δ 2.07 (s, 3H), 2.17 (s, 3H), 5.95 (s, 1H), 7.01 (dd, J=7.6, 2.4 Hz, 1H), 7.06-7.09 (m, 2H), 7.15-7.18 (m, 1H), 7.27-7.32 (m, 3H), 7.35-7.43 (m, 4H), 7.67 (d, J=8.4 Hz, 2H), 7.72 (d, J=2.0 Hz, 1H), 7.75 (dd, J=5.6, 2.0 Hz, 1H), 7.89 (d, J=8.8 Hz, 1H), 7.91 (d, J=2.0 Hz, 1H), 8.17-8.21 (m, 3H), 8.24 (d, J=8.8 Hz, 1H), 8.87 (d, J=5.6 Hz, 1H). $^{13}$C NMR (DMSO-d$_6$, 100 MHz): δ 12.16, 13.21, 103.03, 107.44, 110.16, 111.38, 113.08, 113.63, 115.07, 116.06, 118.16, 118.73, 120.21, 120.33, 120.65, 121.18, 121.45, 121.76, 123.49, 123.63, 126.08, 126.57, 130.35, 138.94, 139.16, 139.38, 140.04, 140.93, 147.11, 148.04, 151.38, 152.44, 154.68, 158.04.

Synthesis of 9-(4-(9H-carbazol-9-yl)pyridin-2-yl)-2-(3-(3,5-dimethyl-1H-pyrazol-1-yl)phenoxy)-9H-carbazole platinum complex PtON1N

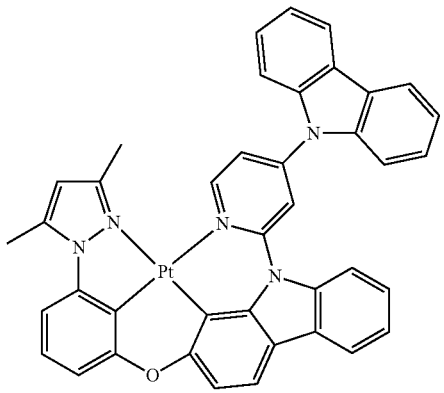

Figure 14:
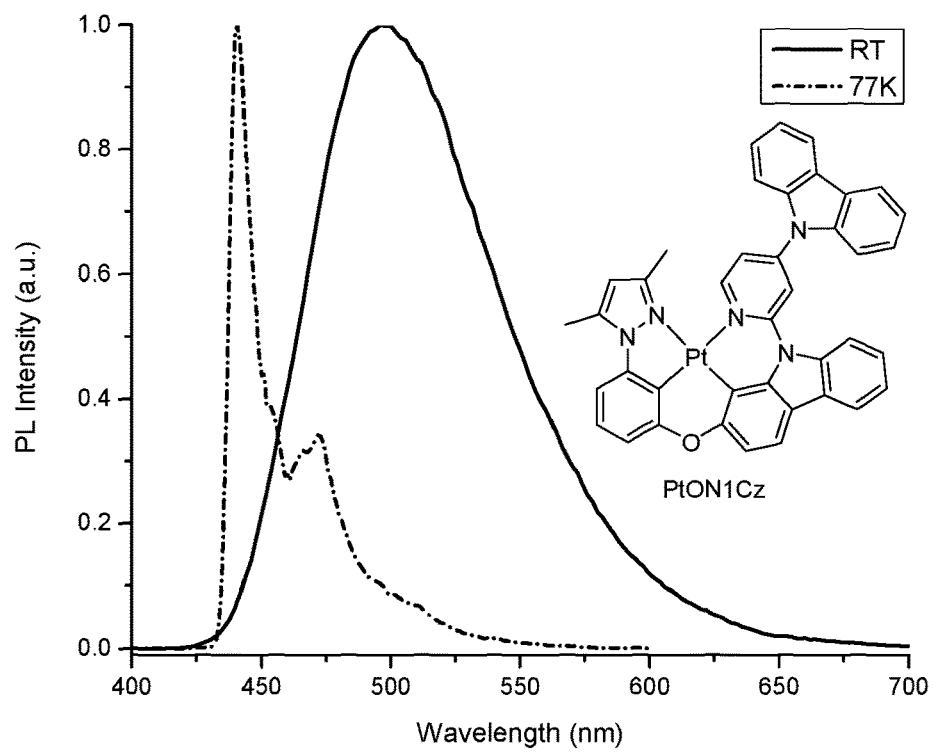
FIG. 14 shows emission spectra of PtON1Cz in CH$_2$Cl$_2$ at room temperature and in 2-methyl-THF at 77 K.

PtON1Cz was synthesized according to the procedure of synthesis of PtON1. 9-(4-(9H-carbazol-9-yl)pyridin-2-yl)-2-(3-(3,5-dimethyl-1H-pyrazol-1-yl)phenoxy)-9H-carbazole Ligand ON1Cz (910 mg, 1.53 mmol, 1.0 eq) was reacted with K$_2$PtCl$_2$ (672 mg, 1.60 mmol, 1.05 eq) in the presence of "Bu$_4$NBr (49 mg, 0.15 mmol, 0.1 eq) at room temperature for 18 hours and then at 105-115° C. for an additional 3 days. Purification of the crude product by flash chromatography on silica gel (eluent: dichloromethane/hexane=2:1) afforded the title compound as a orange solid (617 mg in 51% yield). Emission spectra of PtON1Cz at room temperature in CH$_2$Cl$_2$ and at 77 K in 2-methyl-THF are shown in FIG. 14. $^1$H NMR (DMSO-d$_6$, 400 MHz): 2.56 (s, 3H), 2.77 (s, 3H), 6.48 (s, 1H), 6.98 (d, J=8.0 Hz, 1H), 7.21 (d, J=8.0 Hz, 1H), 7.25 (d, J=8.0 Hz, 1H), 7.20-7.44 (m, 5H), 7.54 (d, J=7.6 Hz, 2H), 7.70 (dd, J=6.8, 2.0 Hz, 1H), 7.85 (d, J=8.0 Hz, 3H), 8.13 (d, J=7.6 Hz, 1H), 8.22-8.28 (m, 4H), 9.43 (d, J=6.0 Hz, 1H). $^{13}$C NMR (DMSO-d$_6$, 100 MHz): δ 100.44, 107.19, 110.35, 110.45, 110.91, 111.15, 112.33, 112.48, 114.90, 115.39, 115.93, 120.08, 120.85, 121.73, 123.13, 123.97, 124.64, 124.75, 126.89, 128.16, 137.96, 138.56, 142.07, 142.22, 146.76, 147.40, 149.58, 149.78, 151.65, 151.99, 155.44.

Example 19

Upon preparation of and analysis of the emission spectra of thin films prepared from Composition A (PtON1)

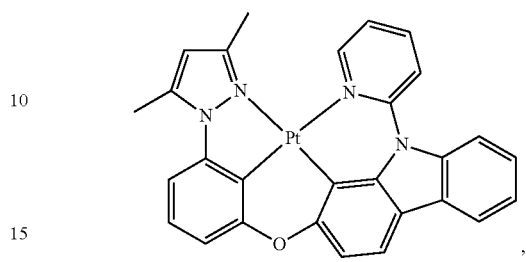

photoluminescent quantum yield measurements suggested quenching interactions between the dopant and host material of the composition. In contrast, thin films prepared from Composition B (PtON6)

Figure 15:
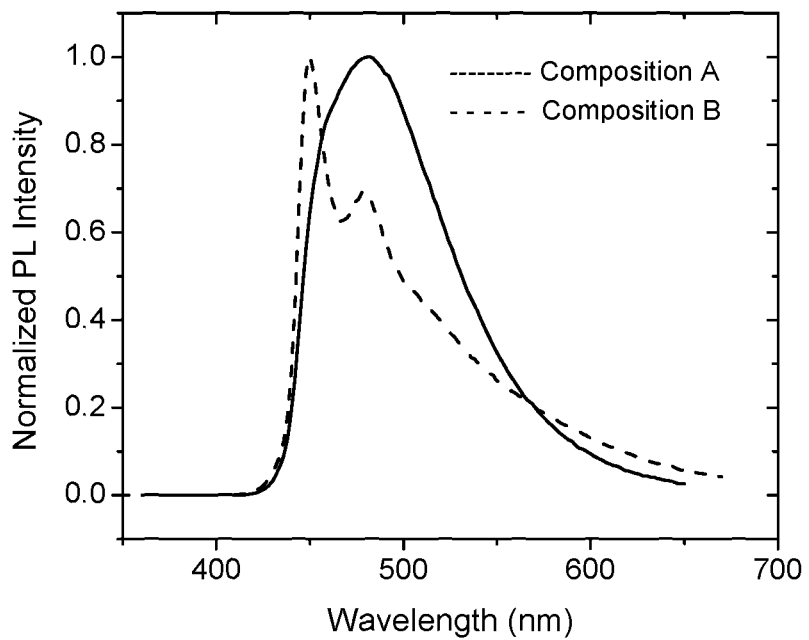
FIG. 15 shows normalized photoluminescent intensity for Composition A (PtON1) and for Composition B (PtON6).
Figure 16:
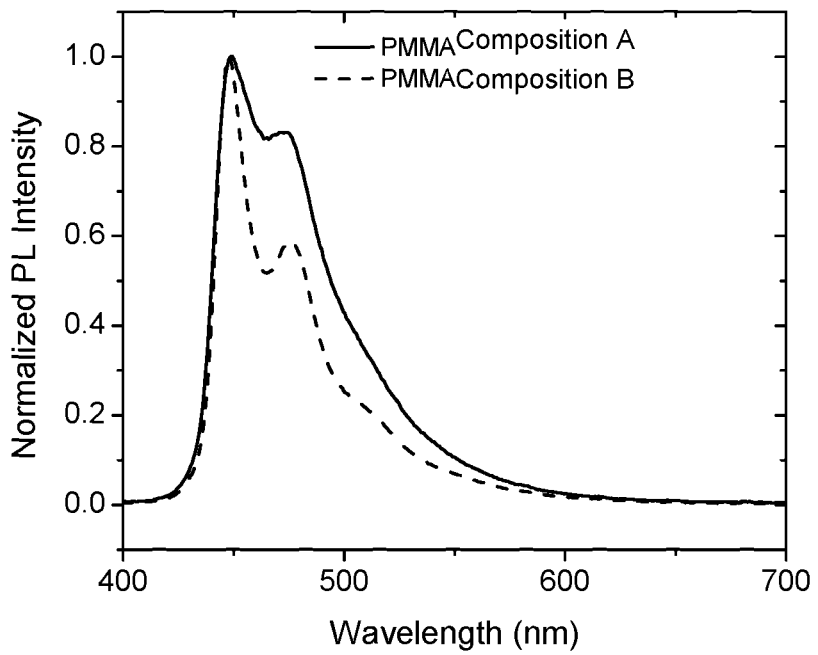
FIG. 16 shows normalized photoluminescent intensity for Composition A PMMA:(PtON1) and for Composition B PMMA:(PtON6).

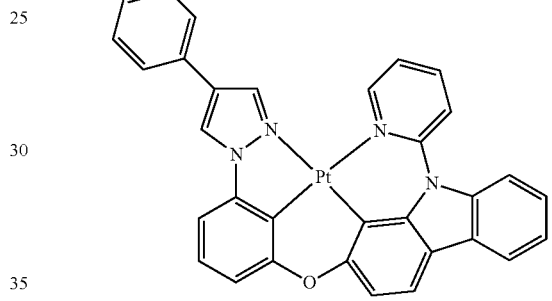

can exhibit beneficial photoluminescent properties without comprising excited state energy or lifetimes. Thus, substitution of a phenyl ring on the pyrazole of Composition A can be a useful substitution to improve the photoluminescent properties of the material and to potentially increase stability by extending conjugation of the pyrazole ring. Photoluminescent (PL) spectra for Composition A and Composition B in room temperature 2-methyltetrahydrofuran solution are shown in FIG. 15, where Composition B exhibits more vibronic character and bluer and narrower emission compared to Composition A. FIG. 16 shows a comparison of the emission spectra for the two compounds as doped into a polymethylmethacrylate (PMMA) optically inert matrix. As shown, the highest energy peak for both Composition A and Composition B are identical, indicating that phenyl substitution does not result in any significant red-shift in the emission spectra. Composition B exhibits a narrower emission spectrum having a more desirable blue emission. Both compounds exhibit a photoluminescent quantum yield (PLQY) in PMMA of about 80%. The excited state lifetime in a 77 K 2-methyltetrahydrofuran solution for Composition B is 9.3 microseconds compared to 9.7 microseconds for Composition A. In summary, phenyl substitution does not negatively affect the PLQY or dramatically increase the excited state lifetime by enabling a more ligand based emission.

A number of embodiments have been described. Nevertheless, it will be understood that various modifications may be made without departing from the spirit and scope of the

What is claimed is:

1. A composition comprising one or more compounds of the formula:

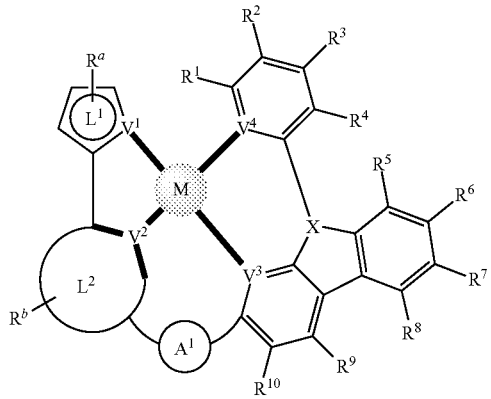

wherein, for each of the one or more compounds:

is

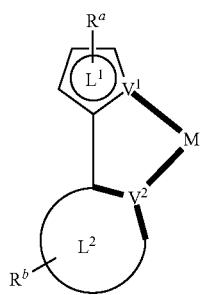

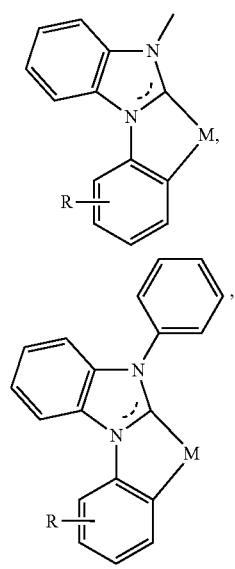

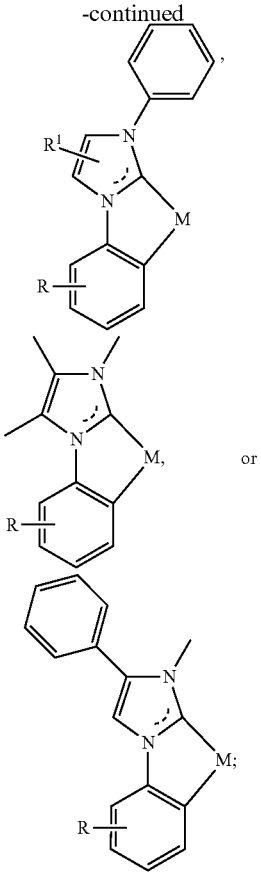

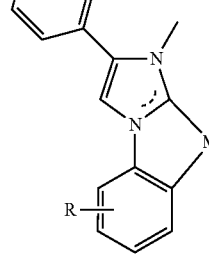

wherein A¹ represents oxygen (O);
X is N;
V³ is C;
V⁴ is N;
M represents platinum (Pt), gold (Au), iridium (Ir), rhodium (Rh), ruthenium (Ru), iron (Fe), cobalt (Co), nickel (Ni), copper (Cu), zinc (Zn), silver (Ag), mercury (Hg), cadmium (Cd), or zirconium (Zr), and
$R^1$, $R^2$, $R^3$, $R^4$, $R^5$, $R^6$, $R^7$, $R^8$, $R^9$, $R^{10}$, and R each independently represents mono-, di-, tri, or tetra-substitution, and each independently represents one or more of hydrogen, deuterium, a halogen atom, a hydroxyl group, a thiol group, a nitro group, a cyano group, a substituted or unsubstituted alkyl group, a substituted or unsubstituted haloalkyl group, a substituted or unsubstituted aralkyl group, a substituted or unsubstituted alkenyl group, a substituted or unsubstituted alkynyl group, a substituted or unsubstituted aryl group, a substituted or unsubstituted amino group, a substituted or unsubstituted mono- or dialkylamino group, a substituted or unsubstituted mono- or diarylamino group, a substituted or unsubstituted alkoxy group, a substituted or unsubstituted aryloxy group, a substituted or unsubstituted heteroaryl group, an alkoxycarbonyl group, an acyloxy group, an acylamino group, an alkoxycarbonylamino group, an aryloxycarbonylamino group, a sulfonylamino group, a sulfamoyl group, a carbamoyl group, an alkylthio group, a sulfinyl group, a ureido group, a phosphoramide group, a mercapto group, a sulfo group, a carboxyl group, a hydrazino group, a substituted silyl group, a polymeric group, or a combination thereof.

2. The composition of claim 1, wherein the polymeric group comprises a polyalkylene, a polyether, or a polyester.

3. A device comprising the composition of claim 1.

4. The device of claim 3, wherein the device comprises a full color display.

5. The device of claim 3, wherein the device is a photovoltaic device.

6. The device of claim 3, wherein the device is a luminescent display device.

7. The device of claim 3, wherein the device comprises an organic light emitting diode (OLED).

8. The device of claim 7, wherein the device comprises a phosphorescent organic light emitting diode.

9. The device of claim 7, wherein the device is a phosphorescent organic light emitting diode.

10. A light emitting device comprising the composition of claim 1.

11. The composition of claim 1, wherein the moiety

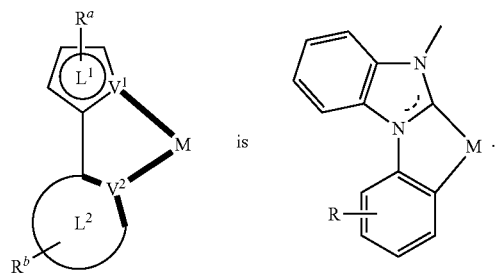

12. The composition of claim 1, wherein the moiety

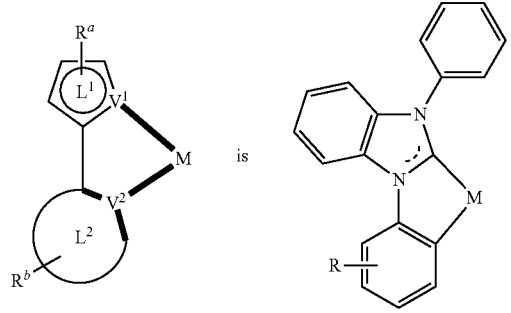

13. The composition of claim 1, wherein the moiety

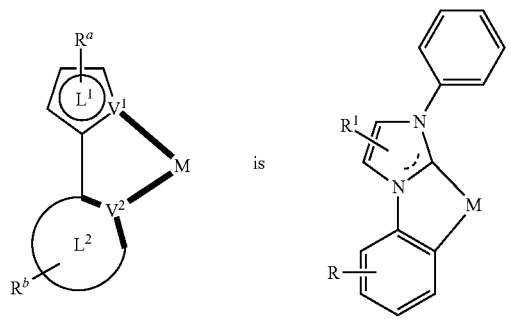

14. The composition of claim 1, wherein the moiety

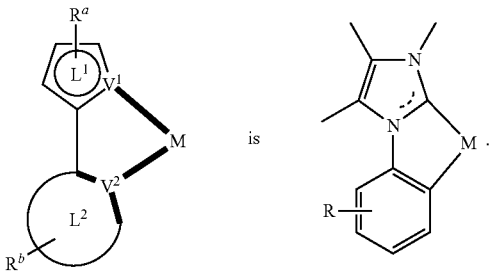

15. The composition of claim 1, wherein the moiety

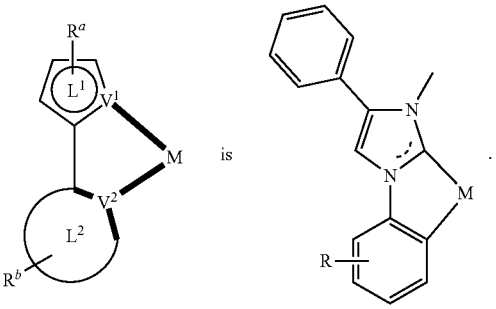

16. The composition of claim 1, wherein M represents platinum (Pt), gold (Au), iridium (Ir), and rhodium (Rh).

17. The composition of claim 1, wherein M represents platinum (Pt).

18. The composition of claim 1, wherein $R^1$, $R^2$, $R^3$, $R^4$, $R^5$, $R^6$, $R^7$, $R^8$, $R^9$, $R^{10}$, and R each independently represents hydrogen, a halogen atom, a hydroxyl group, a substituted or unsubstituted alkyl group, a substituted or unsubstituted alkenyl group, a substituted or unsubstituted alkynyl group, or a substituted or unsubstituted aryl group.

19. The composition of claim 1, wherein $R^1$, $R^2$, $R^3$, $R^4$, $R^5$, $R^6$, $R^7$, $R^8$, $R^9$, $R^{10}$, and R each independently represents hydrogen, a substituted or unsubstituted alkyl group, a substituted or unsubstituted alkenyl group, or a substituted or unsubstituted alkynyl group.

20. The composition of claim 1, wherein $R^1$, $R^2$, $R^3$, $R^4$, $R^5$, $R^6$, $R^7$, $R^8$, $R^9$, $R^{10}$, and R each independently represents hydrogen, or a substituted or unsubstituted alkyl group.

* * * * *